(12) United States Patent
Lee et al.

(10) Patent No.: US 9,975,852 B2
(45) Date of Patent: May 22, 2018

(54) QUINOLINE SULFONYL DERIVATIVES AND USES THEREOF

(71) Applicant: Health Sciences North Research Institute, Sudbury (CA)

(72) Inventors: Hoyun Lee, Sudbury (CA); Viswas Raja Solomon, Tamilnadu (IN); Sheetal Pundir, Sudbury (CA)

(73) Assignee: Health Sciences North Research Institute, Sudbury, Ontario (CA)

( * ) Notice: Subject to any disclaimer, the term of this patent is extended or adjusted under 35 U.S.C. 154(b) by 0 days. days.

(21) Appl. No.: 14/772,701

(22) PCT Filed: Feb. 18, 2014

(86) PCT No.: PCT/CA2014/000121
§ 371 (c)(1),
(2) Date: Sep. 3, 2015

(87) PCT Pub. No.: WO2014/134705
PCT Pub. Date: Sep. 12, 2014

(65) Prior Publication Data
US 2015/0376132 A1 Dec. 31, 2015

Related U.S. Application Data

(60) Provisional application No. 61/772,032, filed on Mar. 4, 2013.

(51) Int. Cl.
| | | |
|---|---|---|
| C07D 215/46 | (2006.01) | |
| C07D 409/12 | (2006.01) | |
| A61K 31/496 | (2006.01) | |
| A61K 45/06 | (2006.01) | |
| A61K 31/47 | (2006.01) | |
| A61K 31/337 | (2006.01) | |
| A61K 31/4188 | (2006.01) | |
| A61K 31/495 | (2006.01) | |
| A61K 31/635 | (2006.01) | |

(52) U.S. Cl.
CPC .......... *C07D 215/46* (2013.01); *A61K 31/337* (2013.01); *A61K 31/4188* (2013.01); *A61K 31/47* (2013.01); *A61K 31/495* (2013.01); *A61K 31/496* (2013.01); *A61K 31/635* (2013.01); *A61K 45/06* (2013.01); *C07D 409/12* (2013.01)

(58) Field of Classification Search
None
See application file for complete search history.

(56) References Cited

U.S. PATENT DOCUMENTS

| | | | |
|---|---|---|---|
| 7,220,856 B2 * | 5/2007 | Dunning | C07D 215/46 540/484 |
| 2003/0229119 A1 | 12/2003 | Kym et al. | |
| 2013/0165458 A1 | 6/2013 | Huang et al. | |

FOREIGN PATENT DOCUMENTS

| | | |
|---|---|---|
| WO | 2003070244 A1 | 8/2003 |
| WO | 2004002960 A1 | 1/2004 |
| WO | 2005066172 A1 | 7/2005 |
| WO | 2005113542 A2 | 12/2005 |
| WO | 2008011476 A2 | 1/2008 |
| WO | 2009148659 A2 | 12/2009 |
| WO | 2012041872 A1 | 4/2012 |
| WO | 2012079164 A1 | 6/2012 |
| WO | 2014032737 A1 | 3/2014 |
| WO | 2014086687 A1 | 6/2014 |

OTHER PUBLICATIONS

Burger's Medicinal Chemistry,edited by Manfred E. Wolff, 5th Ed. Part 1, pp. 975-977 (1995).*
Banker et al. "Modern Pharmaceutics", 3rd Ed. p. 596 (1996).*
Simplicio et al. Molecules 2008, 13, 519-547.*
CA Registry No. 1316407-86-9, entered into CA Registry File on Aug. 12, 2011, supplied by FCH Group.*
CA Registry No. 1322359-10-3, entered into CA Registry File on Aug. 24, 2011, supplied by FCH Group.*
CA Registry No. 775302-73-3, entered into CA Registry File on Nov. 5, 2004, supplied by Scientific Exchange Inc.*
FCH Group Product Guide, 1 page, retrieved from the Internet at http://fchgroup.net/products.php on Apr. 5, 2014.*
Crawford et al. J. Cell Commun. Signal. (2011) 5:101-110.*
Holliday and Speirs Breast Cancer Research 2011, 13:215, pp. 1-7.*
Cancer Drug Design and Discovery, Neidle, Stephen,ed. (Elsevier/Academic Press), pp. 427-431 (2008).*
Li et al. PLoS ONE 10(10) p. 1-21 (2015).*
Manasanch et al. Nature Reviews | Clinical Oncology, vol. 14, p. 417-433 (2017).*
Ekoue-Kovi et al. "Synthesis and antimalarial activity of new 4-amino-7-chloroquinolyl amides, sulfonamides, ureas and thioureas" Bioorganic & Medicinal Chemistry (2009), 17(1), pp. 270-283.
Klingenstein et al. "Similar Structure-Activity Relationships of Quinoline Derivatives for Antiprion and Antimalarial Effects" Journal of Medicinal Chemistry (2006), 49(17), pp. 5300-5308.

(Continued)

*Primary Examiner* — Emily Bernhardt
(74) *Attorney, Agent, or Firm* — Bereskin & Parr LLP/S.E.N.C.R.L., s.r.l.; Michael Fenwick

(57) ABSTRACT

The present disclosure relates to quinoline sulfonyl compounds, compositions comprising these compounds and their use, in particular for the treatment of cancer. In particular, the present disclosure includes compounds of Formula (I), and compositions and uses thereof:

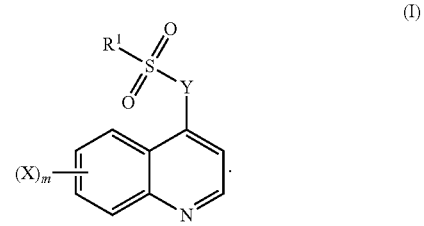

(I)

17 Claims, 44 Drawing Sheets

(56) References Cited

OTHER PUBLICATIONS

He et al. "Design of antineoplastic agents based on the '2-phenylnaphthalene-type' structural pattern-synthesis and biological activity studies of 11H-indolo[3.2-c] quinoline derivatives" European Journal of Medicinal Chemistry (2003), 38(1), pp. 101-107.

Chibale et al. "Modulation of human mammary cell sensitivity to paclitaxel by new quinoline sulfonamides" Bioorganic & Medicinal Chemistry Letters (2001), 11(18), pp. 2457-2460.

El Hamouly, W. S. "Synthesis of some substituted 9-anilinoacridines and 4-anilinoquinolines of possible antitumor activity" Egyptian Journal of Chemistry (1995), 38(4), pp. 393-402.

Denny et al. "'Minimal' DNA-intercalating agents as antitumor drugs: 2-styrylquinoline analogues of amsacrine" Anti-Cancer Drug Design (1987), 2(3), pp. 263-270.

Cain et al. "Potential antitumor agents. 14. Acridylmethanesulfonanilides" Journal of Medicinal Chemistry (1974), 17(9), pp. 922-930.

Salahuddin et al. "Synthesis and evaluation of 7-chloro-4-(piperazin-1-yl) quinoline-sulfonamide as hybrid antiprotozoal agents" Bioorganic & Medicinal Chemistry (2013), 21(11), pp. 3080-3089.

Robert et al. "Structural analog of sildenafil identified as a novel corrector of the F508del-CFTR trafficking defect" Molecular Pharmacology (2008), 73(2), pp. 478-489.

He et al. "Probabilistic Neural Network Multiple Classifier System for Predicting the Genotoxicity of Quinolone and Quinoline Derivatives" Chemical Research in Toxicology (2005), 18(3), pp. 428-440.

Solomon et al. "Design and synthesis of chloroquine analogs with anti-breast cancer property" European Journal of Medicinal Chemistry (2010), 45, pp. 3916-3923.

Cichero et al., "Scouting new molecular targets for CFTR therapy: the HSC70/BAG-1 complex. A computational study" Med Chem Res (2012), 21, pp. 4430-4436.

Loo et al., "Corrector-mediated rescue of misprocessed CFTR mutants can be reduced by the P-glycoprotein drug pump" Biochemical Pharmacology, (2012), 83, pp. 345-354.

STN International, CAS Registry, Registry No. 1387266-11-6; Chemical Library Supplier: Ukrorgsyntez Ltd.; Entered STN: Aug. 7, 2012.

STN International, CAS Registry, Registry No. 1387266-11-6; Catalog Name: Aurora Screening Library; Publication Date: Jul. 3, 2013.

STN International, CAS Registry, Registry No. 1322344-28-4; Chemical Library Supplier: FCH Group; Entered STN: Aug. 24, 2011.

STN International, CAS Registry, Registry No. 1322344-28-4; Catalog Name: AKos Screening Library; Publication Date: Aug. 20, 2013.

STN International, CAS Registry, Registry No. 1316572-75-4; Chemical Library Supplier: FCH Group; Entered STN: Aug. 12, 2011.

STN International, CAS Registry, Registry No. 1316572-75-4; Catalog Name: AKos Screening Library; Publication Date: Aug. 20, 2013.

STN International, CAS Registry, Registry No. 1304915-33-0; Chemical Catalog Supplier: Ryan Scientific, Inc.; Entered STN: Jun. 3, 2011.

STN International, CAS Registry, Registry No. 1304915-33-0; Catalog Name: Aurora Building Blocks; Publication Date: Jul. 3, 2013.

STN International, CAS Registry, Registry No. 1199400-09-3; Chemical Library Supplier: AMRI; Entered STN: Dec. 30, 2009.

STN International, CAS Registry, Registry No. 1199383-69-1; Chemical Library Supplier: AMRI; Entered STN: Dec. 30, 2009.

STN International, CAS Registry, Registry No. 1193085-59-4; Chemical Library Supplier: AMRI; Entered STN: Nov. 22, 2009.

STN International, CAS Registry, Registry No. 1192929-47-7; Chemical Library Supplier: AMRI; Entered STN: Nov. 20, 2009.

STN International, CAS Registry, Registry No. 1192929-44-4; Chemical Library Supplier: AMRI; Entered STN: Nov. 20, 2009.

STN International, CAS Registry, Registry No. 1192929-38-6; Chemical Library Supplier: AMRI; Entered STN: Nov. 20, 2009.

STN International, CAS Registry, Registry No. 1172009-51-6; Chemical Library Supplier: Ambinter; Entered STN: Aug. 3, 2009.

STN International, CAS Registry, Registry No. 1171355-77-3; Chemical Library Supplier: Ambinter; Entered STN: Aug. 2, 2009.

STN International, CAS Registry, Registry No. 1171191-06-2; Chemical Library Supplier: Ambinter; Entered STN: Jul. 31, 2009.

STN International, CAS Registry, Registry No. 1171148-05-2; Chemical Library Supplier: Ambinter; Entered STN: Jul. 31, 2009.

STN International, CAS Registry, Registry No. 1170619-32-5; Chemical Library Supplier: Ambinter; Entered STN: Jul. 30, 2009.

STN International, CAS Registry, Registry No. 1153796-97-4; Chemical Catalog Supplier: UkrOrgSynthesis; Entered STN: Jun. 8, 2009.

STN International, CAS Registry, Registry No. 1153796-97-4; Catalog Name: Aurora Building Blocks; Publication Date: Jul. 3, 2013.

STN International, CAS Registry, Registry No. 1046968-30-2; Chemical Library Supplier: Albany Molecular Research, Inc. (AMRI); Entered STN: Sep. 7, 2008.

STN International, CAS Registry, Registry No. 1046967-16-1; Chemical Library Supplier: Albany Molecular Research, Inc. (AMRI); Entered STN: Sep. 7, 2008.

STN International, CAS Registry, Registry No. 1046965-08-5; Chemical Library Supplier: Albany Molecular Research, Inc. (AMRI); Entered STN: Sep. 7, 2008.

STN International, CAS Registry, Registry No. 1046963-92-1; Chemical Library Supplier: Albany Molecular Research, Inc. (AMRI); Entered STN: Sep. 7, 2008.

STN International, CAS Registry, Registry No. 1045821-07-5; Chemical Library Supplier: Albany Molecular Research, Inc. (AMRI); Entered STN: Sep. 2, 2008.

STN International, CAS Registry, Registry No. 1045788-47-3; Chemical Library Supplier: Albany Molecular Research, Inc. (AMRI); Entered STN: Sep. 2, 2008.

STN International, CAS Registry, Registry No. 1045718-04-4; Chemical Library Supplier: Albany Molecular Research, Inc. (AMRI); Entered STN: Sep. 2, 2008.

STN International, CAS Registry, Registry No. 1045717-43-8; Chemical Library Supplier: Albany Molecular Research, Inc. (AMRI); Entered STN: Sep. 2, 2008.

STN International, Cas Registry, Registry No. 1045589-60-3; Chemical Library Supplier: Albany Molecular Research, Inc. (AMRI); Entered STN: Sep. 1, 2008.

STN International, CAS Registry, Registry No. 763024-88-0; Entered STN: Oct. 15, 2004.

STN International, CAS Registry, Registry No. 337330-67-3; Chemical Library Supplier: ComGenex International Inc.; Entered STN: May 22, 2001.

STN International, CAS Registry, Registry No. 337330-61-7; Chemical Library Supplier: ComGenex International Inc.; Entered STN: May 22, 2001.

STN International, CAS Registry, Registry No. 337330-55-9; Chemical Library Supplier: ComGenex International Inc.; Entered STN: May 22, 2001.

STN International, CAS Registry, Registry No. 337330-49-1; Chemical Library Supplier: ComGenex International Inc.; Entered STN: May 22, 2001.

STN International, CAS Registry, Registry No. 337330-43-5; Chemical Library Supplier: ComGenex International Inc.; Entered STN: May 22, 2001.

STN International, CAS Registry, Registry No. 337330-37-7; Chemical Library Supplier: ComGenex International Inc.; Entered STN: May 22, 2001.

STN International, CAS Registry, Registry No. 335664-52-3; Chemical Library Supplier: ComGenex International Inc.; Entered STN: May 16, 2001.

STN International, CAS Registry, Registry No. 1498782-38-9; Chemical Catalog Supplier: Aurora Fine Chemicals; Entered STN: Dec. 19, 2013.

(56) References Cited

OTHER PUBLICATIONS

STN International, CAS Registry, Registry No. 1498782-38-9; Catalog Name: Aurora Building Blocks; Publication Date: Jul. 3, 2013.

STN International, CAS Registry, Registry No. 1485560-83-5; Chemical Catalog Supplier: Aurora Fine Chemicals; Entered STN: Dec. 2, 2013.

STN International, CAS Registry, Registry No. 1436306-11-4; Chemical Catalog Supplier; Ukrogsyntez Ltd.; Entered STN: Jun. 9, 2013.

STN International, CAS Registry, Registry No. 1436306-11-4; Catalog Name: Interchim Screening Library; Publication Date: Jun. 19, 2013.

Kaijun et al., "Marizomib activity as a single agent in malignant gliomas: ability to cross the blood-brain barrier" Neuro-Oncology 18(6), 840-848, 2016.

Potts et al., "Marizomib, a Proteasome Inhibitor for All Seasons: Preclinical Profile and a Framework for Clinical Trials" Curr Cancer Drug Targets. Mar. 2011; 11(3): 254-284 (Author manuscript; PMC Jul. 16, 2013).

Bota et al., "Phase 1, Multicenter, Open-Label, Dose-Escalation Study of Marizomib (MRZ) and Bevacizumab (BEV) in WHO Grade IV Malignant Glioma (G4 MG)" American Society for Clinical Oncology (ASCO) annual meeting in Chicago, Jun. 4, 2016 (poster).

\* cited by examiner

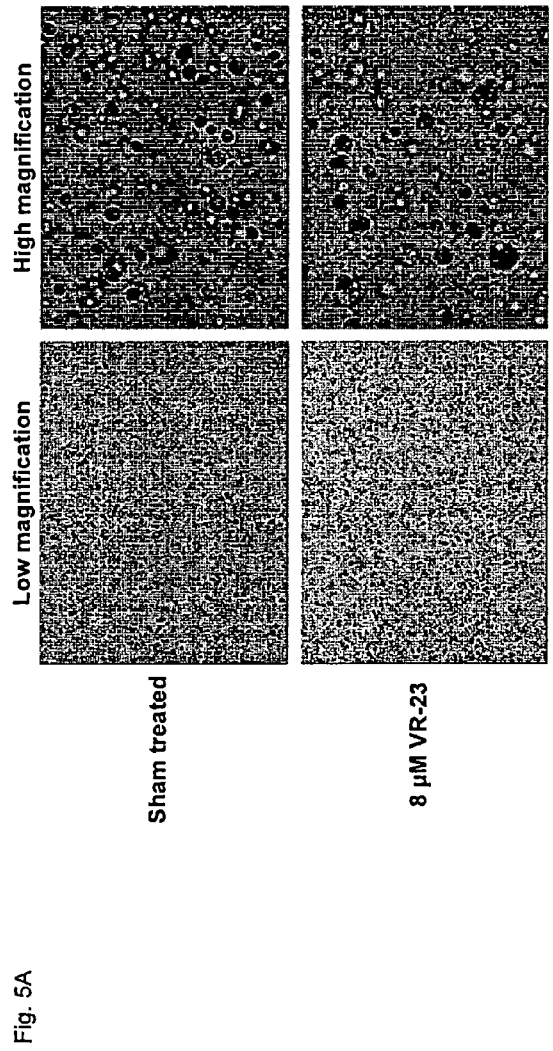
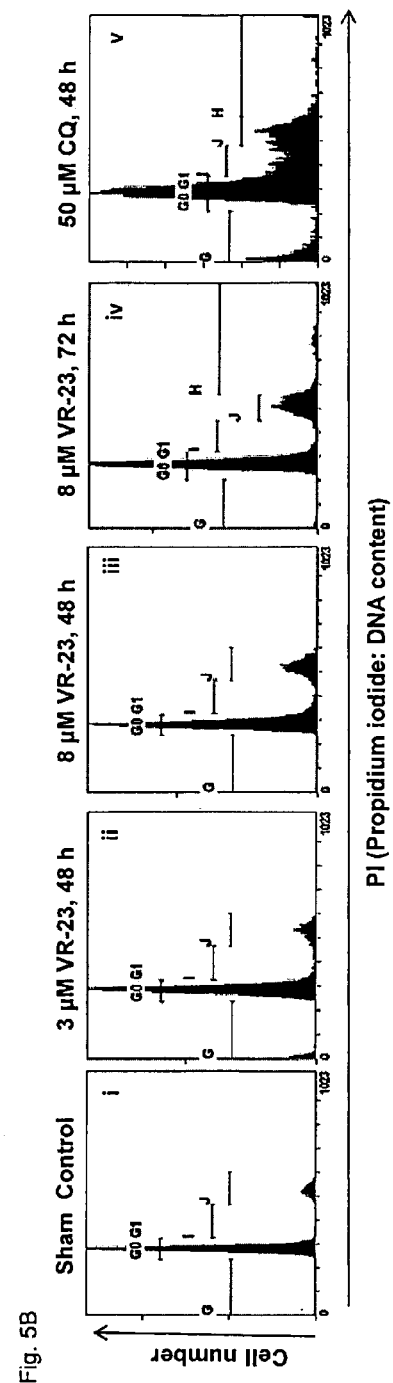
Fig. 5A
Fig. 5B

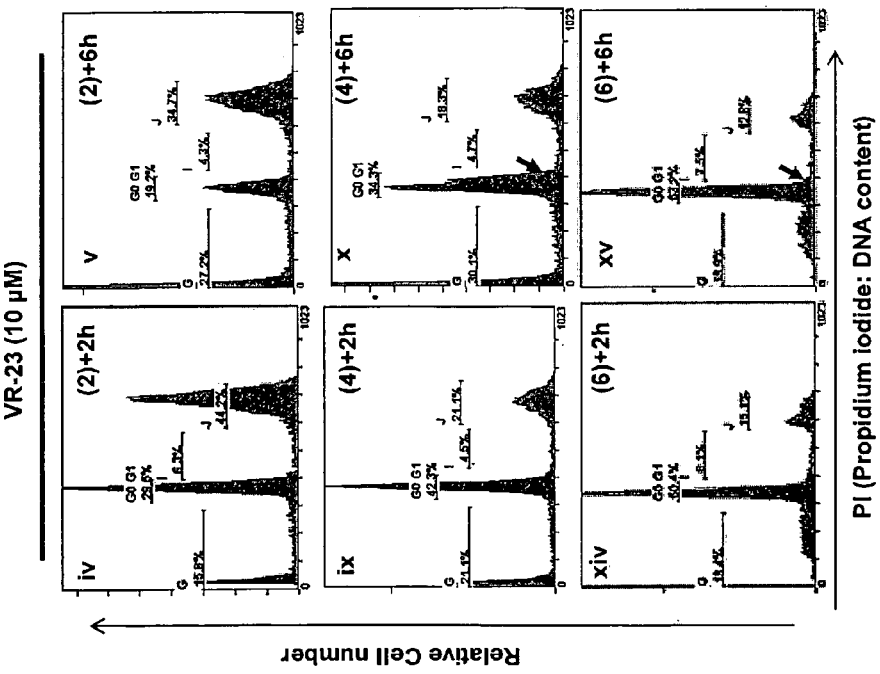

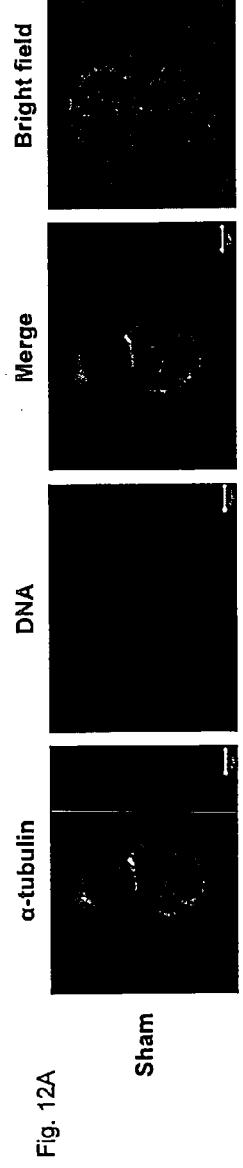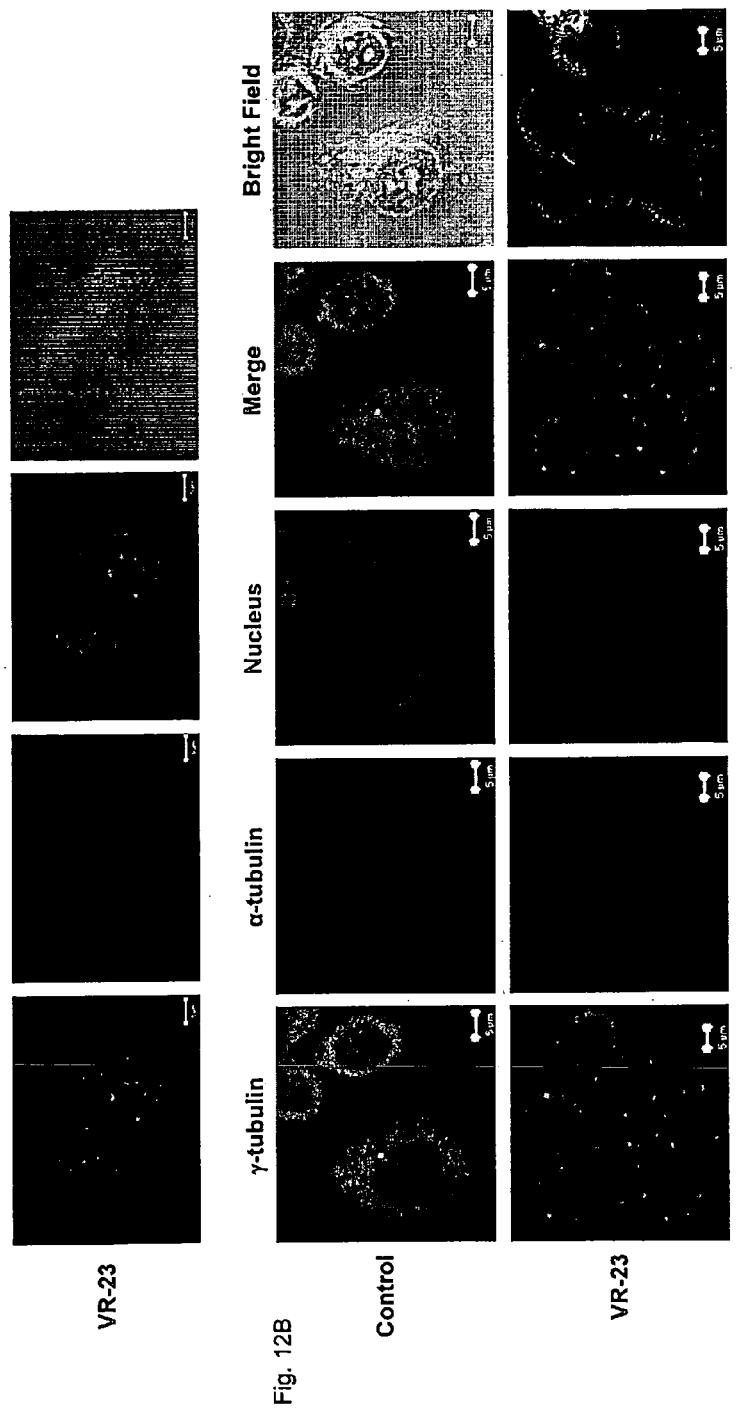
Fig. 12A
Fig. 12B

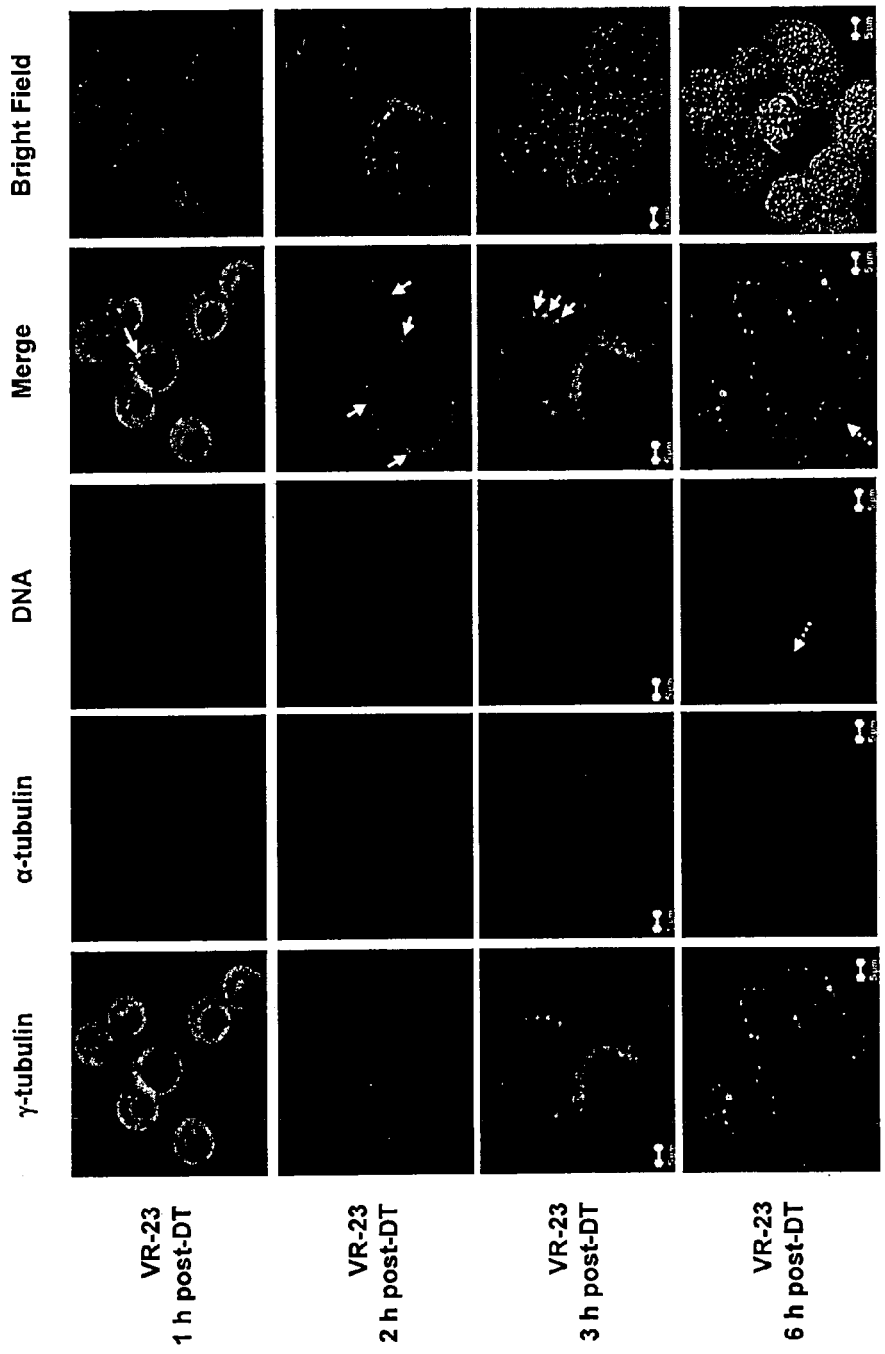

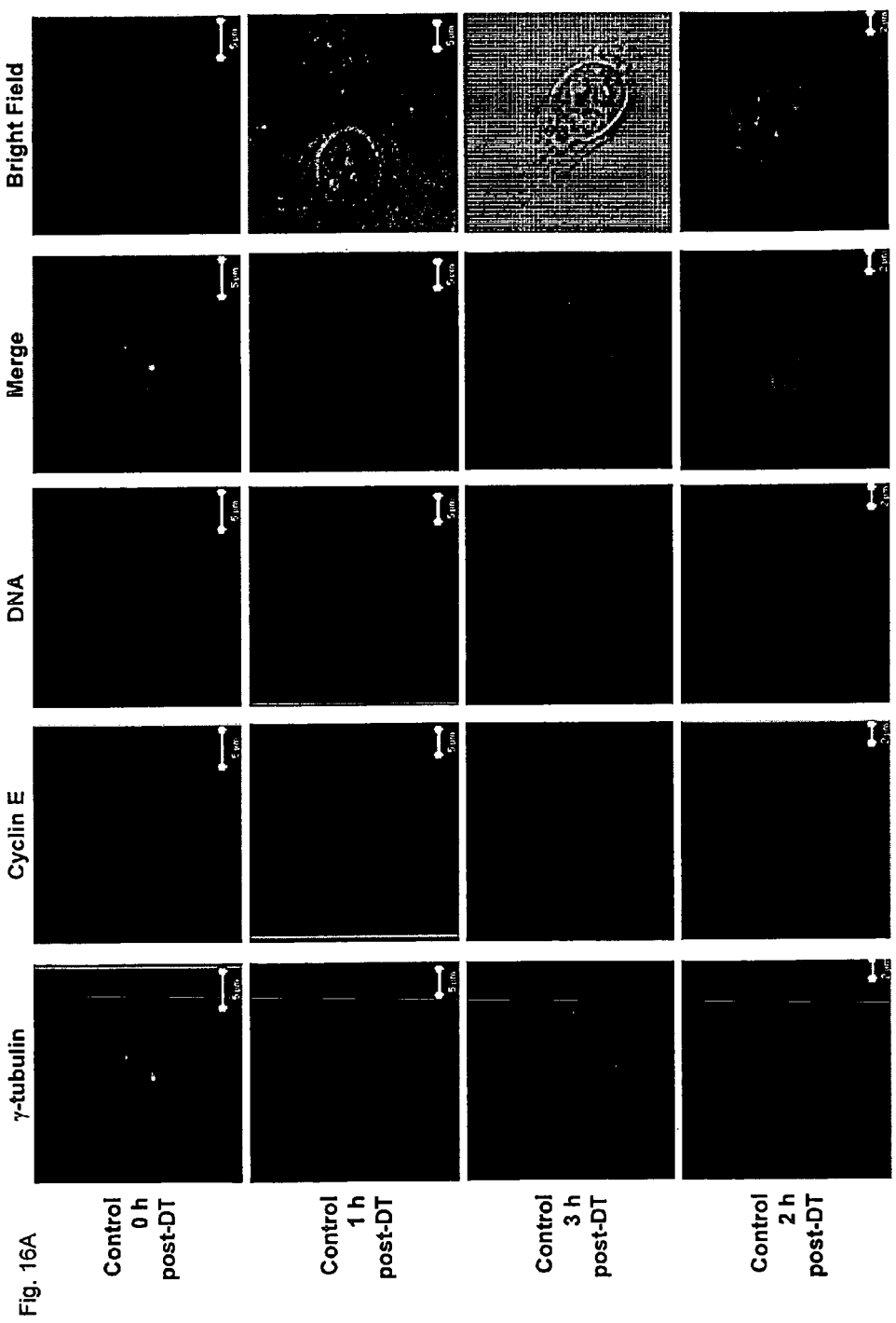

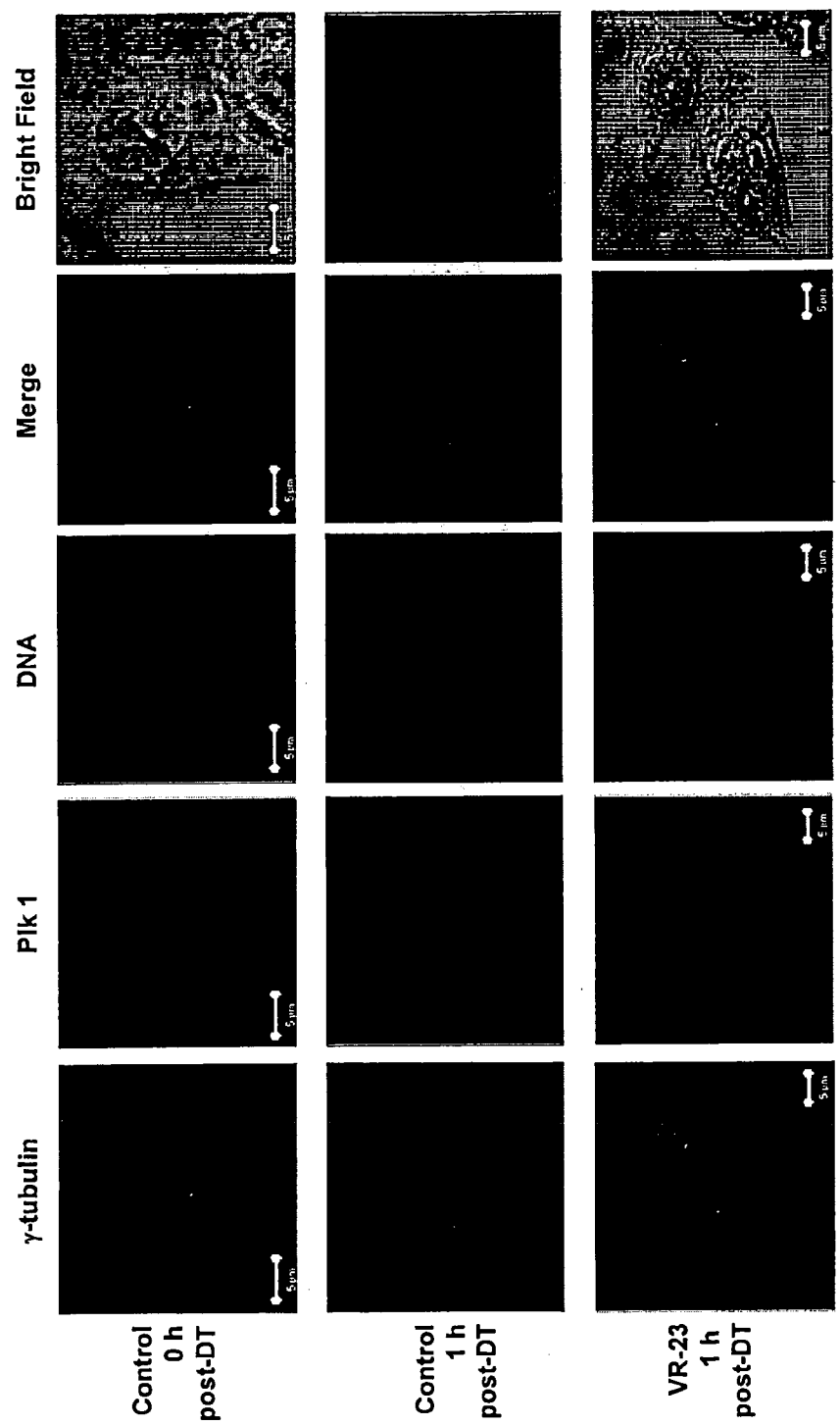

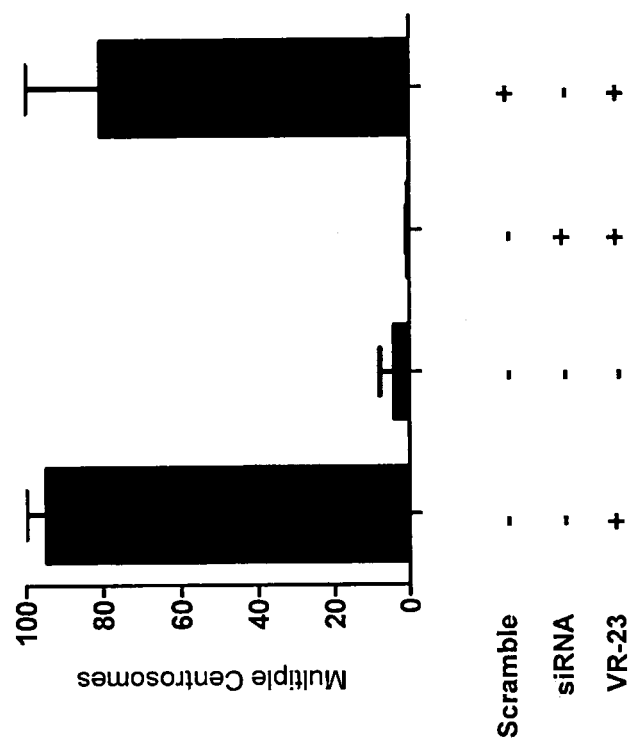

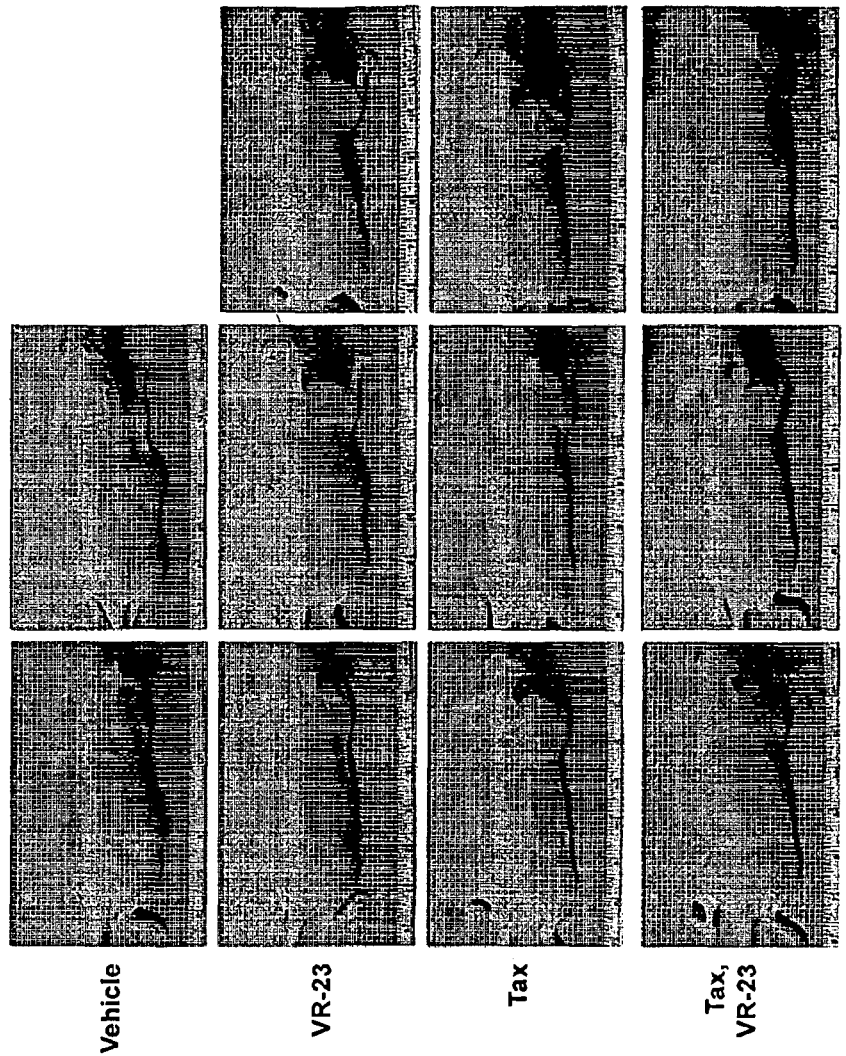

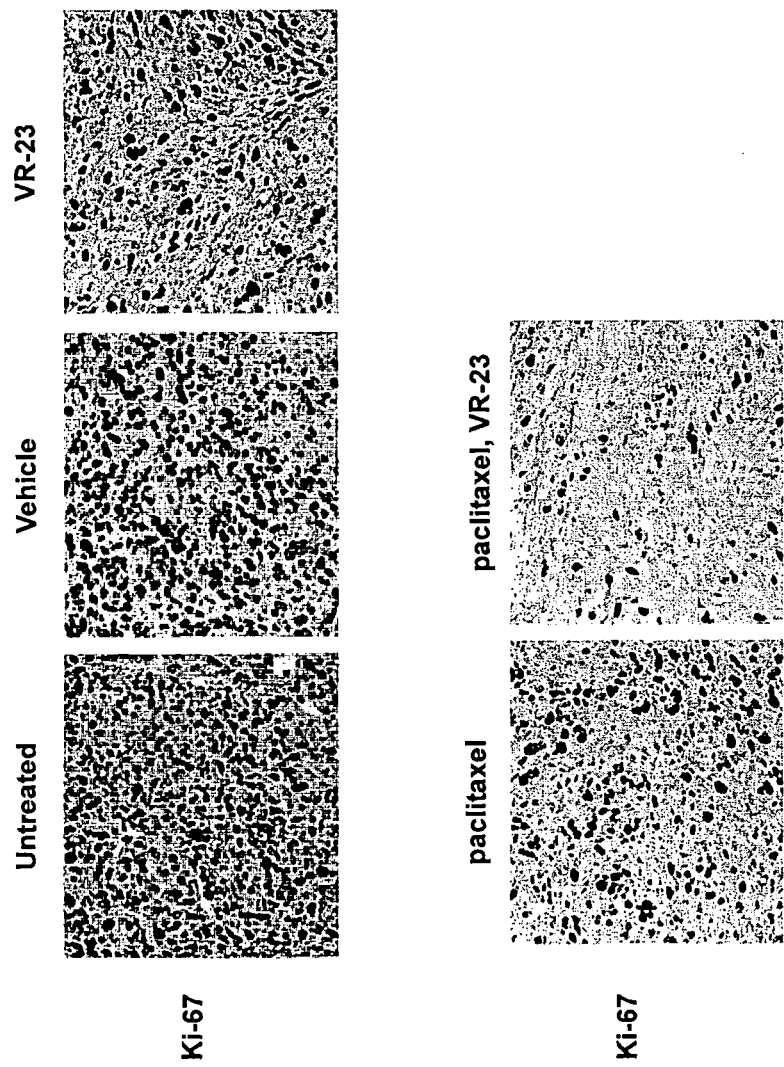

QUINOLINE SULFONYL DERIVATIVES AND USES THEREOF

CROSS REFERENCE TO RELATED APPLICATIONS

This application is a national phase entry of PCT/CA2014/000121 filed Feb. 18, 2014 (which designates the U.S.) which claims the benefit of and priority from U.S. Provisional Patent Application No. 61/772,032, filed on Mar. 4, 2013, all of which are incorporated herein by reference in its their entirety.

FIELD OF THE DISCLOSURE

The present disclosure relates to quinoline sulfonyl derivatives, compositions comprising said quinoline sulfonyl derivatives, and uses thereof.

BACKGROUND

Along with radiation, chemotherapy is the mainstay of cancer therapy. However, most of the currently available chemotherapeutic agents often cause side effects, limiting the use of an effective drug dosage. Furthermore, tumor cells often develop resistance to anticancer drugs. These two problems are largely responsible for the failure of current cancer therapy.

Certain quinoline compounds, such as chloroquine, have been demonstrated to kill cells in a cancer-specific manner, although their cell-killing effects are usually low. In addition, certain quinoline compounds have been demonstrated to be useful as sensitizers when used in combination with radiation or other anticancer agents. In other studies, it was demonstrated in vitro and in vivo that certain sulfonyl derivatives possess antitumor activity. Still, the low efficacy of currently available quinoline compounds necessitates the development of more efficient (and still safe) quinoline compounds, for use, e.g. in the treatment of cancer.

Many anticancer agents kill cancer and non-cancer cells equally well. This indiscriminate killing of cancer and normal cells by anticancer drugs may be responsible, at least in part, for the high side effects shown by many anticancer drugs. Therefore, there is a need to develop compounds with high efficacy and low side effects, for example compounds that can kill cells in a cancer-specific manner, and to develop compounds that suppress the development of drug resistance.

SUMMARY OF THE DISCLOSURE

Accordingly, in one aspect, the disclosure relates to a compound of Formula (I):

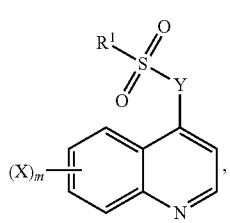

(I)

wherein,
X is halo, hydroxy, $C_{1-6}$alkyl, $C_{2-6}$alkenyl, $C_{2-6}$alkynyl, $C_{1-6}$haloalkyl, $C_{1-6}$alkoxy, $C_{6-14}$aryl, heteroaryl, heterocyclyl, $C_{3-10}$cycloalkyl or $C_{3-10}$cycloalkenyl, wherein the latter 10 moieties are optionally substituted with one or more of:
1. halo;
2. hydroxy;
3. $C_{1-6}$alkyl;
4. $C_{2-6}$alkenyl;
5. $C_{2-6}$alkynyl;
6. $C_{1-6}$haloalkyl;
7. $C_{1-6}$alkoxy;
8. nitro;
9. —C(O)O—$C_{1-10}$alkyl;
10. —C(O)O—$C_{6-14}$aryl;
11. $C_{6-14}$aryl, optionally substituted with one or more of halo or $C_{1-6}$alkyl; or
12. —$NR^8R^9$, wherein $R^8$ and $R^9$ are each individually selected from H and $C_{1-6}$alkyl;

m is 0, 1, or 2;
Y is —N(R)$C_{1-10}$alkyleneN(R)—, —N(R)$C_{2-10}$alkenyleneN(R)—, —N(R)heterocyclylN(R)—, —N(R)$C_{6-14}$arylN(R)—, —N(R)heteroarylN(R)—, —N(R)$C_{3-10}$cycloalkylN(R)—, —N(R)$C_{3-10}$cycloalkenylN(R)—, or

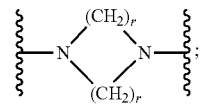

each of which are optionally substituted with one or two substituents selected from amino, halo and $C_{1-6}$alkyl;
wherein each r is independently or simultaneously 1, 2 or 3;
each R is independently or simultaneously H or $C_{1-6}$alkyl; and
$R^1$ is $C_{1-6}$alkyl, $C_{2-6}$alkenyl, $C_{2-6}$alkynyl, $C_{6-14}$aryl, heteroaryl, heterocyclyl, $C_{3-10}$cycloalkyl or $C_{3-10}$cycloalkenyl, each of which is optionally substituted with one or more of:
1. halo;
2. hydroxy;
3. nitro;
4. $C_{1-6}$alkyl;
5. $C_{2-6}$alkenyl;
6. $C_{2-6}$alkynyl;
7. $C_{1-6}$haloalkyl;
8. $C_{1-6}$alkoxy;
9. —C(O)O—$C_{1-6}$alkyl;
10. —C(O)O—$C_{6-14}$aryl;
11. $C_{6-14}$aryl, optionally substituted with halo or $C_{1-6}$alkyl;
12. heteroaryl, optionally substituted with halo or $C_{1-6}$alkyl; or
13. —$NR^8R^9$, wherein $R^8$ and $R^9$ are each individually selected from H and $C_{1-6}$alkyl,
or a pharmaceutically acceptable salt, solvate or prodrug thereof,
with the proviso that the compound is not:
7-Chloro-4-(4-tosylpiperazin-1-yl)quinoline,
7-Chloro-4-(4-(4-chlorophenylsulfonyl)piperazin-1-yl)quinoline,
7-Chloro-4-(4-(3-nitrophenylsulfonyl)piperazin-1-yl)quinoline, or
5-Dimethylamino-naphthalene-1-sulfonic acid [3-(7-chloroquinolin-4-ylamino)-propyl]-amide.

In another aspect, the compound of Formula (I) is a compound of Formula (IA):

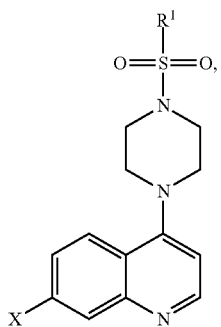

(IA)

wherein

X is halo, hydroxy, $C_{1-6}$alkyl, $C_{2-6}$alkenyl, $C_{2-6}$alkynyl, $C_{1-6}$haloalkyl, $C_{1-6}$alkoxy, $C_{6-14}$aryl, heteroaryl, heterocyclyl, $C_{3-10}$cycloalkyl or $C_{3-10}$cycloalkenyl, wherein the latter 10 moieties are optionally substituted with one or more of:
1. halo;
2. hydroxy;
3. $C_{1-6}$alkyl;
4. $C_{2-6}$alkenyl;
5. $C_{2-6}$alkynyl;
6. $C_{1-6}$haloalkyl;
7. $C_{1-6}$alkoxy;
8. nitro;
9. —C(O)O—$C_{1-10}$alkyl;
10. —C(O)O—$C_{6-14}$aryl;
11. $C_{6-14}$aryl, optionally substituted with one or more of halo or $C_{1-6}$alkyl; or
12. —NR$^8$R$^9$, wherein R$^8$ and R$^9$ are each individually selected from H and $C_{1-6}$alkyl; and R$^1$ is $C_{1-6}$alkyl, $C_{2-6}$alkenyl, $C_{2-6}$alkynyl, $C_{6-14}$aryl, heteroaryl, heterocyclyl, $C_{3-10}$cycloalkyl or $C_{3-10}$cycloalkenyl, each of which is optionally substituted with one or more of:
1. halo;
2. hydroxy;
3. nitro;
4. $C_{1-6}$alkyl;
5. $C_{2-6}$alkenyl;
6. $C_{2-6}$alkynyl;
7. $C_{1-6}$haloalkyl;
8. $C_{1-6}$alkoxy;
9. —C(O)O—$C_{1-6}$alkyl;
10. —C(O)O—$C_{6-14}$aryl;
11. $C_{6-14}$aryl, optionally substituted with halo or $C_{1-6}$alkyl;
12. heteroaryl, optionally substituted with halo or $C_{1-6}$alkyl; or
13. —NR$^8$R$^9$, wherein R$^8$ and R$^9$ are each individually selected from H and $C_{1-6}$alkyl, or a pharmaceutically acceptable salt, solvate or prodrug thereof,
with the proviso that the compound is not:
7-Chloro-4-(4-tosylpiperazin-1-yl)quinoline,
7-Chloro-4-(4-(4-chlorophenylsulfonyl)piperazin-1-yl)quinoline, or
7-Chloro-4-(4-(3-nitrophenylsulfonyl)piperazin-1-yl)quinoline.

In another aspect, the compound of Formula (I) is a compound of Formula (IB):

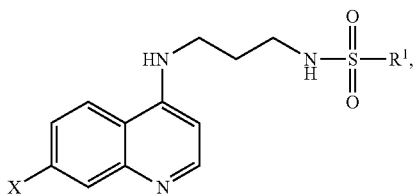

(IB)

wherein

X is halo, hydroxy, $C_{1-6}$alkyl, $C_{2-6}$alkenyl, $C_{2-6}$alkynyl, $C_{1-6}$haloalkyl, $C_{1-6}$alkoxy, $C_{6-14}$aryl, heteroaryl, heterocyclyl, $C_{3-10}$cycloalkyl or $C_{3-10}$cycloalkenyl, wherein the latter 10 moieties are optionally substituted with one or more of:
1. halo;
2. hydroxy;
3. $C_{1-6}$alkyl;
4. $C_{2-6}$alkenyl;
5. $C_{2-6}$alkynyl;
6. $C_{1-6}$haloalkyl;
7. $C_{1-6}$alkoxy;
8. nitro;
9. —C(O)O—$C_{1-10}$alkyl;
10. —C(O)O—$C_{6-14}$aryl;
11. $C_{6-14}$aryl, optionally substituted with one or more of halo or $C_{1-6}$alkyl; or
12. —NR$^8$R$^9$, wherein R$^8$ and R$^9$ are each individually selected from H and $C_{1-6}$alkyl; and R$^1$ is $C_{1-6}$alkyl, $C_{2-6}$alkenyl, $C_{2-6}$alkynyl, $C_{6-14}$aryl, heteroaryl, heterocyclyl, $C_{3-10}$cycloalkyl or $C_{3-10}$cycloalkenyl, each of which is optionally substituted with one or more of:
1. halo;
2. hydroxy;
3. nitro;
4. $C_{1-6}$alkyl;
5. $C_{2-6}$alkenyl;
6. $C_{2-6}$alkynyl;
7. $C_{1-6}$haloalkyl;
8. $C_{1-6}$alkoxy;
9. —C(O)O—$C_{1-6}$alkyl;
10. —C(O)O—$C_{6-14}$aryl;
11. $C_{6-14}$aryl, optionally substituted with halo or $C_{1-6}$alkyl;
12. heteroaryl, optionally substituted with halo or $C_{1-6}$alkyl; or
13. —NR$^8$R$^9$, wherein R$^8$ and R$^9$ are each individually selected from H and $C_{1-6}$alkyl, or a pharmaceutically acceptable salt, solvate or prodrug thereof,
with the proviso that the compound is not 5-Dimethylamino-naphthalene-1-sulfonic acid [3-(7-chloro-quinolin-4-ylamino)-propyl]-amide.

In another aspect, the disclosure relates to the compound 7-chloro-4-(4-(2,4-dinitrophenylsulfonyl)piperazin-1yl)quinoline, or a pharmaceutically acceptable salt, solvate or prodrug thereof.

In another aspect, the disclosure relates to the compound methyl 3-(4-(7-chloroquinolin-4-yl)piperazin-1-ylsulfonyl) thiophene-2carboxylate, or a pharmaceutically acceptable salt, solvate or prodrug thereof.

In another aspect, the disclosure relates to the compound 7-chloro-4-(4-(biphenylsulfonyl)piperazin-1 yl)quinoline, or a pharmaceutically acceptable salt, solvate or prodrug thereof.

In another aspect, the disclosure relates to the compound 5-(4-(7-chloroquinolin-4-yl)piperazin-1-ylsulfonyl)-N,N-dimethylnaphthalen-1-amine, or a pharmaceutically acceptable salt, solvate or prodrug thereof.

In another aspect, the disclosure relates to the compound 7-chloro-4-(4-(2,4-dichlorophenylsulfonyl)piperazin-1yl) quinoline, or a pharmaceutically acceptable salt, solvate or prodrug thereof.

In another aspect, the disclosure relates to the compound 4-[4-(3-nitro-benzenesulfonyl)-piperazin-1-yl]-7-trifluoromethylquinoline, or a pharmaceutically acceptable salt, solvate or prodrug thereof.

In another aspect, the disclosure relates to the compound 4-[4-(4-chloro-benzenesulfonyl)-piperazin-1-yl]-7-trifluoromethylquinoline, or a pharmaceutically acceptable salt, solvate or prodrug thereof.

In another aspect, the disclosure relates to the compound 4-[4-(toluene-4-sulfonyl)piperazin-1-yl]-7-trifluoromethylquinoline, or a pharmaceutically acceptable salt, solvate or prodrug thereof.

In another aspect, the disclosure relates to the compound 4-[4-(biphenyl-4-sulfonyl)-piperazin-1-yl]-7-trifluoromethylquinoline, or a pharmaceutically acceptable salt, solvate or prodrug thereof.

In another aspect, the disclosure relates to the compound 4-[4-(2,4-dichloro-benzenesulfonyl)-piperazin-1-yl]-7-trifluoromethyl-quinoline, or a pharmaceutically acceptable salt, solvate or prodrug thereof.

In another aspect, the disclosure relates to the compound 4-(4-methanesulfonyl-piperazin-1-yl)-7-trifluoromethyl-quinoline, or a pharmaceutically acceptable salt, solvate or prodrug thereof.

In another aspect, the disclosure relates to the compound 4-[4-(2,4-dinitro-benzenesulfonyl)-piperazin-1-yl]-7-trifluoromethyl-quinoline, or a pharmaceutically acceptable salt, solvate or prodrug thereof.

In another aspect, the disclosure relates to the compound dimethyl-{5-[4-(7-trifluoromethyl-quinolin-4-yl)piperazine-1-sulfonyl]-naphthalen-1-yl}-amine, or a pharmaceutically acceptable salt, solvate or prodrug thereof.

In another aspect, the disclosure relates to the compound 3-[4-(7-trifluoromethyl-quinolin-4-yl)-piperazine-1-sulfonyl]thiophene-2-carboxylic acid methyl ester, or a pharmaceutically acceptable salt, solvate or prodrug thereof.

In another aspect, the disclosure relates to the compound N-[3-(7-chloro-quinolin-4-ylamino)-propyl]-methane sulfonamide, or a pharmaceutically acceptable salt, solvate or prodrug thereof.

In another aspect, the disclosure relates to the compound N-[3-(7-chloro-quinolin-4-ylamino)-propyl]-4-methylbenzenesulfonamide, or a pharmaceutically acceptable salt, solvate or prodrug thereof.

In another aspect, the disclosure relates to the compound N-[3-(7-chloro-quinolin-4-ylamino)-propyl]-2,4-dinitrobenzenesulfonamide, or a pharmaceutically acceptable salt, solvate or prodrug thereof.

In another aspect, the disclosure relates to the compound N-(3-(7-chloroquinolin-4-ylamino)propyl)-3 nitrobenzene sulfonamide, or a pharmaceutically acceptable salt, solvate or prodrug thereof.

In another aspect, the disclosure relates to the compound 4-chloro-N-(3-(7-chloroquinolin-4-ylamino) propyl)benzene sulfonamide, or a pharmaceutically acceptable salt, solvate or prodrug thereof.

In another aspect, the disclosure relates to the compound biphenyl-4-sulfonic acid [3-(7-chloro-quinolin-4-ylamino)-propyl]amide, or a pharmaceutically acceptable salt, solvate or prodrug thereof.

In another aspect, the disclosure relates to the compound 2,4-dichloro-N-[3-(7-chloro-quinolin-4-ylamino)-propyl] benzene sulfonamide, or a pharmaceutically acceptable salt, solvate or prodrug thereof.

In another aspect, the disclosure relates to the compound N-(3-(7-chloroquinolin-4-ylamino)propyl)thiophene-3 sulfonamide-2-carbomethoxy ester, or a pharmaceutically acceptable salt, solvate or prodrug thereof.

In another aspect, the disclosure relates to the compound N-[3-(7-trifluoromethyl-quinolin-4-ylamino)-propyl]methane sulfonamide, or a pharmaceutically acceptable salt, solvate or prodrug thereof.

In another aspect, the disclosure relates to the compound 4-methyl-N-[3-(7-trifluoromethyl-quinolin-4-ylamino)-propyl]benzene sulfonamide, or a pharmaceutically acceptable salt, solvate or prodrug thereof.

In another aspect, the disclosure relates to the compound 2,4-dinitro-N-[3-(7-trifluoromethyl-quinolin-4-ylamino) propyl]-benzene sulfonamide, or a pharmaceutically acceptable salt, solvate or prodrug thereof.

In another aspect, the disclosure relates to the compound 3-nitro-N-[3-(7-trifluoromethyl-quinolin-4-ylamino)-propyl]benzene sulfonamide, or a pharmaceutically acceptable salt, solvate or prodrug thereof.

In another aspect, the disclosure relates to the compound 4-chloro-N-[3-(7-trifluoromethyl-quinolin-4-ylamino)-propyl]benzene sulfonamide, or a pharmaceutically acceptable salt, solvate or prodrug thereof.

In another aspect, the disclosure relates to the compound 5-dimethylamino-naphthalene-1-sulfonic acid [3-(7-trifluoromethylquinolin-4-ylamino)-propyl]-amide, or a pharmaceutically acceptable salt, solvate or prodrug thereof.

In another aspect, the disclosure relates to the compound biphenyl-4-sulfonic acid [3-(7-trifluoromethyl-quinolin-4-ylamino)propyl]-amide, or a pharmaceutically acceptable salt, solvate or prodrug thereof.

In another aspect, the disclosure relates to the compound 2,4-dichloro-N-[3-(7-trifluoromethyl-quinolin-4-ylamino) propyl]-benzenesulfonamide, or a pharmaceutically acceptable salt, solvate or prodrug thereof.

In another aspect, the disclosure relates to the compound N-(3-(7-trifluoromethyl-quinolin-4-ylamino) propyl)thiophene-3sulfonamide-2-carbomethoxy ester, or a pharmaceutically acceptable salt, solvate or prodrug thereof.

In another aspect, the disclosure relates to a composition comprising a compound of the disclosure and a pharmaceutically acceptable carrier.

In another aspect, the disclosure relates to use of a compound of the disclosure in the manufacture of a medicament for the treatment of cancer.

In another aspect, the disclosure relates to use of a compound of the disclosure for the treatment of cancer.

In another aspect, the disclosure relates to a composition comprising a compound of the disclosure and a pharmaceutically acceptable carrier, for use in the treatment of cancer.

In another aspect, the disclosure relates to use of 7-chloro-4-(4-(2,4-dinitrophenylsulfonyl)piperazin-1yl) quinoline, or a pharmaceutically acceptable salt, solvate or prodrug thereof, in the manufacture of a medicament for the treatment of cancer.

In another aspect, the disclosure relates to use of 7-chloro-4-(4-(2,4-dinitrophenylsulfonyl)piperazin-1yl) quinoline, or a pharmaceutically acceptable salt, solvate or prodrug thereof, for the treatment of cancer.

In another aspect, the disclosure relates to 7-chloro-4-(4-(2,4-dinitrophenylsulfonyl)piperazin-1yl) quinoline, or a pharmaceutically acceptable salt, solvate or prodrug thereof, for use in the treatment of cancer.

In another aspect, the disclosure relates to a method of treating a subject with cancer, the method comprising administering a compound of the disclosure to the subject.

In another aspect, the disclosure relates to a method of treating a subject with cancer, the method comprising administering to the subject a compound of the disclosure in combination with an anti-cancer agent.

In another aspect, the disclosure relates to a method of inhibiting a level of proteasome in a cancer cell, the method comprising contacting the cell with a compound of the disclosure.

In another aspect, the disclosure relates to a method of modulating proliferation of a cancer cell, the method comprising contacting the cell with a compound of the disclosure.

In another aspect, the disclosure relates to a method of delaying cell cycle progression of a cancer cell, the method comprising contacting the cell with a compound of the disclosure.

In another aspect, the disclosure relates to a method of inducing apoptosis in a cancer cell, the method comprising contacting the cell with a compound of the disclosure.

In another aspect, the disclosure relates to a method of treating a subject with cancer, the method comprising administering to the subject 7-Chloro-4-(4-tosylpiperazin-1-yl)quinoline, or a pharmaceutically acceptable salt, solvate or prodrug thereof.

In another aspect, the disclosure relates to a method of treating a subject with cancer, the method comprising administering to the subject 7-Chloro-4-(4-(4-chlorophenylsulfonyl)piperazin-1-yl)quinoline, or a pharmaceutically acceptable salt, solvate or prodrug thereof.

In another aspect, the disclosure relates to a method of treating a subject with cancer, the method comprising administering to the subject 7-Chloro-4-(4-(3-nitrophenylsulfonyl)piperazin-1-yl)quinoline, or a pharmaceutically acceptable salt, solvate or prodrug thereof.

In another aspect, the disclosure relates to a method of treating a subject with cancer, the method comprising administering to the subject 5-Dimethylamino-naphthalene-1-sulfonic acid [3-(7-chloro-quinolin-4-ylamino)-propyl]-amide, or a pharmaceutically acceptable salt, solvate or prodrug thereof.

In another aspect, the disclosure relates to a method of inducing aneuploidy in a cancer cell, comprising contacting the cell with a compound of the disclosure.

In another aspect, the disclosure relates to a method of increasing a level of cyclin B and/or cyclin E in a cancer cell, comprising contacting the cell with a compound of the disclosure.

In another aspect, the disclosure relates to a method of inactivating Cdk1 in a cell, comprising contacting the cell with a compound of the disclosure.

In another aspect, the disclosure relates to a method of selectively killing or inhibiting growth and/or proliferation of a cancer cell in a subject, the method comprising administering to the subject the compound 7-chloro-4-(4-(2,4-dinitrophenylsulfonyl)piperazin-1yl)quinoline, 4-(4-Methanesulfonyl-piperazin-1-yl)-7-trifluoromethyl-quinoline, or N-(3-(7-Chloroquinolin-4-ylamino)propyl)thiophene-3-sulfonamide-2-carbomethoxy ester, or a pharmaceutically acceptable salt, solvate or prodrug thereof.

Other aspects and features of the present disclosure will become apparent to those of ordinary skill in the art upon review of the following description of specific embodiments of the disclosure in conjunction with the accompanying tables and figures.

BRIEF DESCRIPTION OF THE DRAWINGS

FIG. 5 shows the toxic effect of VR-23 on MCF10A non-cancer cells, as determined by a clonogenic assay (FIG. 5A), and flow cytometry (FIG. 5B). In this figure, "CQ" refers to chloroquine.

FIG. 12 shows representative images of the effect of VR-23 on cytoskeletal formation (FIG. 12A) and on centrosome amplification (FIG. 12B) in HeLa S3 cells, as determined by microscopy.

FIG. 25 shows the effect of treating ATH490 mice engrafted with MDA-MB231 human metastatic breast cancer cells with VR-23, paclitaxel (Tax) or a combination of VR-23 and paclitaxel on tumor size, in representative images of mice (FIG. 25A) and in graphical representation of the tumor sizes (FIG. 25B) based on the data shown in Table X. In FIG. 25A and FIG. 25B, "Tax" refers to paclitaxel.

DETAILED DESCRIPTION

I. Definitions

Figures 1A, 1B:
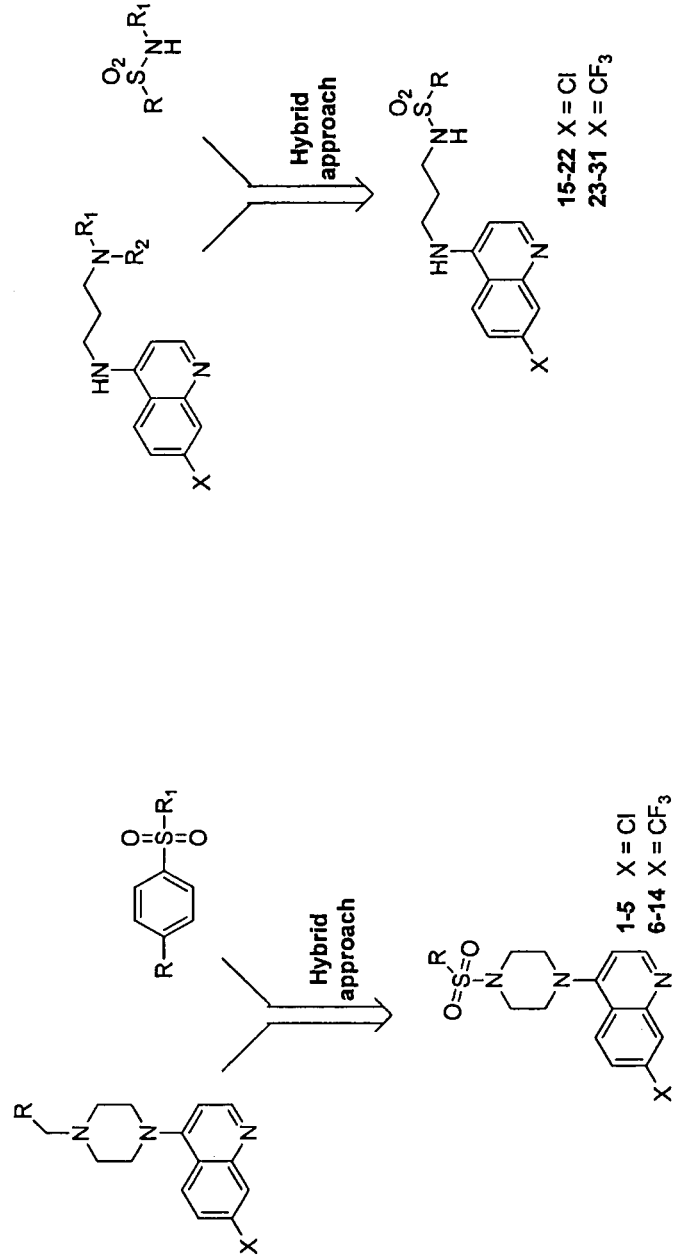
FIG. 1 shows schemes for the design and synthesis of 4-piperazinylquinoline derived sulfonyl analogs (FIG. 1A) and 4-aminoquinoline derived sulfonamide compounds (FIG. 1B).
Figure 2:
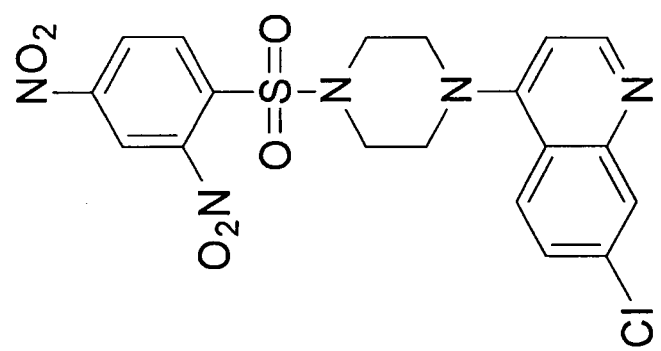
FIG. 2 shows the chemical structure of 7-Chloro-4-(4-(2,4-dinitrophenylsulfonyl)piperazin-1-yl)quinoline (i.e. VR-23).

Unless otherwise indicated, the definitions and embodiments described in this and other sections are intended to be applicable to all embodiments and aspects of the present disclosure herein described for which they are suitable as would be understood by a person skilled in the art.

Unless defined otherwise all technical and scientific terms used herein have the same meaning as commonly understood to one of ordinary skill in the art to which the present disclosure belongs.

The term "compound of the disclosure" or "compound of the present disclosure" and the like as used herein refers to a compound of Formula (I) or a pharmaceutically acceptable salt, solvate and/or prodrug thereof. The term "composition of the disclosure" or "composition of the present disclosure" and the like as used herein refers to a composition comprising a compound of the disclosure and at least one additional component, for example, a suitable carrier.

As used in the present disclosure, the singular forms "a," "an," and "the" include plural reference unless the context clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "about" and "approximately" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

The term "alkyl" as used herein, whether it is used alone or as part of another group, means straight or branched chain, saturated alkyl groups. The term $C_{1-6}$alkyl means an alkyl group having 1, 2, 3, 4, 5, or 6 carbon atoms.

The term "haloalkyl" as used herein refers to an alkyl group wherein one or more, including all of the hydrogen atoms are replaced by a halogen atom. In an embodiment, the halogen is a fluorine, in which case the haloalkyl may be referred to herein as a "fluoroalkyl" group. It is an embodiment that all of the hydrogen atoms are replaced by fluorine atoms. For example, the haloalkyl group can be trifluoromethyl, pentafluoroethyl and the like. It is an embodiment that the haloalkyl group is trifluoromethyl.

The term "alkenyl" as used herein, whether it is used alone or as part of another group, means straight or branched chain, unsaturated alkenyl groups. The term $C_{2-6}$alkenyl means an alkenyl group having 2, 3, 4, 5, or 6 carbon atoms and at least one double bond. It is an embodiment of the disclosure that, in the alkenyl groups, one or more, including all, of the hydrogen atoms are optionally replaced with F and thus include, for example trifluoroethenyl, pentafluoropropenyl and the like.

The term "alkynyl" as used herein, whether it is used alone or as part of another group, means straight or branched chain, unsaturated alkynyl groups. The term $C_{2-6}$alkynyl means an alkynyl group having 2, 3, 4, 5, or 6 carbon atoms and at least one triple bond.

The term "cycloalkyl" as used herein, whether it is used alone or as part of another group, means saturated alkyl groups having at least one cyclic ring. The term $C_{3-10}$cycloalkyl means a cycloalkyl group having 3, 4, 5, 6, 7, 8, 9 or 10 carbon atoms.

The term "cycloalkenyl" as used herein, whether it is used alone or as part of another group, means cyclic, unsaturated alkyl groups. The term $C_{3-10}$cycloalkenyl means a cycloalkenyl group having 3, 4, 5, 6, 7, 8, 9 or 10 carbon atoms and at least one double bond.

The term "heteroaryl" as used herein refers to aromatic cyclic or polycyclic ring systems having at least one heteroatom chosen from N, O and S and at least one aromatic ring. Examples of heteroaryl groups include, without limitation, furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl and quinazolinyl, among others.

The term "heterocyclyl" as used herein includes non-aromatic rings or ring systems that contain at least one ring having at least one heteroatom (such as nitrogen, oxygen or sulfur). For example, the heterocyclyl groups include all of the fully saturated and partially unsaturated derivatives of the above-mentioned heteroaryl groups. Examples of heterocyclic groups include, without limitation, pyrrolidinyl, tetrahydrofuranyl, morpholinyl, thiomorpholinyl, piperidinyl, piperazinyl, thiazolidinyl, isothiazolidinyl, and imidazolidinyl. In embodiments of the present disclosure, the heterocyclyl group is piperazinyl.

The term "alkylene" as used herein means straight or branched chain, saturated alkylene group, that is, a saturated carbon chain that contains substituents on two of its ends. The term $C_{1-10}$alkylene means an alkylene group having 1, 2, 3, 4, 5, 6, 7, 8, 9 or 10 carbon atoms.

The term "alkenylene" as used herein means straight or branched chain, unsaturated alkenylene group, that is, an unsaturated carbon chain that contains substituents on two of its ends. The term $C_{2-10}$alkenylene means an alkenylene group having 2, 3, 4, 5, 6, 7, 8, 9 or 10 carbon atoms and at least 1, for example 1-4, 1-3, 1-2 or 1 double bonds.

The term "aryl" as used herein refers to cyclic groups that contain at least one aromatic ring, for example a single ring (e.g. phenyl) or multiple condensed rings (e.g. naphthyl). In an embodiment of the present disclosure, the aryl group contains 6, 9, 10 or 14 atoms such as phenyl, naphthyl, indanyl or anthracenyl.

As used herein, the term "amino" refers to the group —NH$_2$.

The term "halo" as used herein refers to a halogen atom and includes fluorine (F), chlorine (Cl), bromine (Br) and iodine (I). It is an embodiment that the halo group is a chloro group.

As used herein, "hydroxy" refers to the group —OH.

The term "alkoxy" as used herein refers to the group "alkyl-O—". The term "$C_{1-6}$alkoxy" means an alkoxy group having 1, 2, 3, 4, 5 or 6 carbon atoms bonded to the oxygen atom of the alkoxy group.

As used herein, "nitro" refers to the group —NO$_2$.

The term "VR-23" as used herein, refers to the compound 7-chloro-4-)4-(2,4-dinitrophenylsulfonyl)piperazin-1-yl) quinoline:

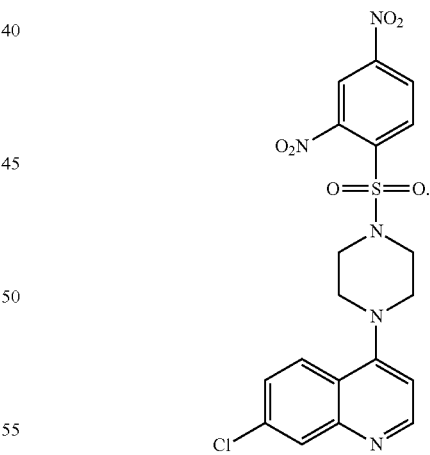

The term "cell" as used herein refers to, for example, a single cell or a plurality of cells.

As used herein, a "subject" refers to all members of the animal kingdom including mammals, and suitably refers to humans. A member of the animal kingdom includes, without limitation, a mammal (such as a human, primate, swine, sheep, cow, equine, horse, camel, canine, dog, feline, cat, tiger, leopard, civet, mink, stone marten, ferret, house pet, livestock, rabbit, mouse, rat, guinea pig or other rodent, seal, whale and the like), fish, amphibian, reptile, and bird (such as water fowl, migratory bird, quail, duck, goose, poultry, or chicken). In an embodiment of the present disclosure, the subject is in need of a compound or composition of the disclosure.

The term "pharmaceutically acceptable" as used herein means compatible with the treatment of subjects, for example, humans.

The term "pharmaceutically acceptable salt" refers, for example, to a salt that retains the desired biological activity of a compound of the present disclosure and does not impart undesired toxicological effects thereto; and may refer to an acid addition salt or a base addition salt.

The term "acid addition salt" as used herein means any non-toxic organic or inorganic salt of any basic compound. Basic compounds that form an acid addition salts include, for example, compounds comprising an amine. For example, an acid addition salt includes any non-toxic organic or inorganic salt of any basic compound of the present disclosure, for example the exemplary compounds disclosed in Table I and the compounds of Table II. Inorganic acids that may form suitable salts include, without limitation, hydrochloric, hydrobromic, sulfuric and phosphoric acids, as well as metal salts such as sodium monohydrogen orthophosphate and potassium hydrogen sulfate. Organic acids that may form suitable salts include, without limitation, mono-, di-, or tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono- or di-acid salts may be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to a person skilled in the art.

The term "base addition salt" as used herein means any non-toxic organic or inorganic base addition salt of any acidic compound. Acidic compounds that form a base addition salt include, for example, compounds comprising a carboxylic acid group. For example, a base addition salt includes any non-toxic organic or inorganic base addition salt of any acidic compound of the present disclosure. Inorganic bases that may form suitable salts include, without limitation, lithium, sodium, potassium, calcium, magnesium or barium hydroxide. Organic bases that may form suitable salts include, without limitation, aliphatic, alicyclic or aromatic organic amines such as methylamine, trimethylamine and picoline or ammonia. The selection of the appropriate salt will be known to a person skilled in the art.

Those of ordinary skill in the art will recognize further pharmaceutically acceptable salts for the compounds provided herein. In general, a pharmaceutically acceptable acid addition salt or base addition salt is synthesized from a parent compound that contains a basic or acidic moiety by any conventional chemical method. For example, a neutral compound is treated with an acid or a base in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

In embodiments of the present disclosure, the compounds described herein have at least one asymmetric center. These compounds exist as enantiomers. Where compounds possess more than one asymmetric center, they may exist as diastereomers. It is to be understood that all such isomers and mixtures thereof in any proportion are encompassed within the scope of the present disclosure. It is to be further understood that while the stereochemistry of the compounds may be as shown in any given compound listed herein, such compounds may also contain certain amounts (e.g. less than 20%, suitably less than 10%, more suitably less than 5%) of compounds of the disclosure having alternate stereochemistry. For example, compounds of the disclosure that are shown without any stereochemical designations are understood to be racemic mixtures (i.e. contain and equal amount of each possible enantiomer or diastereomer). However, it is to be understood that all enantiomers and diastereomers are included within the scope of the present disclosure, including mixtures thereof in any proportion.

As used herein, the term "prodrug" refers to a substance that is prepared in an inactive form that is converted to an active form (i.e., drug) within the body or cells thereof by the action of, for example, endogenous enzymes or other chemicals and/or conditions. Prodrug derivatives of the compounds of Formula (I), or pharmaceutically acceptable salts or solvates thereof, can be prepared by methods known to those of ordinary skill in the art. For example, prodrugs of the compounds of the present disclosure may be, for example, conventional esters formed with available amino groups. For example, available amino groups may be acylated using an activated acid in the presence of a base, and optionally, in inert solvent (e.g. an acid chloride in pyridine).

As used herein, the term "therapeutic agent" refers to any compound or composition useful in the treatment of a disease, a disorder or a disease condition to which the compound of the present disclosure is directed, other than a compound of the present disclosure. For example, in various embodiments, the therapeutic agent is directed to the same, or to a different, target from the target of a compound of the present disclosure. In other embodiments, the therapeutic agent is (a) any agent that can arrest cell cycle progression at G2/M phase; (b) any DNA or cell damaging agent that can activate G2/M checkpoint; or (c) ionizing radiation. Exemplary therapeutic agents include, without limitation, an anti-cancer agent and a carcinostatic agent. Non-limiting examples of anti-cancer agents include bortezomib, paclitaxel, monastrol, vinca, VX-680, ZM447439, hesperidin, temozolomide, nocodazole, and signal transduction inhibitors, such as bevacizumab, cetuximab, geftinib, trastumab, tipifarnib, CCI-779, Ly294002, Sunitinib maleate, API-1, and Akt1/2 inhibitor.

As used herein, the terms "treating" or "treatment" and the like refer to an approach for obtaining beneficial or desired results, including clinical results. Beneficial or desired clinical results may include, without limitation, alleviation or amelioration of one or more symptoms or conditions, diminishment of extent of disease, stabilization (i.e. not worsening) of the state of disease, prevention of development of disease, prevention of spread of disease, delay or slowing of disease progression, delay or slowing of disease onset or progression, amelioration or palliation of the disease state, diminishment of the reoccurrence of disease and remission (whether partial or total), whether detectable or undetectable. "Treating" or "treatment" may also refer to prolonging survival of a subject as compared to that expected in the absence of treatment. "Treating" or "treatment" may also refer to inhibiting the progression of disease, slowing the progression of disease temporarily or halting the progression of the disease permanently. "Treating" and "treatment" as used herein also include prophylactic treatment. For example, a subject with early stage cancer can be treated to prevent progression, or alternatively a subject in remission can be treated with a compound or composition described herein to prevent recurrence.

Treatment methods comprise, for example administering to a subject a therapeutically effective amount of one or more of the compounds of the disclosure and optionally consists of a single administration, or alternatively comprises a series of administrations. For example, the compounds of the present disclosure may be administered at least once a week. However, in another embodiment, the compounds of the present disclosure may be administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, the age of the patient, the concentration, the activity of the compounds of the present disclosure, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. For example, the compounds are administered to the subject in an amount and for a duration sufficient to treat the subject.

The term "administered" as used herein means administration of a therapeutically effective dose of a compound or composition of the disclosure to a cell either in cell culture or in a subject.

The term "effective amount" or "therapeutically effective amount" as used herein means an amount effective, at dosages and for periods of time necessary to achieve the desired result. For example in the context of treating a subject with cancer, an effective amount is an amount that, for example, reduces the tumor volume compared to the tumor volume without administration of the compound of the present disclosure. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

As used herein, the terms "modulating" or "modulate" and the like mean to affect or change a system in some way, e.g. by delaying, stopping, or speeding up. In various embodiments, the cell cycle progression of a cell may be delayed by contacting the cell with a compound of the disclosure.

II. Compounds and Compositions of the Disclosure

In one aspect, the disclosure relates to a compound of Formula (I):

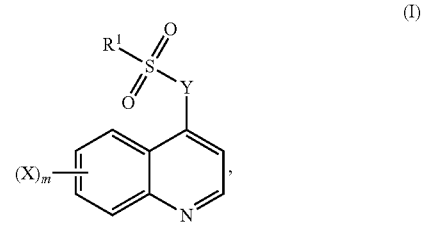

wherein,

X is halo, hydroxy, $C_{1-6}$alkyl, $C_{2-6}$alkenyl, $C_{2-6}$alkynyl, $C_{1-6}$haloalkyl, $C_{1-6}$alkoxy, $C_{6-14}$aryl, heteroaryl, heterocyclyl, $C_{3-10}$cycloalkyl or $C_{3-10}$cycloalkenyl, wherein the latter 10 moieties are optionally substituted with one or more of:
1. halo;
2. hydroxy;
3. $C_{1-6}$alkyl;
4. $C_{2-6}$alkenyl;
5. $C_{2-6}$alkynyl;
6. $C_{1-6}$haloalkyl;
7. $C_{1-6}$alkoxy;
8. nitro;
9. —C(O)O—$C_{1-10}$alkyl;
10. —C(O)O—$C_{6-14}$aryl;
11. $C_{6-14}$aryl, optionally substituted with one or more of halo or $C_{1-6}$alkyl; or
12. —NR$^8$R$^9$, wherein R$^8$ and R$^9$ are each individually selected from H and $C_{1-6}$alkyl;

m is 0, 1, or 2;

Y is —N(R)$C_{1-10}$alkyleneN(R)—, —N(R)$C_{2-10}$alkenyleneN(R)—, —N(R)heterocyclylN(R)—, —N(R)$C_{6-14}$arylN(R)—, —N(R)heteroarylN(R)—, —N(R)$C_{3-10}$cycloalkylN(R)—, —N(R)$C_{3-10}$cycloalkenylN(R)—, or

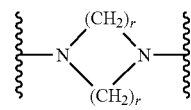

each of which are optionally substituted with one or two substituents selected from amino, halo and $C_{1-6}$alkyl;
wherein each r is independently or simultaneously 1, 2 or 3; each R is independently or simultaneously H or $C_{1-6}$alkyl; and
R$^1$ is $C_{1-6}$alkyl, $C_{2-6}$alkenyl, $C_{2-6}$alkynyl, $C_{6-14}$aryl, heteroaryl, heterocyclyl, $C_{3-10}$cycloalkyl or $C_{3-10}$cycloalkenyl, each of which is optionally substituted with one or more of:
1. halo;
2. hydroxy;
3. nitro;
4. $C_{1-6}$alkyl;
5. $C_{2-6}$alkenyl;
6. $C_{2-6}$alkynyl;
7. $C_{1-6}$haloalkyl;
8. $C_{1-6}$alkoxy;
9. —C(O)O—$C_{1-6}$alkyl;
10. —C(O)O—$C_{6-14}$aryl;
11. $C_{6-14}$aryl, optionally substituted with halo or $C_{1-6}$alkyl;
12. heteroaryl, optionally substituted with halo or $C_{1-6}$alkyl; or
13. —NR$^8$R$^9$, wherein R$^8$ and R$^9$ are each individually selected from H and $C_{1-6}$alkyl, or a pharmaceutically acceptable salt, solvate or prodrug thereof,
with the proviso that the compound is not:
7-Chloro-4-(4-tosylpiperazin-1-yl)quinoline,
7-Chloro-4-(4-(4-chlorophenylsulfonyl)piperazin-1-yl)quinoline,
7-Chloro-4-(4-(3-nitrophenylsulfonyl)piperazin-1-yl)quinoline, or
5-Dimethylamino-naphthalene-1-sulfonic acid [3-(7-chloroquinolin-4-ylamino)-propyl]-amide.

In an embodiment, the $C_{1-6}$alkyl, $C_{2-6}$alkenyl, $C_{2-6}$alkynyl, $C_{1-6}$haloalkyl, $C_{1-6}$alkoxy, $C_{6-14}$aryl, heteroaryl, heterocyclyl, $C_{3-10}$cycloalkyl or $C_{3-10}$cycloalkenyl of X is mono-, di-, tri- or tetra-substituted.

In another embodiment, the $C_{1-6}$alkyl, $C_{2-6}$alkenyl, $C_{2-6}$alkynyl, $C_{6-14}$aryl, heteroaryl, heterocyclyl, $C_{3-10}$cycloalkyl or $C_{3-10}$cycloalkenyl of $R^1$ is mono-, di-, tri- or tetra-substituted.

In an embodiment, m is 1.

In one embodiment, X is halo, hydroxy, $C_{1-6}$alkyl, $C_{2-6}$alkenyl, $C_{2-6}$alkynyl, $C_{1-6}$haloalkyl or $C_{1-6}$alkoxy. In another embodiment, X is halo, hydroxy, $C_{1-4}$alkyl, $C_{2-4}$alkenyl, $C_{2-4}$alkynyl, $C_{1-4}$haloalkyl or $C_{1-4}$alkoxy. In a further embodiment, X is halo, hydroxy, $C_{1-4}$alkyl, or $C_{1-4}$haloalkyl. In an embodiment of the present disclosure, X is halo or $C_{1-4}$haloalkyl. In another embodiment, X is halo. It is an embodiment that X is Cl. In another embodiment, X is $C_{1-6}$fluoroalkyl. It is an embodiment that X is —$CF_3$.

In one embodiment, the substituents on the group X are selected from halo, hydroxy, $C_{1-6}$alkyl, $C_{2-6}$alkenyl, $C_{2-6}$alkynyl, $C_{1-6}$haloalkyl, $C_{1-6}$alkoxy, and nitro. In another embodiment, the substituents on the group X are selected from halo, hydroxy, $C_{1-6}$alkyl, and $C_{1-6}$haloalkyl.

In another embodiment of the present disclosure, Y is —N(R)$C_{1-10}$alkyleneN(R)—, —N(R)$C_{2-10}$alkenyleneN(R)—, —N(R)$C_{3-10}$cycloalkyl N(R)— or

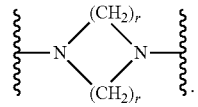

In another embodiment, Y is —N(R)$C_{1-10}$alkyleneN(R)—, or

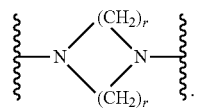

In a further embodiment, Y is —NH$C_{1-6}$alkyleneNH—. It is an embodiment that Y is —NH(CH$_2$)$_3$NH—.

In another embodiment, Y is

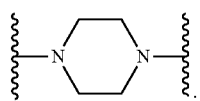

In another embodiment, r is independently or simultaneously 1 or 2, optionally 2.

In another embodiment, R is independently or simultaneously H or $C_{1-4}$alkyl. In one embodiment, R is independently or simultaneously H or $CH_3$. In one embodiment, R is H.

In an embodiment, $R^1$ is $C_{1-4}$alkyl, $C_{2-4}$alkenyl, $C_{2-4}$alkynyl, $C_{6-10}$aryl, heteroaryl, heterocyclyl, $C_{3-6}$cycloalkyl or $C_{3-6}$cycloalkenyl, each of which is optionally substituted with one or more of:
1. halo;
2. hydroxy;
3. nitro;
4. $C_{1-4}$alkyl;
5. $C_{2-4}$alkenyl;
6. $C_{2-4}$alkynyl;
7. $C_{1-4}$haloalkyl;
8. $C_{1-4}$alkoxy;
9. —C(O)O—$C_{1-4}$alkyl;
10. —C(O)O—$C_{6-10}$aryl;
11. $C_{6-10}$aryl, optionally substituted with halo or $C_{1-4}$alkyl;
12. heteroaryl, optionally substituted with halo or $C_{1-4}$alkyl; or
13. —NR$^8$R$^9$, wherein R$^8$ and R$^9$ are each individually selected from H and $C_{1-4}$alkyl.

In another embodiment, $R^1$ is $C_{1-4}$alkyl, phenyl, naphthyl or thiophenyl, optionally substituted with one or more of:
1. halo;
2. nitro;
3. $C_{1-4}$alkyl;
4. phenyl;
5. —C(O)O—$C_{1-4}$alkyl; or
6. —NR$^8$R$^9$, wherein R$^8$ and R$^9$ are each individually selected from $C_{1-4}$alkyl. In one embodiment, when $R^1$ is phenyl, the phenyl group is ortho-substituted, para-substituted, or ortho,para-disubstituted.

In a further embodiment, $R^1$ is methyl, phenyl, naphthyl or thiophenyl, optionally substituted with one or more of chloro, nitro, methyl, phenyl, —C(O)O—$CH_3$ or —N(CH$_3$)$_2$. It is an embodiment that $R^1$ is selected from the group consisting of 2,4-dinitrophenyl, thiophenyl-2-carboxylic acid methyl ester, biphenyl, N,N-dimethylnaphthalenyl, 2,4-dichlorophenyl, 3-nitrophenyl, 4-chlorophenyl, tolyl, methyl, and 2-Carbomethoxy-3-thiophenyl.

In a further embodiment, $R^1$ is selected from the group consisting of:

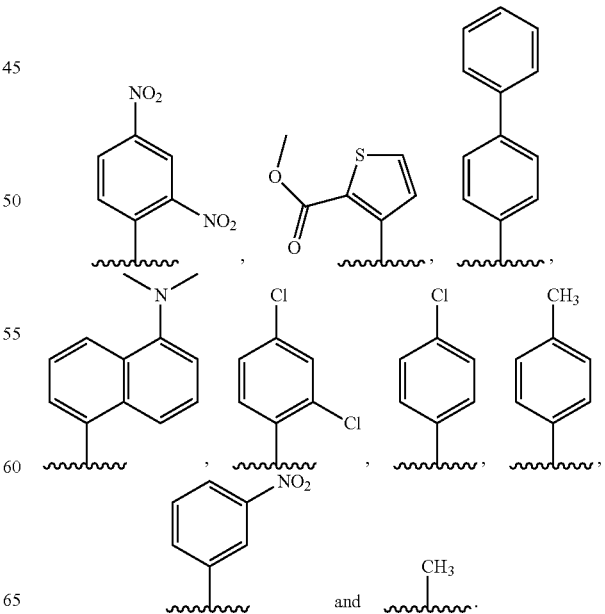

In another embodiment, $R^1$ is:

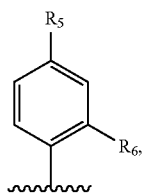

wherein
$R^5$ and $R^6$ are each independently selected from H, halo, hydroxy, nitro, $C_{1-6}$alkyl, $C_{2-6}$alkenyl, $C_{2-6}$alkynyl, $C_{1-6}$haloalkyl, $C_{1-6}$alkoxy, —C(O)O—$C_{1-6}$alkyl, —C(O)O—$C_{6-14}$aryl, $C_{6-14}$aryl, optionally substituted with halo or $C_{1-6}$alkyl, heteroaryl and —$NR^8R^9$, wherein $R^8$ and $R^9$ are each individually selected from H and $C_{1-6}$alkyl.

In an embodiment, $R^5$ and $R^6$ are each independently selected from H, halo, nitro, $C_{1-4}$alkyl and $C_{6-10}$aryl. In another embodiment, $R^5$ and $R^6$ are each independently selected from H, chloro, nitro, methyl and phenyl. In an embodiment, $R^5$ is halo, nitro, $C_{1-4}$alkyl or $C_{6-10}$aryl. In another embodiment, $R^5$ is chloro, nitro, methyl or phenyl. In an embodiment, $R^6$ is H, halo, nitro or $C_{1-4}$alkyl. In another embodiment, $R^6$ is H, chloro or nitro.

In an embodiment, $R^5$ and $R^6$ are both nitro.

In an embodiment, $R^8$ and $R^9$ are each individually selected from H and $C_{1-4}$alkyl. In another embodiment, $R^8$ and $R^9$ are each individually selected from $C_{1-4}$alkyl. In another embodiment, $R^8$ and $R^9$ are both —$CH_3$.

In an embodiment, the compound of Formula (I) is a compound of Formula (IA):

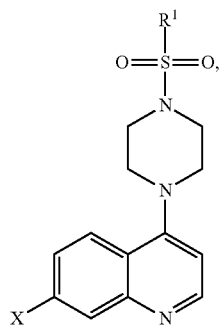

(IA)

wherein
X is halo, hydroxy, $C_{1-6}$alkyl, $C_{2-6}$alkenyl, $C_{2-6}$alkynyl, $C_{1-6}$haloalkyl, $C_{1-6}$alkoxy, $C_{6-14}$aryl, heteroaryl, heterocyclyl, $C_{3-10}$cycloalkyl or $C_{3-10}$cycloalkenyl, wherein the latter 10 moieties are optionally substituted with one or more of:
1. halo;
2. hydroxy;
3. $C_{1-6}$alkyl;
4. $C_{2-6}$alkenyl;
5. $C_{2-6}$alkynyl;
6. $C_{1-6}$haloalkyl;
7. $C_{1-6}$alkoxy;
8. nitro;
9. —C(O)O—$C_{1-10}$alkyl;
10. —C(O)O—$C_{6-14}$aryl;
11. $C_{6-14}$aryl, optionally substituted with one or more of halo or $C_{1-6}$alkyl; or
12. —$NR^8R^9$, wherein $R^8$ and $R^9$ are each individually selected from H and $C_{1-6}$alkyl; and $R^1$ is $C_{1-6}$alkyl, $C_{2-6}$alkenyl, $C_{2-6}$alkynyl, $C_{6-14}$aryl, heteroaryl, heterocyclyl, $C_{3-10}$cycloalkyl or $C_{3-10}$cycloalkenyl, each of which is optionally substituted with one or more of:
1. halo;
2. hydroxy;
3. nitro;
4. $C_{1-6}$alkyl;
5. $C_{2-6}$alkenyl;
6. $C_{2-6}$alkynyl;
7. $C_{1-6}$haloalkyl;
8. $C_{1-6}$alkoxy;
9. —C(O)O—$C_{1-6}$alkyl;
10. —C(O)O—$C_{6-14}$aryl;
11. $C_{6-14}$aryl, optionally substituted with halo or $C_{1-6}$alkyl;
12. heteroaryl, optionally substituted with halo or $C_{1-6}$alkyl; or
13. —$NR^8R^9$, wherein $R^8$ and $R^9$ are each individually selected from H and $C_{1-6}$alkyl, or a pharmaceutically acceptable salt, solvate or prodrug thereof,
with the proviso that the compound is not:
7-Chloro-4-(4-tosylpiperazin-1-yl)quinoline,
7-Chloro-4-(4-(4-chlorophenylsulfonyl)piperazin-1-yl)quinoline, or
7-Chloro-4-(4-(3-nitrophenylsulfonyl)piperazin-1-yl)quinoline.

In an embodiment, the $C_{1-6}$alkyl, $C_{2-6}$alkenyl, $C_{2-6}$alkynyl, $C_{1-6}$haloalkyl, $C_{1-6}$alkoxy, $C_{6-14}$aryl, heteroaryl, heterocyclyl, $C_{3-10}$cycloalkyl or $C_{3-10}$cycloalkenyl of X is mono-, di-, tri- or tetra-substituted.

In another embodiment, the $C_{1-6}$alkyl, $C_{2-6}$alkenyl, $C_{2-6}$alkynyl, $C_{6-14}$aryl, heteroaryl, heterocyclyl, $C_{3-10}$cycloalkyl or $C_{3-10}$cycloalkenyl of $R^1$ is mono-, di-, tri- or tetra-substituted.

In an embodiment, X is halo, hydroxy, $C_{1-6}$alkyl, $C_{2-6}$alkenyl, $C_{2-6}$alkynyl, $C_{1-6}$haloalkyl or $C_{1-6}$alkoxy. In another embodiment, X is halo, hydroxy, $C_{1-4}$alkyl, $C_{2-4}$alkenyl, $C_{2-4}$alkynyl, $C_{1-4}$haloalkyl or $C_{1-4}$alkoxy. In a further embodiment, X is halo, hydroxy, $C_{1-4}$alkyl, or $C_{1-4}$haloalkyl. In an embodiment of the present disclosure, X is halo or $C_{1-4}$haloalkyl. In another embodiment, X is halo. It is an embodiment that X is Cl. In another embodiment, X is $C_{1-6}$fluoroalkyl. It is an embodiment that X is —$CF_3$.

In an embodiment, the substituents on the group X are selected from halo, hydroxy, $C_{1-6}$alkyl, $C_{2-6}$alkenyl, $C_{2-6}$alkynyl, $C_{1-6}$haloalkyl, $C_{1-6}$alkoxy, and nitro. In another embodiment, the substituents on the group X are selected from halo, hydroxy, $C_{1-6}$alkyl, and $C_{1-6}$haloalkyl.

In an embodiment, $R^1$ is $C_{1-4}$alkyl, $C_{2-4}$alkenyl, $C_{2-4}$alkynyl, $C_{6-10}$aryl, heteroaryl, heterocyclyl, $C_{3-6}$cycloalkyl or $C_{3-6}$cycloalkenyl, each of which is optionally substituted with one or more of:
1. halo;
2. hydroxy;
3. nitro;
4. $C_{1-4}$alkyl;
5. $C_{2-4}$alkenyl;
6. $C_{2-4}$alkynyl;
7. $C_{1-4}$haloalkyl;
8. $C_{1-4}$alkoxy;
9. —C(O)O—$C_{1-4}$alkyl;
10. —C(O)O—$C_{6-10}$aryl;
11. $C_{6-10}$aryl, optionally substituted with halo or $C_{1-4}$alkyl;

12. heteroaryl, optionally substituted with halo or $C_{1-4}$alkyl; or
13. —$NR^8R^9$, wherein $R^8$ and $R^9$ are each individually selected from H and $C_{1-4}$alkyl.

In another embodiment, $R^1$ is $C_{1-4}$alkyl, phenyl, naphthyl or thiophenyl, optionally substituted with one or more of:
1. halo;
2. nitro;
3. $C_{1-4}$alkyl;
4. phenyl;
5. —C(O)O—$C_{1-4}$alkyl; or
6. —$NR^8R^9$, wherein $R^8$ and $R^9$ are each individually selected from $C_{1-4}$alkyl. In one embodiment, when $R^1$ is phenyl, the phenyl group is ortho-substituted, para-substituted, or ortho,para-disubstituted.

In a further embodiment, $R^1$ is methyl, phenyl, naphthyl or thiophenyl, optionally substituted with one or more of chloro, nitro, methyl, phenyl, —C(O)O—$CH_3$ or —$N(CH_3)_2$. It is an embodiment that $R^1$ is selected from the group consisting of 2,4-dinitrophenyl, thiophenyl-2-carboxylic acid methyl ester, biphenyl, N,N-dimethylnaphthalenyl, 2,4-dichlorophenyl, 3-nitrophenyl, 4-chlorophenyl, tolyl, methyl, and 2-Carbomethoxy-3-thiophenyl.

In a further embodiment, $R^1$ is selected from the group consisting of:

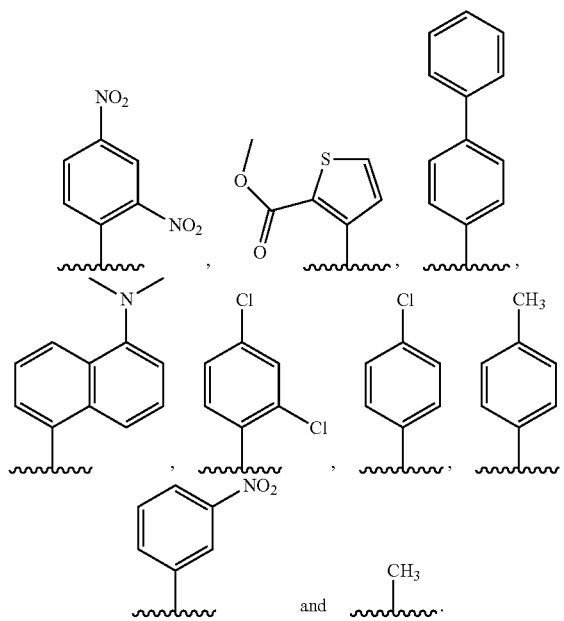

In another embodiment, $R^1$ is:

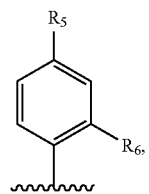

wherein
$R^5$ and $R^6$ are each independently selected from H, halo, hydroxy, nitro, $C_{1-6}$alkyl, $C_{2-6}$alkenyl, $C_{2-6}$alkynyl, $C_{1-6}$haloalkyl, $C_{1-6}$alkoxy, —C(O)O—$C_{1-6}$alkyl, —C(O)O—$C_{6-14}$aryl, $C_{6-14}$aryl, optionally substituted with halo or $C_{1-6}$alkyl, heteroaryl and —$NR^8R^9$, wherein $R^8$ and $R^9$ are each individually selected from H and $C_{1-6}$alkyl.

In an embodiment, $R^5$ and $R^6$ are each independently selected from H, halo, nitro, $C_{1-4}$alkyl and $C_{6-10}$aryl. In another embodiment, $R^5$ and $R^6$ are each independently selected from H, chloro, nitro, methyl and phenyl. In an embodiment, $R^5$ is halo, nitro, $C_{1-4}$alkyl or $C_{6-10}$aryl. In another embodiment, $R^5$ is chloro, nitro, methyl or phenyl. In an embodiment, $R^6$ is H, halo, nitro or $C_{1-4}$alkyl. In another embodiment, $R^6$ is H, chloro or nitro.

In an embodiment, $R^5$ and $R^6$ are both nitro.

In an embodiment, $R^8$ and $R^9$ are each individually selected from H and $C_{1-4}$alkyl. In another embodiment, $R^8$ and $R^9$ are each individually selected from $C_{1-4}$alkyl. In another embodiment, $R^8$ and $R^9$ are both —$CH_3$.

In another embodiment, the compound of Formula (I) is a compound of Formula (IB):

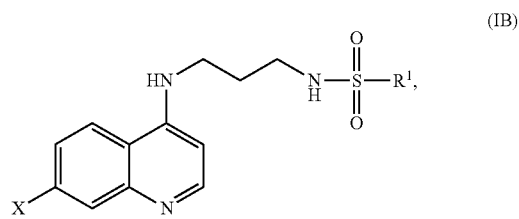

wherein
X is halo, hydroxy, $C_{1-6}$alkyl, $C_{2-6}$alkenyl, $C_{2-6}$alkynyl, $C_{1-6}$haloalkyl, $C_{1-6}$alkoxy, $C_{6-14}$aryl, heteroaryl, heterocyclyl, $C_{3-10}$cycloalkyl or $C_{3-10}$cycloalkenyl, wherein the latter 10 moieties are optionally substituted with one or more of:
1. halo;
2. hydroxy;
3. $C_{1-6}$alkyl;
4. $C_{2-6}$alkenyl;
5. $C_{2-6}$alkynyl;
6. $C_{1-6}$haloalkyl;
7. $C_{1-6}$alkoxy;
8. nitro;
9. —C(O)O—$C_{1-10}$alkyl;
10. —C(O)O—$C_{6-14}$ aryl;
11. $C_{6-14}$aryl, optionally substituted with one or more of halo or $C_{1-6}$alkyl; or
12. —$NR^8R^9$, wherein $R^8$ and $R^9$ are each individually selected from H and $C_{1-6}$alkyl; and
$R^1$ is $C_{1-6}$alkyl, $C_{2-6}$alkenyl, $C_{2-6}$alkynyl, $C_{6-14}$aryl, heteroaryl, heterocyclyl, $C_{3-10}$cycloalkyl or $C_{3-10}$cycloalkenyl, each of which is optionally substituted with one or more of:
1. halo;
2. hydroxy;
3. nitro;
4. $C_{1-6}$alkyl;
5. $C_{2-6}$alkenyl;
6. $C_{2-6}$alkynyl;
7. $C_{1-6}$haloalkyl;
8. $C_{1-6}$alkoxy;
9. —C(O)O—$C_{1-6}$alkyl;
10. —C(O)O—$C_{6-14}$aryl;
11. $C_{6-14}$aryl, optionally substituted with halo or $C_{1-6}$alkyl;
12. heteroaryl, optionally substituted with halo or $C_{1-6}$alkyl; or 13. —NR$^8$R$^9$, wherein R$^8$ and R$^9$ are each individually selected from H and C$_{1-6}$alkyl, or a pharmaceutically acceptable salt, solvate or prodrug thereof, with the proviso that the compound is not 5-Dimethylamino-naphthalene-1-sulfonic acid [3-(7-chloro-quinolin-4-ylamino)-propyl]-amide.

In an embodiment, the C$_{1-6}$alkyl, C$_{2-6}$alkenyl, C$_{2-6}$alkynyl, C$_{1-6}$haloalkyl, C$_{1-6}$alkoxy, C$_{6-14}$aryl, heteroaryl, heterocyclyl, C$_{3-10}$cycloalkyl or C$_{3-10}$cycloalkenyl of X is mono-, di-, tri- or tetra-substituted.

In another embodiment, the C$_{1-6}$alkyl, C$_{2-6}$alkenyl, C$_{2-6}$alkynyl, C$_{6-14}$aryl, heteroaryl, heterocyclyl, C$_{3-10}$cycloalkyl or C$_{3-10}$cycloalkenyl of R$^1$ is mono-, di-, tri- or tetra-substituted.

In an embodiment, X is halo, hydroxy, C$_{1-6}$alkyl, C$_{2-6}$alkenyl, C$_{2-6}$alkynyl, C$_{1-6}$haloalkyl or C$_{1-6}$alkoxy. In another embodiment, X is halo, hydroxy, C$_{1-4}$alkyl, C$_{2-4}$alkenyl, C$_{2-4}$alkynyl, C$_{1-4}$haloalkyl or C$_{1-4}$alkoxy. In a further embodiment, X is halo, hydroxy, C$_{1-4}$alkyl, or C$_{1-4}$haloalkyl. In an embodiment of the present disclosure, X is halo or C$_{1-4}$haloalkyl. In another embodiment, X is halo. It is an embodiment that X is Cl. In another embodiment, X is C$_{1-6}$fluoroalkyl. It is an embodiment that X is —CF$_3$.

In an embodiment, the substituents on the group X are selected from halo, hydroxy, C$_{1-6}$alkyl, C$_{2-6}$alkenyl, C$_{2-6}$alkynyl, C$_{1-6}$haloalkyl, C$_{1-6}$alkoxy, and nitro. In another embodiment, the substituents on the group X are selected from halo, hydroxy, C$_{1-6}$alkyl, and C$_{1-6}$haloalkyl.

In an embodiment, R$^1$ is C$_{1-4}$alkyl, C$_{2-4}$alkenyl, C$_{2-4}$alkynyl, C$_{6-10}$aryl, heteroaryl, heterocyclyl, C$_{3-6}$cycloalkyl or C$_{3-6}$cycloalkenyl, each of which is optionally substituted with one or more of:

1. halo;
2. hydroxy;
3. nitro;
4. C$_{1-4}$alkyl;
5. C$_{2-4}$alkenyl;
6. C$_{2-4}$alkynyl;
7. C$_{1-4}$haloalkyl;
8. C$_{1-4}$alkoxy;
9. —C(O)O—C$_{1-4}$alkyl;
10. —C(O)O—C$_{6-10}$aryl;
11. C$_{6-10}$aryl, optionally substituted with halo or C$_{1-4}$alkyl;
12. heteroaryl, optionally substituted with halo or C$_{1-4}$alkyl; or
13. —NR$^8$R$^9$, wherein R$^8$ and R$^9$ are each individually selected from H and C$_{1-4}$alkyl.

In another embodiment, R$^1$ is C$_{1-4}$alkyl, phenyl, naphthyl or thiophenyl, optionally substituted with one or more of:

1. halo;
2. nitro;
3. C$_{1-4}$alkyl;
4. phenyl;
5. —C(O)O—C$_{1-4}$alkyl; or
6. —NR$^8$R$^9$, wherein R$^8$ and R$^9$ are each individually selected from C$_{1-4}$alkyl. In one embodiment, when R$^1$ is phenyl, the phenyl group is ortho-substituted, para-substituted, or ortho,para-disubstituted.

In a further embodiment, R$^1$ is methyl, phenyl, naphthyl or thiophenyl, optionally substituted with one or more of chloro, nitro, methyl, phenyl, —C(O)O—CH$_3$ or —N(CH$_3$)$_2$. It is an embodiment that R$^1$ is selected from the group consisting of 2,4-dinitrophenyl, thiophenyl-2-carboxylic acid methyl ester, biphenyl, N,N-dimethylnaphthalenyl, 2,4-dichlorophenyl, 3-nitrophenyl, 4-chlorophenyl, tolyl, methyl, and 2-Carbomethoxy-3-thiophenyl.

In a further embodiment, R$^1$ is selected from the group consisting of:

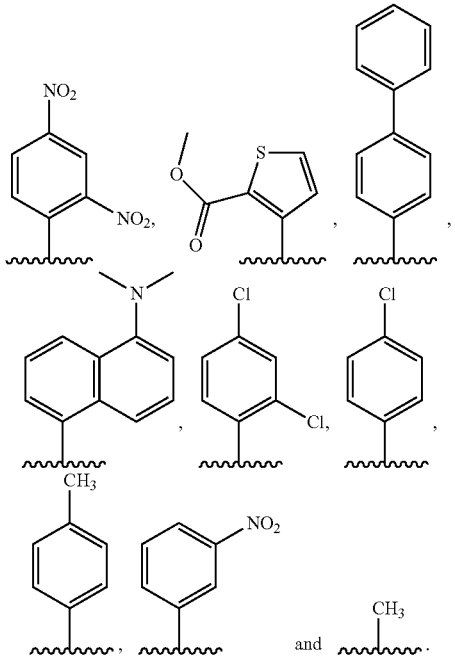

In another embodiment, R$^1$ is:

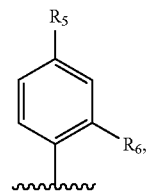

wherein

R$^5$ and R$^6$ are each independently selected from H, halo, hydroxy, nitro, C$_{1-6}$alkyl, C$_{2-6}$alkenyl, C$_{2-6}$alkynyl, C$_{1-6}$haloalkyl, C$_{1-6}$alkoxy, —C(O)O—C$_{1-6}$alkyl, —C(O)O—C$_{6-14}$aryl, C$_{6-14}$aryl, optionally substituted with halo or C$_{1-6}$alkyl, heteroaryl and —NR$^8$R$^9$, wherein R$^8$ and R$^9$ are each individually selected from H and C$_{1-6}$alkyl.

In an embodiment, R$^5$ and R$^6$ are each independently selected from H, halo, nitro, C$_{1-4}$alkyl and C$_{6-10}$aryl. In another embodiment, R$^5$ and R$^6$ are each independently selected from H, chloro, nitro, methyl and phenyl. In an embodiment, R$^5$ is halo, nitro, C$_{1-4}$alkyl or C$_{6-10}$aryl. In another embodiment, R$^5$ is chloro, nitro, methyl or phenyl. In an embodiment, R$^6$ is H, halo, nitro or C$_{1-4}$alkyl. In another embodiment, R$^6$ is H, chloro or nitro.

In an embodiment, R$^5$ and R$^6$ are both nitro.

In an embodiment, R$^8$ and R$^9$ are each individually selected from H and C$_{1-4}$alkyl. In another embodiment, R$^8$ and R$^9$ are each individually selected from C$_{1-4}$alkyl. In another embodiment, R$^8$ and R$^9$ are both —CH$_3$.

Non-limiting examples of compounds of Formula (I) are shown in Table I. Table II shows the structures of compounds provisioned out of the compounds of Formula (I).

Accordingly, it is another embodiment of the present disclosure that the compound of Formula (I) is selected from:
7-Chloro-4-(4-(2,4-dinitrophenylsulfonyl)piperazin-1-yl)quinoline,
Methyl 3-(4-(7-chloroquinolin-4-yl)piperazin-1-ylsulfonyl)thiophene-2-carboxylate,
7-Chloro-4-(4-(biphenylsulfonyl)piperazin-1-yl)quinoline,
5-(4-(7-Chloroquinolin-4-yl)piperazin-1-ylsulfonyl)-N,N-dimethylnaphthalen-1-amine,
7-Chloro-4-(4-(2,4-dichlorophenylsulfonyl)piperazin-1-yl)quinoline,
4-[4-(3-Nitro-benzenesulfonyl)-piperazin-1-yl]-7-trifluoromethyl-quinoline,
4-[4-(4-Chloro-benzenesulfonyl)-piperazin-1-yl]-7-trifluoromethyl-quinoline,
4-[4-(Toluene-4-sulfonyl)-piperazin-1-yl]-7-trifluoromethyl-quinoline,
4-[4-(Biphenyl-4-sulfonyl)-piperazin-1-yl]-7-trifluoromethyl-quinoline,
4-[4-(2,4-Dichloro-benzenesulfonyl)-piperazin-1-yl]-7-trifluoromethyl-quinoline,
4-(4-Methanesulfonyl-piperazin-1-yl)-7-trifluoromethyl-quinoline,
4-[4-(2,4-Dinitro-benzenesulfonyl)-piperazin-1-yl]-7-trifluoromethyl-quinoline,
Dimethyl-{5-[4-(7-trifluoromethyl-quinolin-4-yl)-piperazine-1-sulfonyl]-naphthalen-1-yl}-amine,
3-[4-(7-Trifluoromethyl-quinolin-4-yl)-piperazine-1-sulfonyl]-thiophene-2-carboxylic acid methyl ester,
N-[3-(7-Chloro-quinolin-4-ylamino)-propyl]-methanesulfonamide,
N-[3-(7-Chloro-quinolin-4-ylamino)-propyl]-4-methyl-benzenesulfonamide,
N-[3-(7-Chloro-quinolin-4-ylamino)-propyl]-2,4-dinitro-benzenesulfonamide,
N-(3-(7-Chloroquinolin-4-ylamino)propyl)-3-nitrobenzenesulfonamide,
4-Chloro-N-(3-(7-chloroquinolin-4-ylamino)propyl)benzenesulfonamide,
Biphenyl-4-sulfonic acid [3-(7-chloro-quinolin-4-ylamino)-propyl]-amide,
2,4-Dichloro-N-[3-(7-chloro-quinolin-4-ylamino)-propyl]-benzenesulfonamide,
N-(3-(7-Chloroquinolin-4-ylamino)propyl)thiophene-3-sulfonamide-2-carbomethoxy ester,
N-[3-(7-Trifluoromethyl-quinolin-4-ylamino)-propyl]-methanesulfonamide,
4-Methyl-N-[3-(7-trifluoromethyl-quinolin-4-ylamino)-propyl]-benzenesulfonamide,
2,4-Dinitro-N-[3-(7-trifluoromethyl-quinolin-4-ylamino)-propyl]-benzenesulfonamide,
3-Nitro-N-[3-(7-trifluoromethyl-quinolin-4-ylamino)-propyl]-benzenesulfonamide,
4-Chloro-N-[3-(7-trifluoromethyl-quinolin-4-ylamino)-propyl]-benzenesulfonamide,
5-Dimethylamino-naphthalene-1-sulfonic acid [3-(7-trifluoromethyl-quinolin-4-ylamino)-propyl]-amide,
Biphenyl-4-sulfonic acid [3-(7-trifluoromethyl-quinolin-4-ylamino)-propyl]-amide,
2,4-Dichloro-N-[3-(7-trifluoromethyl-quinolin-4-ylamino)-propyl]-benzenesulfonamide, and
N-(3-(7-Trifluoromethyl-quinolin-4-ylamino)propyl)thiophene-3-sulfonamide-2-carbomethoxy ester,
or a pharmaceutically acceptable salt, solvate or prodrug thereof.

It is an embodiment that the compound of Formula (I) is the compound 7-chloro-4-(4-(2,4-dinitrophenylsulfonyl)piperazin-1yl)quinoline, or a pharmaceutically acceptable salt, solvate or prodrug thereof.

In some embodiments, a compound of Formula (I) is present in the form of a pharmaceutically acceptable salt. It will be apparent to a skilled person that a compound of Formula (I), for example, the exemplary compounds disclosed in Table I may, but need not, be formulated as a solvate, for example a hydrate or a non-covalent complex. Crystal forms and polymorphs of the compounds of Formula (I) are also within the scope of the present disclosure.

In another embodiment of the present disclosure, the compound of Formula (I) or pharmaceutically acceptable salt or solvate thereof is present in the form of a prodrug.

Pharmaceutical Compositions

The compounds of the present disclosure are suitably formulated into pharmaceutical compositions for administration to subjects, for example, in a biologically compatible form suitable for administration in vivo.

Accordingly, in another aspect, the present disclosure relates to a composition comprising one or more compounds of the present disclosure and a carrier. In another embodiment, the composition is a pharmaceutical composition comprising one or more compounds of the present disclosure and a pharmaceutically acceptable carrier. In various embodiments, the pharmaceutical composition comprises one or more compounds of the present disclosure and one or more nontoxic, pharmaceutically acceptable carriers and/or diluents and/or adjuvants and/or excipients, and optionally a therapeutic agent.

The compounds of the present disclosure may be administered to a subject in a variety of forms depending on the selected route of administration, as will be understood by those skilled in the art. A compound of the present disclosure may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

A compound of the present disclosure may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. In an embodiment, coatings that inhibit degradation of the compounds of the present disclosure by esterases, for example plasma esterases, are used in the oral administration forms. Timed-release compositions can be formulated, e.g. liposomes or those wherein the active compound is protected with differentially degradable coatings, such as by microencapsulation, multiple coatings, etc. Liposome delivery systems, include, for example, small unilamellar vesicles, large unilamellar vesicles and multilamellar vesicles. Liposomes can be formed from a variety of phospholipids, such as cholesterol, stearylamine or phosphatidylcholines. It is also possible to freeze-dry the compounds of the present disclosure and use the lyophilizates obtained, for example, for the preparation of products for injection.

A compound of the present disclosure may also be administered parenterally. Solutions of a compound of the present disclosure can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compounds of the present disclosure may also be delivered by the use of monoclonal antibodies as individual carriers to which the compound molecules are coupled. Compounds of the present disclosure may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxidepolylysine substituted with palmitoyl residues. Furthermore, compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In various embodiments, compounds of the disclosure may be prepared as a nanoparticle formulation. For example, one or more compounds of the disclosure may be conjugated to, linked to, adsorbed onto, coated or encapsulated by a nanoscale particle. In this regard, exemplary nanoscale particles that may be useful include without limitation, biological substances such as albumin, gelatine and phospholipids for liposomes, and substances of a chemical nature such as polymers or metal- or silica-containing nanoparticles (e.g. $Fe_3O_4$, gold, and quantum dots). In one embodiment, one or more compounds of the disclosure may be conjugated to, linked to, adsorbed onto, coated or encapsulated by particles that are functionalized, e.g. by conjugation with one or more biorecognition ligands, imaging molecules or other molecules with particular properties, e.g. therapeutic features. For example, a nanoparticle comprising one or more compounds of the disclosure may be coated with poly ethylene glycol (PEG) to provide protection e.g. from cells (e.g. uptake by monocytes) and thus increase the half-life of the one or more compounds. In another example, a nanoparticle comprising one or more compounds of the disclosure may feature a ligand to target the nanoparticle to a cellular receptor, e.g. a cancer cell specific receptor. In a further example, one or more compounds of the disclosure may be conjugated to a quantum dot, providing both carrier and imaging functionalities. A skilled person would know how to design, select and manufacture nanoparticles depending on application (e.g. to improve bio-availability, increase circulation times, control drug release, or to target specific molecules (e.g. proteins), cells or tissues).

In an embodiment, a composition of the present disclosure comprises pharmaceutically acceptable concentrations of one or more of salt, buffering agents, preservatives, solubilizers, stabilizers, wetting agents, emulsifiers, sweeteners, colorants, flavorants, and various compatible carriers. Pharmaceutically acceptable carriers, diluents and excipients are known in the art and are described, for example, in Remington's Pharmaceutical Sciences 16th edition, Osol, A. Ed. (1980) Mack Printing Company, Easton, Pa.

Also within the scope of the present disclosure is a composition comprising a compound of the present disclosure, formulated for use in a medical device, e.g. an implantable or transdermal device for the delivery of a sustained dose of the composition to a subject in need thereof.

In one embodiment, a compound of the present disclosure is formulated for use in or as a composition for treating a subject with cancer or for treating neoplastic cells.

Compounds of the present disclosure may be used alone or in combination with other known agents useful for treating a disease, a disorder or a condition to which the compound of the present disclosure is directed. When used in combination with other such agents, it is an embodiment that the compounds of the present disclosure are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the disclosure that a combination of agents is administered to a subject in a non-contemporaneous fashion.

In another embodiment, a composition of the disclosure comprises a compound of the present disclosure, and a therapeutic agent.

In other embodiments, one or more compounds of the present disclosure is for use in combination with an anti-cancer agent and/or a carcinostatic agent. For example, in one embodiment, one or more compounds of the present disclosure and the anti-cancer agent (and/or carcinostatic agent) may be used at a ratio that a skilled person may readily determine using conventional methods. Exemplary ratios of one or more compounds of the present disclosure to an anti-cancer agent (and/or a carcinostatic agent) that may be useful in the methods and uses described herein include: 1:0.001, 1:0.002, 1:0.003, 1:0.004, 1:0.005, 1:0.006, 1:0.007, 1:0.008, 1:0.009, 1:0.01, 1:0.02, 1:0.03, 1:0.04, 1:0.05, 1:0.06, 1:0.07, 1:0.08, 1:0.09, 1:0.1, 1:0.2, 1:0.3, 1:0.4, 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.25, 1:2.5, 1:2.75, 1:3, 1:3.25, 1:3.5, 1:3.75, 1:4, 1:4.25, 1:4.5, 1:4.75, 1:5, 1:5.25, 1:5.5, 1:5.75, 1:6, 1:6.25, 1:6.5, 1:6.75, 1:7, 1:7.25, 1:7.5, 1:7.75, 1:8, 1:8.25, 1:8.5, 1:8.75, 1:9, 1:9.25, 1:9.5, 1:9.75, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:55, 1:60, 1:65, 1:70, 1:75, 1:80, 1:85, 1:90, 1:95, 1:100, 1:110, 1:120, 1:130, 1:140, 1:150, 1:160, 1:170, 1:180, 1:190, 1:200, 1:250, 1:300, 1:350, 1:400, 1:450, or 1:500.

In various embodiments, the content of one or more compounds of the disclosure in a composition may vary depending on a number of factors, including without limitation, the dosage form. For example, in various embodiments, the composition comprises at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 13%, at least 15%, at least 17%, at least 19%, at least 21%, at least 23%, at least 25%, at least 27%, at least 29%, at least 31%, at least 33%, at least 35%, at least 37%, at least 39%, at least 41%, at least 43%, at least 45%, at least 47%, at least 49%, at least 51%, at least 53%, at least 55%, at least 57%, at least 59%, at least 61%, at least 63%, at least 65%, at least 67%, at least 69%, at least 71%, at least 73%, at least 75%, at least 77%, at least 79%, or more by weight of one or more compounds of the present disclosure, based on the whole composition.

The dosage of compounds of the present disclosure can vary depending on a number of factors, including without limitation the pharmacodynamic properties of the compound, the mode of administration, the age, health and weight of the recipient, the nature and extent of the symptoms, the frequency of the treatment and the type of concurrent treatment, if any, the clearance rate of the compound in the subject to be treated and the dosage form. One of skill in the art can determine the appropriate dosage based on the above factors. For example, compounds of the disclosure may be administered initially in a suitable dosage that may be adjusted as required, depending on the clinical response. For example, dosages of one or more compounds of the disclosure will range from about 1 mg per day to about 2000 mg per day, suitably about 1 mg per day to about 1000 mg per day, more suitably about 1 mg per day to about 500 mg per day. It is an embodiment that a composition of the disclosure comprises about 0.25, about 0.5, about 0.75, about 1.0, about 5.0, about 10.0, about 20.0, about 25.0, about 30.0, about 40.0, about 50.0, about 60.0, about 70.0, about 75.0, about 80.0, about 90.0, about 100.0, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1550, about 1600, about 1650, about 1700, about 1750, about 1800, about 1850, about 1900, about 1950 or about 2000 mg of one or more compounds of the disclosure. In other embodiments, dosages of one or more compounds of the disclosure will range from about 0.01 mg per kg body weight per day to about 30 mg per kg body weight per day, suitably between 0.01 mg per kg body weight per day to about 20 mg per kg body weight per day, more suitably between about 0.01 mg per kg body weight per day to about 10 mg per kg body weight per day. It is an embodiment that a dose of a composition of the disclosure comprises about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1, about 1.5, about 2, abut 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, about 25, about 25.5, about 26, about 26.5, about 27, about 27.5, about 28, about 28.5, about 29, about 29.5, or about 30 mg per kg body weight per day of one or more compounds of the disclosure. As an example, oral dosages of one or more compounds of the present disclosure will range between about 1 mg per day to about 2000 mg per day for an adult, suitably about 1 mg per day to about 500 mg per day, more suitably about 1 mg per day to about 200 mg per day. In an embodiment of the present disclosure, compositions are formulated for oral administration and the compounds are suitably in the form of tablets containing about 0.25, about 0.5, about 0.75, about 1.0, about 5.0, about 10.0, about 20.0, about 25.0, about 30.0, about 40.0, about 50.0, about 60.0, about 70.0, about 75.0, about 80.0, about 90.0, about 100.0, about 150, about 200, about 250, about 300, about 350, about 400, about 450, about 500, about 550, about 600, about 650, about 700, about 750, about 800, about 850, about 900, about 950 or about 1000 mg of active ingredient per tablet. Compounds of the present disclosure may be administered in a single daily dose or the total daily dose may be divided into multiple daily doses, e.g. two, three, four or more daily doses.

III. Methods and Uses of the Disclosure

It is an aspect of the disclosure that compounds of the present disclosure are useful as medicaments. Accordingly, in various embodiments, the disclosure relates to a use of a compound of the present disclosure, or a composition comprising a compound of the present disclosure as a medicament.

In various aspects, the disclosure relates to methods and uses of a compound of the present disclosure for the treatment of cancer in a subject. Accordingly, in one embodiment, the present disclosure relates to a method of inhibiting the proliferation of a cancer cell or for treating a subject with cancer, comprising administering a compound or a composition of the disclosure to a cell or subject in need thereof. In another embodiment, the present disclosure relates to a method of inhibiting the proliferation of a cancer cell comprising administering a therapeutically effective amount of one or more compounds of the present disclosure to a cell or subject in need thereof. In another embodiment, the present disclosure relates to a method of treating cancer comprising administering a therapeutically effective amount of one or more compounds of the present disclosure to a subject in need thereof.

The present disclosure also relates to, in various embodiments, a use of one or more compounds of the disclosure for killing or inhibiting the growth and/or proliferation of a cancer cell, a use of one or more compounds of the disclosure for the preparation of a medicament for killing or inhibiting the growth and/or proliferation of a cancer cell, and one or more compounds of the disclosure for use in killing or inhibiting the growth and/or proliferation of a cancer cell.

In one embodiment, a compound of the present disclosure or a composition comprising a compound of the present disclosure is useful in treating cancer. Accordingly, in various embodiments, the present disclosure further relates to a use of one or more compounds of the disclosure for treating cancer, a use of one or more compounds of the disclosure for preparing a medicament for treating cancer, and one or more compounds of the disclosure for use in treating cancer.

In another embodiment, the present disclosure relates to a method of treating cancer comprising administering a therapeutically effective amount of 7-chloro-4-(4-(2,4-dinitrophenylsulfonyl)piperazin-1yl) quinoline, or a pharmaceutically acceptable salt, solvate or prodrug thereof to a subject in need thereof. In a further embodiment, the present disclosure relates to a use of 7-chloro-4-(4-(2,4-dinitrophenylsulfonyl)piperazin-1yl) quinoline, or a pharmaceutically acceptable salt, solvate or prodrug thereof for treatment of cancer, a use of 7-chloro-4-(4-(2,4-dinitrophenylsulfonyl)piperazin-1yl) quinoline, or a pharmaceutically acceptable salt, solvate or prodrug thereof for use in the manufacture of a medicament for treatment of cancer, and 7-chloro-4-(4-(2,4-dinitrophenylsulfonyl)piperazin-1 yl) quinoline, or a pharmaceutically acceptable salt, solvate or prodrug thereof for use in treatment of cancer.

In various embodiments, the cancer is a hematopoietic malignancy, such as leukemia, lymphoma, and myeloma; sarcoma; carcinoma; melanoma; adenoma; a cancer of cells of the nervous system (such as glioma cells (both repair competent and defective glioblastoma cells)); a cancer of cells of the gastrointestinal system, a cancer of cells of the urogenital system, or a cancer of cells of the respiratory system. Non-limiting examples of leukemia include: acute lymphoblastic leukemia (ALL), acute myelocytic leukemia (AML), chronic myeloid leukemia (CML), chronic lymphocytic leukemia (CLL) and juvenile myelo-monocytic leukemia (JMML). Non-limiting examples of lymphoma include: B-cell Burkitt's lymphoma, Hodgkin's lymphoma, non-Hodgkin's lymphoma, T cell lymphoma and histiocytic lymphoma. In various embodiments, the cancer is breast cancer, cervical cancer, lymphoma, or multiple myeloma.

For example, in one embodiment, a subject with cancer treated with a compound of the present disclosure, or a composition comprising a compound of the present disclosure, demonstrates an at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% reduction in tumor volume or size in the subject, relative to the subject prior to treatment. For example, in another embodiment, a subject with cancer treated with a compound of the present disclosure, or a composition comprising a compound of the present disclosure, demonstrates an at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 fold reduction in tumor volume or size in the subject, relative to the subject prior to treatment.

In another embodiment, a subject with cancer treated with a compound of the present disclosure, or a composition comprising a compound of the present disclosure, demonstrates an at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% reduction in the number and/or concentration of tumor cells in the subject, relative to the subject prior to treatment.

In another embodiment, a subject with cancer treated with a compound of the present disclosure or a composition comprising a compound of the present disclosure demonstrates an at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% increase in duration of survival of the subject, compared to an untreated control subject with the same or similar type of cancer as the treated subject.

It is an embodiment of the disclosure that some compounds of the disclosure are useful in selectively killing or inhibiting growth and/or proliferation of cancer cells but not cells that are not cancerous. For example, in various embodiments, the compound of the disclosure useful in selectively killing or inhibiting growth and/or proliferation of cancer cells, but not cells that are not cancerous, is 7-chloro-4-(4-(2,4-dinitrophenylsulfonyl)piperazin-1yl) quinoline, 4-(4-Methanesulfonyl-piperazin-1-yl)-7-trifluoromethyl-quinoline, or N-(3-(7-Chloroquinolin-4-ylamino)propyl) thiophene-3-sulfonamide-2-carbomethoxy ester.

In various embodiments, a compound of the disclosure that selectively kills cancer cells, kills cancer cells at a rate or at a frequency that is at least 2.5×, at least 3×, at least 3.5×, at least 4×, at least 4.5×, at least 5×, at least 5.5×, at least 6×, at least 6.5×, at least 7×, at least 7.5×, at least 8×, at least 8.5×, at least 9×, at least 9.5×, at least 10×, at least 10.5×, at least 11×, at least 11.5×, at least 12×, at least 12.5×, at least 13×, at least 13.5×, at least 14×, at least 14.5×, at least 15×, at least 15.5×, at least 16×, at least 16.5×, at least 17×, at least 17.5×, at least 18×, at least 18.5×, at least 19×, at least 19.5×, or at least 20× greater than a corresponding cell that is not cancerous.

In other embodiments, a compound of the disclosure that selectively kills cancer cells or inhibits cancer cell growth and/or proliferation does so at a concentration that is at least 2.5×, at least 3×, at least 3.5×, at least 4×, at least 4.5×, at least 5×, at least 5.5×, at least 6×, at least 6.5×, at least 7×, at least 7.5×, at least 8×, at least 8.5×, at least 9×, at least 9.5×, at least 10×, at least 10.5×, at least 11×, at least 11.5×, at least 12×, at least 12.5×, at least 13×, at least 13.5×, at least 14×, at least 14.5×, at least 15×, at least 15.5×, at least 16×, at least 16.5×, at least 17×, at least 17.5×, at least 18×, at least 18.5×, at least 19×, at least 19.5×, or at least 20× lower compared to the concentration required to kill or inhibit the growth and/or proliferation of a corresponding cell that is not cancerous. For example, the concentration of a compound of the disclosure that selectively kills cancer cells compared to non-cancer cells may be assessed by determining $IC_{50}$ values; and the concentration of a compound of the disclosure that selectively inhibits cancer cell growth and/or proliferation compared to non-cancer cells may be assessed by determining $GI_{50}$ values.

In one embodiment, a pharmaceutical composition comprising a compound of the present disclosure is administered to, or used in, a subject in a variety of forms depending on the selected route of administration, as will be understood by those skilled in the art. In various embodiments, a composition or a compound of the disclosure is administered, for example orally (e.g. as a tablet, capsule, solution, emulsion, suspension), by injection (intramuscular, intradermal, subcutaneous, intraperitoneal, systemically), by puncture, transdermally, intramucosally, or intranasally. In another embodiment, a compound of the present disclosure or a composition comprising a compound of the present disclosure is useful in combination with a therapeutic agent. In this regard, in various embodiments, a compound of the disclosure (or a composition comprising a compound of the disclosure), and a therapeutic agent may be used, or administered to a subject, for example, simultaneously or serially. Also within the scope of the disclosure is use of a compound or a composition of the disclosure in adjunctive therapy (for example, ionizing radiation).

In other aspects, the disclosure relates to methods for modulating cell proliferation, for inhibiting or reducing proteasome levels in a cell, or for inducing apoptosis in a cell; the method comprising administering a compound or a composition of the disclosure to a cell or subject in need thereof.

In one embodiment, a compound of the present disclosure or a composition comprising a compound of the present disclosure is useful in methods for modulating cell proliferation. This method comprises contacting the cell with an amount of a compound or a composition of the disclosure effective to delay cell cycle progression of the cell. For example, in one embodiment, a cell administered a compound or a composition of the disclosure demonstrates a delay in cell cycle progression by at least 10%, at least 15%, at least 20%, at least 25%, at least 30%, at least 35%, at least 40%, at least 45%, at least 50%, at least 55%, at least 60%, at least 65%, or at least 70% compared to an untreated cell. In one embodiment, a compound or a composition of the disclosure, is useful in modulating cell proliferation of a cancer cell, or a cell derived from a tumor. The present disclosure further relates to a use of one or more compounds of the present disclosure for modulating cell proliferation, a use of one or more compounds of the present disclosure for preparing a medicament for modulating cell proliferation and one or more compounds of the present disclosure for use in modulating cell proliferation. It is an embodiment that the cell is a cancer cell or a cell derived from a tumor.

In one embodiment, a compound of the present disclosure or a composition comprising a compound of the present disclosure is useful in methods for inhibiting or reducing a level of a proteasome in a cell. As used herein, inhibiting or reducing a level of a proteasome refers a reduction of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or 100% of the level of a proteasome in a cell treated with a compound or a composition of the disclosure, compared to an untreated cell. As used herein, a level of proteasome or a proteasome level refers to the absolute amount, concentration, or level of the biological activity of the proteasome. In one embodiment, a compound or a composition of the disclosure is useful in inhibiting or reducing proteasome levels in a cancer cell, or a cell derived from a tumor. In an embodiment, the present disclosure relates to a method for inhibiting or reducing a level of a proteasome in a cell comprising administering a therapeutically effective amount of one or more compounds of the present disclosure to a cell. The present disclosure also relates to a use of one or more compounds of the present disclosure for inhibiting or reducing a level of a proteasome in a cell, a use of one or more compounds of the present disclosure for the preparation of a medicament for inhibiting or reducing a level of a proteasome in a cell, and one or more compounds of the present disclosure for use in inhibiting or reducing a level of a proteasome in a cell. It is an embodiment that the cell is a cancer cell or a cell derived from a tumor.

In one embodiment, a compound of the present disclosure or a composition comprising a compound of the present disclosure is useful in methods for inducing apoptosis in a cell. This method comprises contacting the cell with an amount of a compound or a composition of the disclosure effective to cause the cell to enter programmed cell death. In one embodiment, a compound or a composition of the disclosure, is useful in inducing apoptosis in a cancer cell, or a cell derived from a tumor. In an embodiment, the present disclosure relates to a method for inducing apoptosis in a cell comprising administering a therapeutically effective amount of one or more compounds of the present disclosure to a cell. The present disclosure also relates to a use of one or more compounds of the present disclosure for inducing apoptosis in a cell, a use of one or more compounds of the present disclosure for the preparation of a medicament for inducing apoptosis in a cell, and one or more compounds of the present disclosure for use in inducing apoptosis in a cell. It is an embodiment that the cell is a cancer cell or a cell derived from a tumor.

Cyclins are a family of proteins that control the progression of cells through the cell cycle by activating cyclin-dependent kinase (Cdk) enzymes. In one embodiment, a compound of the disclosure is useful in modulating the levels of cyclins A, B and E, and thus modulate the progression of a cell through the cell cycle, and/or result in apoptosis of the cell.

Proteasomes are protein complexes that function in normal protein turnover and in the degradation of unneeded or damaged proteins; and thus are essential to cellular homeostasis. However, cells that have a high need for proteasomal regulatory activity, e.g. in rapidly proliferating cells, are susceptible to the toxic consequences of inhibiting the normal degradative mechanism. As most cancer cells contain a high number of chromosomes and, thus, often produce unusually high levels of (often misfolded) proteins, optimal proteasome activity is especially critical for the survival of tumor cells. Indeed, it was found that proteasome inhibitors induced programmed cell death preferentially in transformed cells. Accordingly, a compound of the disclosure may be useful in inhibiting proliferation of cells that have a high need for proteasomal activity, e.g. in cancer, but not normal cells; i.e. cells that are not cancerous.

Methods, approaches and techniques to detect, quantify and/or evaluate the effectiveness of a compound of the disclosure in treating a disease, disorder or condition are known in the art, and may, for example depend on the disease, disorder or condition being treated. Similarly, methods, approaches and techniques to detect, quantify and/or evaluate changes in cell proliferation, proteasome activity, and induction of apoptosis are known to those of skill in the art. Accordingly, a skilled person could readily use such approaches to follow the progression of a subject, or of a cell, treated according to methods of the disclosure as described herein. For example, with respect to cancer, a skilled person would understand that a reduction in tumor burden may be evaluated by known methods, e.g. by observed or detected changes in tumor size or volume, analyzing a tissue specimen for the presence of one or more biomarkers (e.g. a tumor-specific antigen), etc. Further, effects of using a compound of the disclosure may be followed in a subject by monitoring conventional parameters, and may include without limitation, body weight, alanine transaminase levels, levels of cyclins or other cell cycle related or associated proteins, and cellular morphology.

A compound of the present disclosure may have additional medical and/or research applications. For example, compounds of the disclosure may be useful as tools in many aspects of cell biology research and diagnostics, for example, for cell cycle regulation-related studies.

In one aspect, the disclosure relates to the use of a compound of the present disclosure in inducing aneuploidy in a cell. This method comprises contacting the cell with an amount of a compound of the disclosure effective to cause chromosome amplification in the cell. In one embodiment, a compound of the present disclosure is useful in inducing aneuploidy in a cancer cell, or a cell derived from a tumor. In an embodiment, the present disclosure relates to a method for inducing aneuploidy in a cell comprising administering a therapeutically effective amount of one or more compounds of the present disclosure to a cell. The present disclosure also relates to, in various embodiments, a use of one or more compounds of the present disclosure for inducing aneuploidy in a cell, a use of one or more compounds of the present disclosure for the preparation of a medicament for inducing aneuploidy in a cell, and one or more compounds of the present disclosure for use in inducing aneuploidy in a cell. It is an embodiment that the cell is a cancer cell or a cell derived from a tumor.

In other aspects, the disclosure relates to the use of a compound of the present disclosure in inactivating Cdk1 and/or in increasing a level of cyclin B and/or cyclin E in a cell. This method comprises contacting the cell with an amount of a compound of the disclosure effective to cause Cdk1 inactivation, and/or to increase the level of cyclin B and/or cyclin E. In one embodiment, a compound of the present disclosure is useful in inactivating Cdk1 and/or in increasing cyclin B and/or cyclin E levels in a cancer cell, or a cell derived from a tumor. As used herein, a level of cyclin B or cyclin E refers to the absolute amount, concentration, or level of the biological activity of cyclin B or cyclin E. In an embodiment, the present disclosure relates to a method for inactivating Cdk1 and/or increasing a level of cyclin B and/or cyclin E in a cell comprising administering a therapeutically effective amount of one or more compounds of the present disclosure to a cell. The present disclosure also relates to a use of one or more compounds of the present disclosure for inactivating Cdk1 and/or increasing a level of cyclin B and/or cyclin E in a cell, a use of one or more compounds of the present disclosure for the preparation of a medicament for inactivating Cdk1 and/or increasing a level of cyclin B and/or cyclin E in a cell, and one or more compounds of the present disclosure for use in inactivating Cdk1 and/or increasing a level of cyclin B and/or cyclin E in a cell. It is an embodiment that the cell is a cancer cell or a cell derived from a tumor.

In one embodiment, a compound of the disclosure, such as VR-23, is useful in studying the role of proteasome and the substrate specificity of proteasome in the regulation of cell cycle progression at different cell cycle positions. For example, in various embodiments, since a compound of the disclosure, such as VR-23, deregulates the timely degradation of cyclin E, leading to supranumerary (i.e., multiple centrosomes), a compound of the disclosure, such as VR-23, is useful to study the mechanism of centrosome duplication and maturation in the context of DNA replication and cell cycle progression. In other embodiments, a compound of the disclosure, such as VR-23, inactivates Cdk1 and prevents cyclin B degradation and thus is a useful tool in studying the regulation of mitosis and cell cytokinesis mechanism. In further embodiments, since multiple centrosomes in a single cell can lead to aneuploidy, a hallmark of genetic instability, a compound of the disclosure, such as VR-23, is a useful tool for the study of genetic (in)stability and tumorigenesis.

For the following methods and uses: treating a subject with cancer, inducing aneuploidy in a cell, increasing a level of cyclin B and/or cyclin E in a cell, inactivating Cdk1, inhibiting a level of proteasome in a cell, modulating proliferation of a cell, delaying cell cycle progression in a cell, and/or inducing apoptosis in a cell; a compound of the disclosure or a compound of the present disclosure also includes 7-Chloro-4-(4-tosylpiperazin-1-yl)quinoline, 7-Chloro-4-(4-(4-chlorophenylsulfonyl)piperazin-1-yl)quinoline, 7-Chloro-4-(4-(3-nitrophenylsulfonyl)piperazin-1-yl)quinoline, and 5-Dimethylamino-naphthalene-1-sulfonic acid [3-(7-chloro-quinolin-4-ylamino)-propyl]-amide, or a pharmaceutically acceptable salt, solvate or prodrug thereof.

IV. Kits and Commercial Packages

Kits and commercial packages for use in the therapeutic, diagnostic and research applications described herein are also within the scope of the present disclosure. In one embodiment, a kit or commercial package may comprise a compound of the present disclosure or a composition comprising a compound of the present disclosure together with instructions for using the kit. Further, the kit may comprise one or more reagents, buffers, packaging materials, and containers for holding the components of the kit.

Embodiments of the present disclosure will be described with reference to the following Examples that are provided for illustrative purposes only and should not be used to construe or limit the scope of the disclosure.

EXAMPLES

Rationale of Design

It was demonstrated previously that 10 μM chloroquine (CQ) increased cancer cell killing when used in combination with other cancer therapeutic agents[1-5], and the CQ-mediated enhancement of cell killing was cancer-specific[1]. In the study, certain CQ derivatives containing linear alkyl side chain, dialkyl substitutions and heterocyclic ring substitutions showed higher activity than CQ in killing MDA-MB468 and MCF7 breast cancer cells[3,5].

In a further study, hybrid compounds of 4-piperazinylquinoline-isatin were synthesized by a Mannich base reaction, and their activities on two human breast tumor and two matching non-cancer breast cell lines were examined[6,7]. It was found that the antiproliferative effect of 4-piperazinylquinoline-isatin hybrid compounds were more active on cancer than non-cancer cells.

Compounds containing a sulfonyl pharmacophore have been shown to possess many different types of biological activities and are used as antibacterial, anticarbonic anhydrase, antiviral, and hypoglycemic agents. The sulfonyl group is known as synthon in the preparation of various medicinally active chemical compounds. In vitro and in vivo studies showed that certain sulfonyl derivatives possess substantial antitumor activity[8-10].

Toward developing anticancer agents, thirty-five 4-piperazinyl/amino quinoline derived sulfonyl compounds (Tables I and II) were designed and synthesized by a hybrid pharmacophore approach.

Materials and Methods

For example, compounds of the disclosure may be prepared by the methods shown in Scheme 1.

Scheme 1

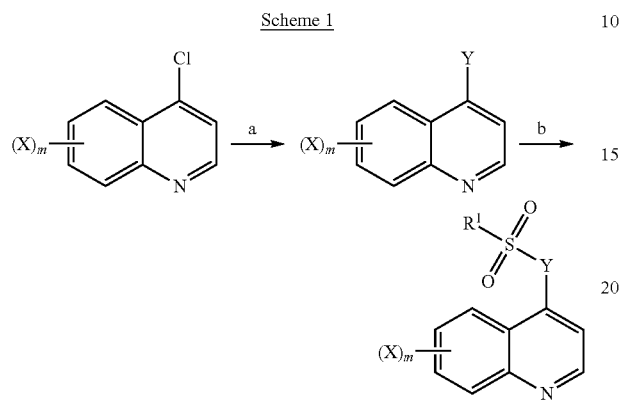

Reagents and Conditions: (a) Y, Triethylamine, 120-130° C. for 6 hours; (b) $R^1$-sulfonyl chloride, Triethylamine, THF, RT, 4 hours.

In various embodiments, compounds of Formula (I) where Y is piperazine or 1,3 diaminopropane, and X is Cl or $CF_3$ may be prepared according to Scheme 2:

performed on a Perkin-Elmer 2400 C, H, N analyzer and values were within the acceptable limits of the calculated values. The $^1H$ spectra were recorded on a DPX-500 MHz Bruker FT-NMR spectrometer using $CDCl_3$ and DMSO-$d_6$ as solvent. The chemical shifts were reported as parts per million (δ ppm) tetramethylsilane (TMS) as an internal standard. Mass spectra were obtained on a JEOL-SX-102 instrument using electron spray mass spectroscopy (ES-MS). The progress of the reaction was monitored on ready-made silica-gel plates (Merck) using chloroform-methanol (9:1) as solvent. Iodine was used as a developing agent or by spraying with the Dragendorff's reagent. Chromatographic purification was performed over a silica gel (100-200 mesh). All chemicals and reagents obtained from Aldrich (USA) were used without further purification.

General Synthesis of
7-substituted-4-piperazin-1-yl-quinoline (34, 35)

A mixture of 7-substituted-4-chloro-quinoline (32 or 33) (10.10 mmol), piperazine (2.61 g, 30.30 mmol) and triethylamine (1.4 mL, 10.10 mmol) were heated slowly to 80° C. over 1 hour while stirring. The temperature was then increased to 130-140° C. for 6 hours where it was kept for while stirring continuously. The reaction mixture was cooled to room temperature and taken up in dichloromethane. The Scheme 2

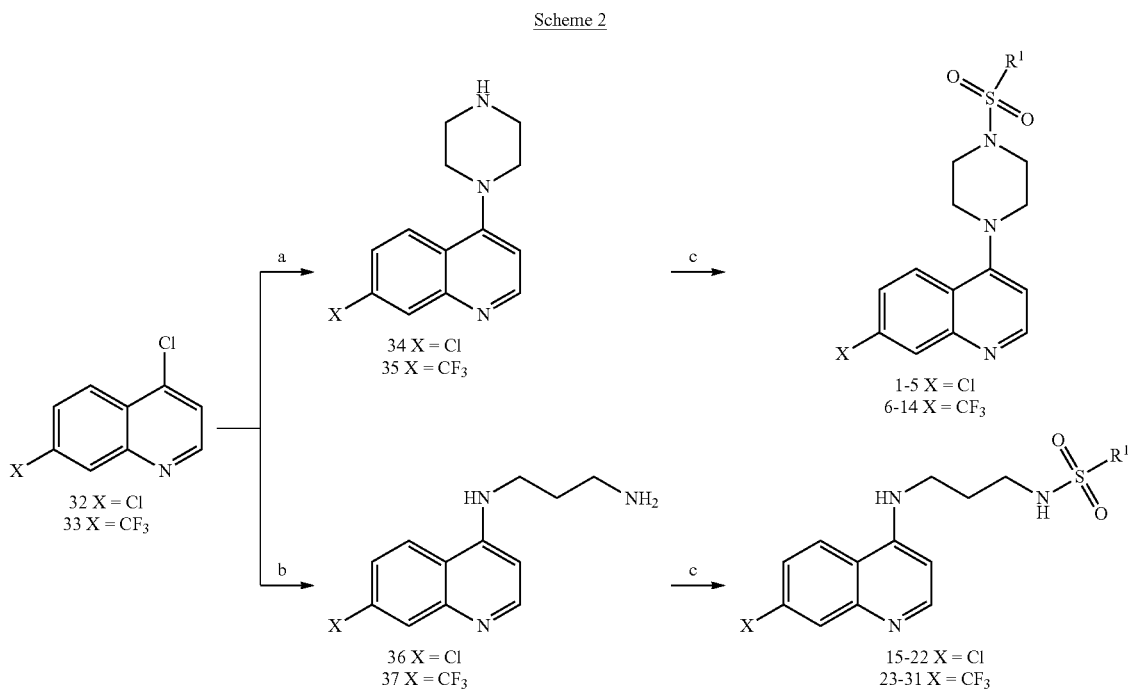

Reagents and Conditions: (a) Piperazine, Triethylamine, 120-130° C. for 6 h; (b) 1,3-Diaminopropane, Triethylamine, 120-130° C. for 6 h; (c) $R^1$-sulfonyl chloride, Triethylamine, THF, RT, 4 h.

Melting points (mp) were taken in open capillaries on the Complab melting point apparatus. Elemental analysis was organic layer was washed with 5% aq. $NaHCO_3$, followed by washing with water and then with brine. The organic layer was dried over anhydrous $Na_2SO_4$ and solvent was removed under reduced pressure, and the residue was then precipitated by addition of mixture of solvent hexane:chloroform (8:2).

7-Chloro-4-piperazin-1-yl-quinoline (34)

$^1$H NMR (500 MHz, CDCl$_3$): δ 2.31 (br s, 1H, NH), 3.15 (s, 4H, N(CH$_2$CH$_2$)$_2$NAr), 3.18 (s, 4H, N(CH$_2$CH$_2$)$_2$NAr), 6.80-6.81 (d, J=5.0 Hz, 1H, Ar—H), 7.46-7.47 (d, J=5.0 Hz, 1H, Ar—H), 7.92-7.94 (d, J=10.0 Hz, 1H, Ar—H), 8.01 (s, 1H, Ar—H), 8.68-8.69 (d, J=5.0 Hz, 1H, Ar—H); $^{13}$C NMR (500 MHz, CDCl$_3$): δ 46.10, 53.58, 108.97, 121.97, 125.24, 126.09, 128.91, 134.84, 150.22, 151.99, 157.38; ES-MS m/z 248 [M+H]$^+$; Anal. Calcd for C$_{13}$H$_{14}$ClN$_3$: C, 63.03; H, 5.70; N, 16.96. found: C, 63.01; H, 5.73; N, 16.99.

4-Piperazin-1-yl-7-trifluoromethyl-quinoline (35)

$^1$H NMR (500 MHz, CDCl$_3$): δ 1.78 (br s, 1H, NH), 3.18 (s, 4H, N(CH$_2$CH$_2$)$_2$NAr), 3.24 (s, 4H, N(CH$_2$CH$_2$)$_2$NAr), 7.07-7.08 (d, J=5.0 Hz, 1H, Ar—H), 7.46-7.47 (d, J=5.0 Hz, 1H, Ar—H), 7.63-7.65 (d, J=10.0 Hz, 1H, Ar—H), 8.13-8.14 (d, J=5.0 Hz, 1H, Ar—H), 8.34 (s, 1H, Ar—H), 8.81-8.82 (d, J=5.0 Hz, 1H, Ar—H); $^{13}$C NMR (500 MHz, CDCl$_3$): δ 52.15, 53.48, 110.64, 120.79, 125.14, 125.22, 127.76, 130.70, 130.96, 148.73, 152.20, 157.19; ES-MS m/z 282 [M+H]$^+$; Anal. Calcd for C$_{14}$H$_{14}$F$_3$N$_3$: C, 59.78; H, 5.02; N, 14.94. found: C, 59.75; H, 4.98; N, 14.97.

General Synthesis of 7-substituted-4-(4-(alkyl/aryl/heteroalkylsulfonyl)piperazin-1-yl)quinoline (1-14) (Table I)

To a solution of compound 7-substituted-4-piperazin-1-yl-quinoline (3.20 mmol) in anhydrous THF (25 mL) under a nitrogen atmosphere was added triethylamine (0.44 mL, 3.20 mmol). The mixture was cooled to below 0° C. Alkyl/aryl/heteroalkyl sulfonyl chloride (3.20 mmol) was added slowly, keeping the temperature below 5° C., and the reaction was stirred in an ice bath for 1 h. After dilution with saturated NaHCO$_3$ solution (20 mL), the reaction was extracted with ether (2×). The organic extracts were dried over Na$_2$SO$_4$, filtered and evaporated to leave crude compound. The crude product was purified through chromatography on silica gel, eluting with chloroform-methanol.

7-Chloro-4-(4-(2,4-dinitrophenylsulfonyl)piperazin-1-yl)quinoline (1) VR-23

Yellow solid; 68% yield; mp 238-240° C.; IR (KBr, cm$^{-1}$): 1174.3 (SO$_2$); $^1$H NMR (500 MHz, CDCl$_3$): δ 3.33 (s, 4H, N(CH$_2$CH$_2$)$_2$N—Ar), 3.69 (s, 4H, N(CH$_2$CH$_2$)$_2$N—Ar), 6.89-6.90 (d, J=5.0 Hz, 1H, Ar—H), 7.46-7.48 (d, J=10.0 Hz, 1H, Ar—H), 7.87-7.89 (d, J=10.0 Hz, 1H, Ar—H), 8.09-8.10 (d, J=5.0 Hz, 1H, Ar—H), 8.31-8.33 (d, J=10.0 Hz, 1H, Ar—H), 8.55 (s, 1H, Ar—H), 8.57-8.59 (d, J=5.0 Hz, 1H, Ar—H), 8.78-8.79 (d, J=5.0 Hz, 1H, Ar—H); $^{13}$C NMR (CDCl$_3$): δ 46.19, 51.93, 109.67, 119.91, 121.71, 124.36, 126.20, 126.89, 129.24, 132.78, 135.36, 137.10, 140.51, 150.18, 151.99, 155.85, 159.75; ES-MS m/z 479 [M+H]$^+$; Anal. Calcd for C$_{19}$H$_{16}$ClN$_5$O$_6$S: C, 47.75; H, 3.37; N, 14.66. found: C, 47.77; H, 3.39; N, 14.63.

Methyl 3-(4-(7-chloroquinolin-4-yl)piperazin-1-ylsulfonyl)thiophene-2-carboxylate (2) VR-36

Pale yellowish white solid; 72% yield; mp 117-119° C.; IR (KBr, cm$^{-1}$): 1169.8 (SO$_2$); $^1$H NMR (500 MHz, CDCl$_3$): δ 3.44 (s, 4H, N(CH$_2$CH$_2$)$_2$N—Ar), 3.65 (s, 4H, N(CH$_2$CH$_2$)$_2$N—Ar), 3.91 (s, 3H, COOCH$_3$), 6.85-6.86 (d, J=5.0 Hz, 1H, Ar—H), 7.41-7.42 (d, J=5.0 Hz, 1H, Ar—H), 7.54-7.57 (dd, J$_1$=10.0 Hz, J$_2$=5.0 Hz, 1H, Ar—H), 7.72-7.73 (d, J=5.0 Hz, 1H, Ar—H), 7.86-7.88 (d, J=10.0 Hz, 1H, Ar—H), 8.06 (s, 1H, Ar—H), 8.74-8.75 (d, J=5.0 Hz, 1H, Ar—H); $^{13}$C NMR (CDCl$_3$): δ 46.13, 52.02, 109.48, 121.77, 124.69, 126.59, 128.80, 129.31, 130.89, 132.45, 134.07, 135.14, 140.44, 151.97, 156.27, 159.95, 167.75; ES-MS m/z 453 [M+H]$^+$; Anal. Calcd for C$_{19}$H$_{18}$ClN$_3$O$_4$S$_2$: C, 50.49; H, 4.01; N, 9.30. found: C, 50.51; H, 4.04; N, 9.34.

7-Chloro-4-(4-(biphenylsulfonyl)piperazin-1-yl)quinoline (3) VR-34

Pale yellow solid; 68% yield; mp 238-240° C.; IR (KBr, cm$^{-1}$): 1165.3 (SO$_2$); $^1$H NMR (500 MHz, CDCl$_3$): δ 3.30 (s, 4H, N(CH$_2$CH$_2$)$_2$N—Ar), 3.39 (s, 4H, N(CH$_2$CH$_2$)$_2$N—Ar), 6.95-6.96 (d, J=5.0 Hz, 1H, Ar—H), 7.42-7.44 (d, J=10.0 Hz, 1H, Ar—H), 7.46-7.50 (m, 2H, Ar—H), 7.55-7.57 (d, J=10.0 Hz, 2H, Ar—H), 7.61-7.63 (d, J=10.0 Hz, 2H, Ar—H), 7.68-7.70 (d, J=10.0 Hz, 2H, Ar—H), 7.98-8.00 (d, J=10.0 Hz, 2H, Ar—H), 8.35 (s, 1H, Ar—H), 8.84-8.85 (d, J=5.0 Hz, 1H, Ar—H); $^{13}$C NMR (CDCl$_3$): δ 46.07, 51.57, 109.50, 121.69, 124.64, 126.55, 127.34, 128.37, 128.67, 129.30, 130.89, 132.64, 134.07, 135.09, 139.06, 146.09, 150.09, 151.99, 156.06; ES-MS m/z 465 [M+H]$^+$; Anal. Calcd for C$_{25}$H$_{22}$ClN$_3$O$_2$S: C, 64.72; H, 4.78; N, 9.06. found: C, 64.76; H, 4.80; N, 9.04.

5-(4-(7-Chloroquinolin-4-yl)piperazin-1-ylsulfonyl)-N,N-dimethylnaphthalen-1-amine (4) VR-37

Pale yellowish white solid; 68% yield; mp 145-147° C.; IR (KBr, cm$^{-1}$): 3295.7 (NH); 1192.3 (SO$_2$); $^1$H NMR (500 MHz, CDCl$_3$): δ 2.94 (s, 6H, N(CH$_3$)$_2$), 3.25 (s, 4H, N(CH$_2$CH$_2$)$_2$N—Ar), 3.52 (s, 4H, N(CH$_2$CH$_2$)$_2$N—Ar), 6.80-6.81 (d, J=5.0 Hz, 1H, Ar—H), 7.22-7.23 (d, J=5.0 Hz, 1H, Ar—H), 7.28-7.29 (d, J=5.0 Hz, 1H, Ar—H), 7.58-7.60 (d, J=10.0 Hz, 1H, Ar—H), 7.78-7.79 (d, J=5.0 Hz, 1H, Ar—H), 7.80-7.81 (d, J=5.0 Hz, 1H, Ar—H), 8.29-8.31 (dd, J$_1$=10.0 Hz, J$_2$=5.0 Hz, 1H, Ar—H), 8.46-8.48 (dd, J$_1$=10.0 Hz, J$_2$=5.0 Hz, 1H, Ar—H), 8.63-8.65 (dd, J$_1$=10.0 Hz, J$_2$=5.0 Hz, 1H, Ar—H), 8.71 (s, 1H, Ar—H), 8.72-8.73 (d, J=5.0 Hz, 1H, Ar—H); $^{13}$C NMR (CDCl$_3$): δ 45.45, 45.64, 51.79, 109.44, 115.37, 119.53, 121.72, 123.24, 124.64, 126.58, 128.26, 128.26, 129.05, 130.16, 130.47, 130.88, 131.05, 132.53, 135.14, 150.10, 151.92, 156.19; ES-MS m/z 482 [M+H]$^+$; Anal. Calcd for C$_{25}$H$_{25}$ClN$_4$O$_2$S: C, 62.42; H, 5.24; N, 11.65. found: C, 62.44; H, 5.21; N, 11.61.

7-Chloro-4-(4-(2,4-dichlorophenylsulfonyl)piperazin-1-yl)quinoline (5) VR-35

Pale yellowish white solid; 68% yield; mp 145-147° C.; IR (KBr, cm$^{-1}$): 1172.3 (SO$_2$); $^1$H NMR (500 MHz, CDCl$_3$): δ 3.24 (s, 4H, N(CH$_2$CH$_2$)$_2$N—Ar), 3.63 (s, 4H, N(CH$_2$CH$_2$)$_2$N—Ar), 6.86-6.87 (d, J=5.0 Hz, 1H, Ar—H), 7.43-7.45 (m, 2H, Ar—H), 7.54-7.55 (d, J=5.0 Hz, 1H, Ar—H), 7.61 (s, 1H, Ar—H), 7.87-7.89 (d, J=10.0 Hz, 1H, Ar—H), 8.05 (s, 1H, Ar—H), 8.76-8.77 (d, J=5.0 Hz, 1H, Ar—H); $^{13}$C NMR (CDCl$_3$): δ 41.00, 47.26, 104.81, 117.02, 119.81, 121.96, 122.75, 124.38, 127.38, 128.34, 128.59, 129.86, 130.47, 135.13, 145.40, 147.22, 151.40; ES-MS m/z 458 [M+H]$^+$; Anal. Calcd for C$_{19}$H$_{16}$Cl$_3$N$_3$O$_2$S: C, 49.96; H, 3.53; N, 9.20. found: C, 49.99; H, 3.51; N, 9.18.

4-[4-(3-Nitro-benzenesulfonyl)-piperazin-1-yl]-7-trifluoromethyl-quinoline (6) VR-41

Pale yellowish white solid; 65% yield; mp 199-201° C.; IR (KBr, cm$^{-1}$): 1168.9 (SO$_2$); $^1$H NMR (500 MHz, CDCl$_3$):

δ 3.36 (s, 4H, N(CH$_2$CH$_2$)$_2$N—Ar), 3.54 (s, 4H, N(CH$_2$CH$_2$)$_2$N—Ar), 6.98-6.99 (d, J=5.0 Hz, 1H, Ar—H), 7.62-7.64 (d, J=10.0 Hz, 1H, Ar—H), 7.86-7.88 (d, J=10.0 Hz, 1H, Ar—H), 7.90-7.91 (d, J=5.0 Hz, 1H, Ar—H), 7.96-7.97 (d, J=5.0 Hz, 1H, Ar—H), 8.20-8.21 (d, J=5.0 Hz, 1H, Ar—H), 8.55-8.57 (d, J=10.0 Hz, 1H, Ar—H), 8.71 (s, 1H, Ar—H), 8.85-8.86 (d, J=5.0 Hz, 1H, Ar—H); $^{13}$C NMR (CDCl$_3$): δ 46.05, 51.52, 110.87, 121.40, 122.83, 124.32, 124.89, 127.70, 128.14, 129.15, 130.81, 131.08, 133.19, 138.20, 148.58, 148.78, 152.23, 155.65; ES-MS m/z 467 [M+H]$^+$; Anal. Calcd for C$_{20}$H$_{17}$F$_3$N$_4$O$_4$S: C, 51.50; H, 3.67; N, 12.01. found: C, 51.47; H, 3.70; N, 11.97.

4-[4-(4-Chloro-benzenesulfonyl)-piperazin-1-yl]-7-trifluoromethyl-quinoline (7) VR-40

White solid; 69% yield; mp 144-146° C.; IR (KBr, cm$^{-1}$): 1174.9 (SO$_2$); mp 171-173° C.; $^1$H NMR (500 MHz, CDCl$_3$): δ 3.23 (s, 4H, N(CH$_2$CH$_2$)$_2$N—Ar), 3.57 (s, 4H, N(CH$_2$CH$_2$)$_2$N—Ar), 7.01-7.02 (d, J=5.0 Hz, 1H, Ar—H), 7.64-7.66 (d, J=10.0 Hz, 2H, Ar—H), 7.72-7.73 (d, J=5.0 Hz, 1H, Ar—H), 7.85-7.87 (d, J=10.0 Hz, 2H, Ar—H), 7.97-7.99 (d, J=10.0 Hz, 1H, Ar—H), 8.47 (s, 1H, Ar—H), 8.84-8.85 (d, J=5.0 Hz, 1H, Ar—H); $^{13}$C NMR (CDCl$_3$): δ 45.91, 51.52, 110.47, 122.55, 124.47, 124.73, 126.89, 127.54, 129.20, 129.73, 131.84, 134.03, 140.01, 147.36, 151.09, 156.58; ES-MS m/z 457 [M+H]$^+$; Anal. Calcd for C$_{20}$H$_{17}$ClF$_3$N$_3$O$_2$S: C, 52.69; H, 3.76; N, 9.22. found: C, 52.71; H, 3.74; N, 9.20.

4-[4-(Toluene-4-sulfonyl)-piperazin-1-yl]-7-trifluoromethyl-quinoline (8) VR-39

Creamy white solid; 74% yield; mp 126-128° C.; IR (KBr, cm$^{-1}$): 1165.2 (SO$_2$); $^1$H NMR (500 MHz, CDCl$_3$): δ 2.49 (s, 3H, CH$_3$), 3.35 (s, 8H, N(CH$_2$CH$_2$)$_2$N), 6.96-6.97 (d, J=5.0 Hz, 1H, Ar—H), 7.42-7.43 (d, J=10.0 Hz, 1H, Ar—H), 7.61-7.62 (d, J=5.0 Hz, 1H, Ar—H), 7.74-7.76 (d, J=10.0 Hz, 2H, Ar—H), 7.96-7.98 (d, J=10.0 Hz, 2H, Ar—H), 8.37 (s, 1H, Ar—H), 8.84-8.85 (d, J=5.0 Hz, 1H, Ar—H); $^{13}$C NMR (CDCl$_3$): δ 21.62, 46.00, 51.65, 110.74, 121.23, 124.53, 124.95, 127.89, 127.98, 128.02, 129.95, 131.22, 132.48, 144.17, 148.68, 152.21, 155.95; ES-MS m/z 436 [M+H]$^+$; Anal. Calcd for C$_{21}$H$_{20}$F$_3$N$_3$O$_2$S: C, 57.92; H, 4.63; N, 9.65. found: C, 57.89; H, 4.60; N, 9.62.

4-[4-(Biphenyl-4-sulfonyl)-piperazin-1-yl]-7-trifluoromethyl-quinoline (9) VR-43

White solid; 76% yield; mp 148-150° C.; IR (KBr, cm$^{-1}$) 1165.3 (SO$_2$); $^1$H NMR (500 MHz, CDCl$_3$): δ 3.37 (s, 4H, N(CH$_2$CH$_2$)$_2$N—Ar), 3.43 (s, 4H, N(CH$_2$CH$_2$)$_2$N—Ar), 6.97-6.98 (d, J=5.0 Hz, 1H, Ar—H), 7.45-7.47 (d, J=10.0 Hz, 1H, Ar—H), 7.48-7.52 (m, 2H, Ar—H), 7.53-7.55 (d, J=10.0 Hz, 2H, Ar—H), 7.61-7.63 (d, J=10.0 Hz, 2H, Ar—H), 7.66-7.68 (d, J=10.0 Hz, 2H, Ar—H), 7.98-8.00 (d, J=10.0 Hz, 2H, Ar—H), 8.37 (s, 1H, Ar—H), 8.85-8.86 (d, J=5.0 Hz, 1H, Ar—H); $^{13}$C NMR (CDCl$_3$): δ 45.99, 51.52, 110.78, 121.27, 124.53, 124.96, 127.35, 127.91, 128.05, 128.38, 128.72, 129.30, 130.97, 134.06, 139.08, 146.18, 148.73, 152.24, 155.91; ES-MS m/z 499 [M+H]$^+$; Anal. Calcd for C$_{26}$H$_{22}$F$_3$N$_3$O$_2$S: C, 62.77; H, 4.46; N, 8.45. found: C, 62.77; H, 4.46; N, 8.45.

4-[4-(2,4-Dichloro-benzenesulfonyl)-piperazin-1-yl]-7-trifluoromethyl-quinoline (10) VR-45

White solid; 70% yield; mp 137-139° C.; IR (KBr, cm$^{-1}$): 1169.8 (SO$_2$); $^1$H NMR (500 MHz, CDCl$_3$): δ 3.29 (s, 4H, N(CH$_2$CH$_2$)$_2$N—Ar), 3.63 (s, 4H, N(CH$_2$CH$_2$)$_2$N—Ar), 6.97-6.98 (d, J=5.0 Hz, 1H, Ar—H), 7.44-7.46 (d, J=5.0 Hz, 1H, Ar—H), 7.61 (s, 1H, Ar—H), 7.66-7.68 (d, J=10.0 Hz, 1H, Ar—H), 8.08-8.10 (d, J=10.0 Hz, 2H, Ar—H), 8.38 (s, 1H, Ar—H), 8.85-8.86 (d, J=5.0 Hz, 1H, Ar—H); $^{13}$C NMR (CDCl$_3$): δ 45.72, 52.00, 110.86, 120.60, 121.39, 124.50, 124.94, 125.02, 127.11, 128.07, 132.15, 133.09, 133.34, 134.58, 139.93, 148.76, 152.23, 155.99; ES-MS m/z 491 [M+H]$^+$; Anal. Calcd for C$_{20}$H$_{16}$Cl$_2$F$_3$N$_3$O$_2$S: C, 48.99; H, 3.29; N, 8.57. found: C, 49.01; H, 3.31; N, 8.61.

4-(4-Methanesulfonyl-piperazin-1-yl)-7-trifluoromethyl-quinoline (11) VR-38

Pale yellowish white solid; 70% yield; mp 116-118° C.; IR (KBr, cm$^{-1}$): 1170.5 (SO$_2$); $^1$H NMR (500 MHz, CDCl$_3$): δ 2.91 (s, 3H, SO$_2$CH$_3$), 3.38 (s, 4H, N(CH$_2$CH$_2$)$_2$N—Ar), 3.59 (s, 4H, N(CH$_2$CH$_2$)$_2$N—Ar), 7.01-7.02 (d, J=5.0 Hz, 1H, Ar—H), 7.70-7.71 (d, J=5.0 Hz, 1H, Ar—H), 8.11-8.13 (d, J=10.0 Hz, 1H, Ar—H), 8.41 (s, 1H, Ar—H), 8.88-8.89 (d, J=5.0 Hz, 1H, Ar—H); $^{13}$C NMR (CDCl$_3$): δ 34.94, 45.83, 51.79, 110.90, 121.40, 124.95, 125.04, 128.11, 131.06, 131.32, 148.79, 152.27, 155.94; ES-MS m/z 360 [M+H]$^+$; Anal. Calcd for C$_{15}$H$_{16}$F$_3$N$_3$O$_2$S: C, 50.13; H, 4.49; N, 11.69. found: C, 50.15; H, 4.51; N, 11.66.

4-[4-(2,4-Dinitro-benzenesulfonyl)-piperazin-1-yl]-7-trifluoromethyl-quinoline (12) VR-42

Yellow solid; 66% yield; mp 178-180° C.; IR (KBr, cm$^{-1}$): 1160.3 (SO$_2$); $^1$H NMR (500 MHz, CDCl$_3$): δ 3.36 (s, 4H, N(CH$_2$CH$_2$)$_2$N—Ar), 3.71 (s, 4H, N(CH$_2$CH$_2$)$_2$N—Ar), 6.99-7.00 (d, J=5.0 Hz, 1H, Ar—H), 7.68-7.70 (d, J=10.0 Hz, 1H, Ar—H), 8.06-8.07 (d, J=5.0 Hz, 1H, Ar—H), 8.31-8.33 (d, J=10.0 Hz, 1H, Ar—H), 8.55-8.57 (d, J=10.0 Hz, 1H, Ar—H), 8.57-8.59 (d, J=10.0 Hz, 1H, Ar—H), 8.62 (s, 1H, Ar—H), 8.87-8.88 (d, J=5.0 Hz, 1H, Ar—H); $^{13}$C NMR (CDCl$_3$): δ 46.15, 51.91, 110.97, 119.53, 121.54, 124.31, 124.58, 124.89, 124.96, 126.24, 128.15, 132.78, 137.07, 148.41, 148.77, 150.03, 152.23, 155.70; ES-MS m/z 512 [M+H]$^+$; Anal. Calcd for C$_{20}$H$_{16}$F$_3$N$_5$O$_6$S: C, 46.97; H, 3.15; N, 13.69. found: C, 46.94; H, 3.17; N, 13.66.

Dimethyl-{5-[4-(7-trifluoromethyl-quinolin-4-yl)-piperazine-1-sulfonyl]-naphthalen-1-yl}-amine (13) VR-44

Pale yellowish white solid; 69% yield; mp 98-100° C.; IR (KBr, cm$^{-1}$): 1170.8 (SO$_2$); $^1$H NMR (500 MHz, CDCl$_3$): δ 2.91 (s, 6H, N(CH$_3$)$_2$), 3.28 (s, 4H, N(CH$_2$CH$_2$)$_2$N—Ar), 3.55 (s, 4H, N(CH$_2$CH$_2$)$_2$N—Ar), 6.92-6.93 (d, J=5.0 Hz, 1H, Ar—H), 7.24-7.25 (d, J=5.0 Hz, 1H, Ar—H), 7.60-7.63 (m, 3H, Ar—H), 7.98-8.00 (d, J=10.0 Hz, 1H, Ar—H), 8.30-8.32 (d, J=10.0 Hz, 1H, Ar—H), 8.36 (s, 1H, Ar—H), 8.47-8.48 (d, J=5.0 Hz, 1H, Ar—H), 8.64-8.65 (d, J=5.0 Hz, 1H, Ar—H), 8.82-8.83 (d, J=5.0 Hz, 1H, Ar—H); $^{13}$C NMR (CDCl$_3$): δ 45.45, 45.51, 51.78, 110.72, 115.38, 119.50, 121.27, 123.25, 124.56, 124.93, 124.98, 127.97, 128.28, 130.17, 130.47, 130.90, 131.09, 131.22, 132.51, 148.71, 151.94, 152.18, 156.02; ES-MS m/z 516 [M+H]$^+$; Anal. Calcd for C$_{26}$H$_{25}$F$_3$N$_4$O$_2$S: C, 60.69; H, 4.90; N, 10.89. found: C, 60.65; H, 4.93; N, 10.87.

3-[4-(7-Trifluoromethyl-quinolin-4-yl)-piperazine-1-sulfonyl]-thiophene-2-carboxylic acid methyl ester (14) VR-46

White solid; 68% yield; mp 117-119° C.; IR (KBr, cm$^{-1}$): 1165.6 (SO$_2$); $^1$H NMR (500 MHz, CDCl$_3$): δ 3.32 (s, 4H, N(CH$_2$CH$_2$)$_2$N—Ar), 3.68 (s, 4H, N(CH$_2$CH$_2$)$_2$N—Ar), 3.91 (s, 3H, COOCH$_3$), 6.96-6.97 (d, J=5.0 Hz, 1H, Ar—H), 7.54-7.58 (dd, J$_1$=10.0 Hz, J$_2$=5.0 Hz, 2H, Ar—H), 7.64-7.66 (d, J=10.0 Hz, 1H, Ar—H), 8.05-8.07 (d, J=10.0 Hz, 1H, Ar—H), 8.05-8.07 (d, J=10.0 Hz, 1H, Ar—H), 8.37 (s, 1H, Ar—H), 8.83-8.84 (d, J=5.0 Hz, 1H, Ar—H); $^{13}$C NMR (CDCl$_3$): δ 46.09, 52.01, 53.13, 110.74, 121.25, 122.78, 124.99, 127.90, 129.37, 130.98, 131.24, 131.42, 134.07, 140.42, 148.59, 152.31, 156.01, 159.93; ES-MS m/z 487 [M+H]$^+$; Anal. Calcd for C$_{20}$H$_{18}$F$_3$N$_3$O$_4$S$_2$: C, 49.48; H, 3.74; N, 8.66. found: C, 49.52; H, 3.77; N, 8.68.

General Synthesis of N$^1$-(7-substituted-quinolin-4-yl)-propane-1,3-diamine (36, 37)

A mixture of 7-substituted-4-chloroquinoline (32 or 33) (20.50 mmol) and propane-1,3-diamine (50 mmol) was heated slowly to 80° C. over 1 hour while stirring. The temperature was then increased to 130° C. where it was kept for 6 hours while stirring continuously. The reaction mixture was cooled to room temperature and taken up in dichloromethane. The organic layer was washed with 5% aq. NaHCO$_3$, followed by washing with water and then with brine. The organic layer was dried over anhydrous MgSO$_4$ and solvent was removed under reduced pressure, and the residue was then precipitated by addition of 80:20 hexane:chloroform.

N$^1$-(7-Chloroquinolin-4-yl)-propane-1,3-diamine (36)

Yellowish white solid; 88% yield; mp 96-98° C.; IR (KBr, cm$^{-1}$): 3328.7; 2236.7; 1587.5; 1216.4; $^1$H NMR (500 MHz, CDCl$_3$): δ 1.89-1.92 (m, 2H, CH$_2$), 2.73 (br s, 2H, NH$_2$ D$_2$O-exchangeable), 3.02-3.06 (m, 2H, CH$_2$), 3.35-3.42 (m, 2H, CH$_2$), 6.29 (d, J=5.00 Hz, 1H, 3H quinoline), 7.28 (d, J=10.0 Hz, 1H, 6H quinoline), 7.45 (br s, 1H, NH D$_2$O-exchangeable), 7.70 (d, J=10.0 Hz, 1H, 5H quinoline), 7.91 (d, J=5.0 Hz, 1H, 8H quinoline), 8.47 (d, J=5.0 Hz, 1H, 2H quinoline); $^{13}$C NMR (CDCl$_3$): δ 29.81, 37.97, 40.06, 97.35, 116.56, 122.73, 123.01, 126.58, 132.70, 148.09, 149.35, 150.78; FAB-MS m/z 236 [M+H]$^+$; Anal. Calcd for C$_{12}$H$_{14}$ClN$_3$: C, 61.15; H, 5.99; N, 17.83. found: C, 61.15; H, 6.00; N, 17.91.

N$^1$-(7-Trifluoromethyl-quinolin-4-yl)-propane-1,3-diamine (37)

White solid; 86% yield; mp 108-110° C.; IR (KBr, cm$^{-1}$): 3332.9; 2231.9; 1584.5; 1212.4; $^1$H NMR (500 MHz, CDCl$_3$): δ 1.74 (br s, 2H, NH$_2$ D$_2$O-exchangeable), 1.92-1.94 (m, 2H, CH$_2$), 3.02-3.06 (m, 2H, CH$_2$), 3.40-3.44 (m, 2H, CH$_2$), 6.53 (d, J=5.0 Hz, 1H, Ar—H), 7.55 (d, J=10.0 Hz, 1H, Ar—H), 7.68 (br s, 1H, NH D$_2$O-exchangeable), 7.92 (d, J=5.0 Hz, 1H, Ar—H), 8.29 (s, 1H, Ar—H), 8.63 (d, J=10.0 Hz, 1H, Ar—H); $^{13}$C NMR (CDCl$_3$): δ 29.75, 41.56, 43.89, 99.22, 119.75, 120.86, 121.82, 123.03, 125.20, 127.38, 147.70, 150.31, 152.34; ES-MS m/z 270 [M+H]$^+$; Anal. Calcd for C$_{13}$H$_{14}$F$_3$N$_3$: C, 57.99; H, 5.24; N, 15.61. found: C, 58.01; H, 5.22; N, 15.65.

General synthesis of N-[3-(7-Chloro-quinolin-4-ylamino)-propyl]-alkene/arylene/heteroalkene sulfonamide (15-31) (Table I)

To a solution of compound N$^1$-(7-substituted-quinolin-4-yl)-propane-1,3-diamine (3.20 mmol) in anhydrous THF (25 mL) under a nitrogen atmosphere triethylamine (0.44 mL, 3.20 mmol) was added. The mixture was cooled to below 0° C. Alkyl/aryl/heteroalkyl sulfonyl chloride (3.20 mmol) was added slowly, keeping the temperature below 5° C., and the reaction was stirred in an ice bath for 1 h. After dilution with saturated NaHCO$_3$ solution (20 mL), the reaction was extracted with ether (2×). The organic extracts were dried over Na$_2$SO$_4$, filtered and evaporated to leave crude compound. The crude product was purified through chromatography on silica gel, eluting with chloroform-methanol.

N-[3-(7-Chloro-quinolin-4-ylamino)-propyl]-methanesulfonamide (15) VR-21

White solid; 76% yield; IR (KBr, cm$^{-1}$) 3320.5 (NH); 1185.3 (SO$_2$); $^1$H NMR (500 MHz, CDCl$_3$): δ 1.88-1.92 (m, 2H, CH$_2$), 2.86 (s, 3H, SO$_2$CH$_3$), 3.24-3.27 (m, 2H, CH$_2$), 3.42-3.46 (m, 2H, CH$_2$), 6.37 (d, J=5.0 Hz, 1H, Ar—H), 7.00 (br s, 1H, NH), 7.08 (br s, 1H, NH), 7.27 (d, J=5.0 Hz, 1H, Ar—H), 7.72 (d, Hz, J=10.0 Hz, 1H, Ar—H), 8.11 (d, J=10.0 Hz, 1H, Ar—H), 8.35 (d, J=5.0 Hz, 1H, Ar—H); $^{13}$C NMR (CDCl$_3$): δ 28.36, 39.64, 39.97, 47.81, 98.75, 117.80, 123.70, 124.42, 127.92, 134.21, 149.32, 150.45, 151.95; ES-MS m/z 315 [M+H]$^+$; Anal. Calcd for C$_{13}$H$_{16}$ClN$_3$O$_2$S: C, 49.76; H, 5.14; N, 13.39. found: C, 49.71; H, 5.10; N, 13.41.

N-[3-(7-Chloro-quinolin-4-ylamino)-propyl]-4-methyl-benzenesulfonamide (16) VR-26

Creamy white solid; 74% yield; IR (KBr, cm$^{-1}$): 3290.6 (NH); 1175.2 (SO$_2$); $^1$H NMR (500 MHz, CDCl$_3$): δ 1.87-1.97 (m, 2H, CH$_2$), 2.27 (s, 3H, CH$_3$), 3.06-3.13 (m, 2H, CH$_2$), 3.52-3.56 (m, 2H, CH$_2$), 5.69 (br s, 1H, NH D$_2$O-exchangeable), 6.34 (d, J=5.0 Hz, 1H, Ar—H), 7.31-7.38 (m, 4H, Ar—H), 7.40 (d, J=5.0 Hz, 1H, Ar—H), 7.74 (br s, 1H, NH D$_2$O-exchangeable), 7.76 (d, J=10.0 Hz, 1H, Ar—H), 7.97 (d, J=10.0 Hz, 1H, Ar—H), 8.48 (d, J=5.0 Hz, 1H, Ar—H); ES-MS m/z 391 [M+H]$^+$; Anal. Calcd for C$_{19}$H$_{20}$ClN$_3$O$_2$S: C, 58.53; H, 5.17; N, 10.78. found: C, 58.49; H, 5.19; N, 10.81.

N-[3-(7-Chloro-quinolin-4-ylamino)-propyl]-2,4-dinitro-benzenesulfonamide (17) VR-27

Yellow solid; 68% yield; mp 238-240° C.; IR (KBr, cm$^{-1}$): 3310.6 (NH); 1185.3 (SO$_2$); $^1$H NMR (500 MHz, CDCl$_3$): δ 2.05-5.08 (m, 2H, CH$_2$), 2.29 (br s, 1H, NH D$_2$O exchangeable), 3.29-3.32 (m, 2H, CH$_2$), 3.61-3.65 (m, 2H, CH$_2$), 6.41 (d, J=5.0 Hz, 1H, Ar—H), 7.16 (d, J=5.0 Hz, 1H, Ar—H), 7.28 (br s, 1H, NH D$_2$O exchangeable), 7.33 (d, J=10.0 Hz, 2H, Ar—H), 7.75 (s, 1H, Ar—H), 8.12 (d, J=10.0 Hz, 1H, Ar—H), 8.36 (d, J=5.0 Hz, 1H, Ar—H), 8.89 (s, 1H, Ar—H); $^{13}$C NMR (CDCl$_3$): δ 27.12, 41.13, 41.85, 98.92, 115.26, 117.89, 124.00, 124.15, 124.44, 127.80, 130.21, 131.41, 135.35, 148.55, 149.26, 150.50, 151.93, 152.95; ES-MS m/z 467 [M+H]$^+$; Anal. Calcd for C$_{18}$H$_{16}$ClN$_5$O$_6$S: C, 46.41; H, 3.46; N, 15.03. found: C, 46.37; H, 3.49; N, 15.29.

N-(3-(7-Chloroquinolin-4-ylamino)propyl)-3-nitrobenzenesulfonamide (18) VR-32

Pale yellowish white solid; 73% yield; IR (KBr, cm$^{-1}$): 3280.9 (NH); 1190.7 (SO$_2$); $^1$H NMR (500 MHz, DMSOd$_6$+CDCl$_3$): δ 1.80-1.86 (m, 2H, CH$_2$), 2.95-2.98 (m, 2H, CH$_2$), 3.19 (br s, 1H, NH), 3.26-3.30 (m, 2H, CH$_2$), 6.31 (d, J=5.0

Hz, 1H, Ar—H), 6.77 (br s, 1H, NH), 7.26 (d, J=10.0 Hz, 1H, Ar—H), 7.53 (s, 1H, Ar—H), 7.64 (d, J=10.0 Hz, 1H, Ar—H), 7.81-7.86 (m, 2H, Ar—H), 8.09 (d, J=10.0 Hz, 1H, Ar—H), 8.25 (d, J=10.0 Hz, 1H, Ar—H), 8.62 (s, 1H, Ar—H); $^{13}$C NMR (DMSOd$_6$+CDCl$_3$): δ 27.07, 39.93, 39.98, 97.98, 117.00, 121.23, 122.73, 123.77, 125.99, 127.25, 129.97, 131.91, 133.60, 142.06, 147.43, 148.53, 149.58, 151.16; ES-MS m/z 422 [M+H]$^+$; Anal. Calcd for C$_{18}$H$_{17}$ClN$_4$O$_4$S: C, 51.37; H, 4.07; N, 13.31. found: C, 51.33; H, 4.09; N, 13.29.

4-Chloro-N-(3-(7-chloroquinolin-4-ylamino)propyl)
benzenesulfonamide (19) VR-33

Pale yellowish white solid; 72% yield; mp 117-119° C.; IR (KBr, cm$^{-1}$): 3300.7 (NH); 1189.8 (SO$_2$); $^1$H NMR (500 MHz, CDCl$_3$): δ 1.79-1.83 (m, 2H, CH$_2$), 2.89-2.92 (m, 2H, CH$_2$), 3.76-3.79 (m, 2H, CH$_2$), 6.24 (d, J=5.0 Hz, 1H, Ar—H), 6.97 (br s, 1H, NH D$_2$O exchangeable), 7.27 (d, J=10.0 Hz, 1H, Ar—H), 7.42 (d, J=10.0 Hz, 1H, Ar—H), 7.42 (d, J=10.0 Hz, 2H, Ar—H), 7.70 (d, J=10.0 Hz, 1H, Ar—H), 7.73 (d, J=10.0 Hz, 1H, Ar—H), 7.87 (d, J=5.0 Hz, 1H, Ar—H); 7.95 (br s, 1H, NH D$_2$O exchangeable), 8.33 (s, 1H, Ar—H); $^{13}$C NMR (CDCl$_3$): δ 28.36, 40.51, 41.50, 99.05, 117.94, 124.49, 124.58, 127.95, 128.83, 129.63, 133.81, 137.20, 140.57, 149.54, 150.43, 152.35; ES-MS m/z 411 [M+H]$^+$; Anal. Calcd for C$_{18}$H$_{17}$O$_2$N$_3$O$_2$S: C, 52.69; H, 4.18; N, 10.24. found: C, 52.71; H, 4.15; N, 10.22.

Biphenyl-4-sulfonic acid [3-(7-chloro-quinolin-4-
ylamino)-propyl]-amide (20) VR-52

Pale yellowish white solid; 70% yield; mp 116-118° C.; IR (KBr, cm$^{-1}$): 3260.9 (NH); 1180.5 (SO$_2$); $^1$H NMR (500 MHz, CDCl$_3$): δ 1.82-1.85 (m, 2H, CH$_2$), 2.89-2.94 (m, 2H, CH$_2$), 3.48-3.52 (m, 2H, CH$_2$), 6.30 (d, J=5.0 Hz, 1H, Ar—H), 6.92 (br s, 1H, NH D$_2$O exchangeable), 7.28 (d, J=5.0 Hz, 1H, Ar—H), 7.32 (d, J=10.0 Hz, 1H, Ar—H), 7.38 (d, J=10.0 Hz, 1H, Ar—H), 7.49 (d, J=10.0 Hz, 1H, Ar—H), 7.54 (s, 1H, Ar—H), 7.59 (d, J=10.0 Hz, 2H, Ar—H), 7.63 (d, J=10.0 Hz, 2H, Ar—H), 7.70 (s, 1H, Ar—H), 7.77 (br s, 1H, NH D$_2$O exchangeable), 7.82 (d, J=10.0 Hz, 1H, Ar—H), 8.02 (d, J=10.0 Hz, 1H, Ar—H), 8.30 (d, J=5.0 Hz, 1H, Ar—H); $^{13}$C NMR (CDCl$_3$): δ 22.55, 27.69, 40.62, 98.57, 117.42, 123.29, 124.93, 127.04, 127.17, 127.37, 127.51, 128.25, 128.41, 129.05, 134.99, 139.14, 144.91, 147.91, 150.67, 150.87; ES-MS m/z 453 [M+H]$^+$; Anal. Calcd for C$_{24}$H$_{22}$ClN$_3$O$_2$S: C, 63.78; H, 4.91; N, 9.30. found: C, 63.74; H, 4.89; N, 9.28.

2,4-Dichloro-N-[3-(7-chloro-quinolin-4-ylamino)-
propyl]-benzenesulfonamide (21) VR-66

Pale yellowish white solid; 68% yield; mp 145-147° C.; IR (KBr, cm$^{-1}$): 3295.7 (NH); 1192.3 (SO$_2$); $^1$H NMR (500 MHz, CDCl$_3$): δ 1.75-1.78 (m, 2H, CH$_2$), 2.99-3.02 (m, 2H, CH$_2$), 3.18-3.22 (m, 2H, CH$_2$), 6.36 (d, J=5.0 Hz, 1H, Ar—H), 6.50 (br s, 1H, NH D$_2$O exchangeable), 7.43 (d, J=10.0 Hz, 1H, Ar—H), 7.46 (br s, 1H, NH D$_2$O exchangeable), 7.50 (d, J=10.0 Hz, 1H, Ar—H), 7.74 (d, J=10.0 Hz, 2H, Ar—H), 7.91 (d, J=5.0 Hz, 1H, Ar—H), 8.20 (d, J=10.0 Hz, 1H, Ar—H), 8.37 (d, J=5.0 Hz, 1H, Ar—H); $^{13}$C NMR (CDCl$_3$): δ 28.39, 39.45, 41.30, 99.00, 117.90, 124.47, 124.51, 124.60, 127.89, 128.05, 131.51, 132.23, 132.33, 132.54, 133.83, 149.47, 150.43, 152.29; ES-MS m/z 446 [M+H]$^+$; Anal. Calcd for C$_{18}$H$_{16}$Cl$_3$N$_3$O$_2$S: C, 48.61; H, 3.63; N, 9.45. found: C, 48.59; H, 3.65; N, 9.43.

N-(3-(7-Chloroquinolin-4-ylamino)propyl)thio-
phene-3-sulfonamide-2-carbomethoxy ester (22)
VR-67

White solid; 72% yield; IR (KBr, cm$^{-1}$): 3310.5 (NH); 1187.5 (SO$_2$); $^1$H NMR (500 MHz, CDCl$_3$): δ 1.98-2.01 (m, 2H, CH$_2$), 3.06-3.12 (m, 2H, CH$_2$), 3.59-3.62 (m, 2H, CH$_2$), 3.98 (s, 3H, COOCH$_3$), 6.41 (d, J=5.0 Hz, 1H, Ar—H), 6.64 (br s, 1H, NH D$_2$O exchangeable), 6.75 (br s, 1H, NH D$_2$O exchangeable), 7.38 (d, J=5.0 Hz, 1H, Ar—H), 7.53 (d, J=10.0 Hz, 1H, Ar—H), 7.56 (d, J=10.0 Hz, 1H, Ar—H), 7.97 (s, 1H, Ar—H), 8.00 (d, J=10.0 Hz, 1H, Ar—H), 8.44 (d, J=5.0 Hz, 1H, Ar—H); $^{13}$C NMR (CDCl$_3$): δ 27.94, 39.84, 40.55, 53.31, 98.37, 109.87, 117.89, 122.57, 126.05, 126.11, 130.67, 130.72, 130.92, 130.98, 131.17, 131.22, 144.46, 161.18; ES-MS m/z 441 [M+H]$^+$; Anal. Calcd for C$_{18}$H$_{18}$ClN$_3$O$_4$S$_2$: C, 49.14; H, 4.12; N, 9.55. found: C, 49.12; H, 4.09; N, 9.57.

N-[3-(7-Trifluoromethyl-quinolin-4-ylamino)-pro-
pyl]-methanesulfonamide (23) VR-57

White solid; 69% yield; IR (KBr, cm$^{-1}$): 3305.4 (NH); 1174.9 (SO$_2$); mp 171-173° C.; $^1$H NMR (500 MHz, CDCl$_3$): δ 1.88-1.93 (m, 2H, CH$_2$), 2.85 (s, 3H, SO$_2$CH$_3$), 3.03-3.13 (m, 2H, CH$_2$), 3.40-3.46 (m, 2H, CH$_2$), 6.43 (d, J=5.0 Hz, 1H, Ar—H), 6.82 (br s, 1H, NH D$_2$O-exchangeable), 7.01 (br s, 1H, NH D$_2$O-exchangeable), 7.47 (d, J=5.0 Hz, 1H, Ar—H), 8.06 (s, 1H, Ar—H), 8.18 (d, J=10.0 Hz, 1H, Ar—H), 8.47 (d, J=5.0 Hz, 1H, Ar—H); $^{13}$C NMR (CDCl$_3$): δ 28.07, 39.63, 40.62, 99.95, 119.31, 121.09, 122.95, 123.10, 125.26, 126.94, 130.10, 147.81, 150.10, 152.24; ES-MS m/z 348 [M+H]$^+$; Anal. Calcd for C$_{14}$H$_{16}$F$_3$N$_3$O$_2$S: C, 48.41; H, 4.64; N, 12.10. found: C, 48.39; H, 4.67; N, 12.12.

4-Methyl-N-[3-(7-trifluoromethyl-quinolin-4-
ylamino)-propyl]-benzenesulfonamide (24) VR-56

Pale yellowish white solid; 65% yield; IR (KBr, cm$^{-1}$): 3290.6 (NH); 1189.8 (SO$_2$); mp 77-79° C.; $^1$H NMR (500 MHz, CDCl$_3$): δ 1.91-1.95 (m, 2H, CH$_2$), 2.41 (s, 3H, CH$_3$), 3.08-3.13 (m, 2H, CH$_2$), 3.49-3.52 (m, 2H, CH$_2$), 6.24 (br s, 1H, NH), 6.33 (d, J=5.0 Hz, 1H, Ar—H), 6.55 (br s, 1H, NH), 7.24 (d, J=10.0 Hz, 2H, Ar—H), 7.43 (dd, J$_1$=5.0 Hz, J$_2$=10.0 Hz, 1H, Ar—H), 7.75 (d, J=10.0 Hz, 2H, Ar—H), 7.98 (d, J=10.0 Hz, 1H, Ar—H), 8.12 (s, 1H, Ar—H), 8.47 (d, J=5.0 Hz, 1H, Ar—H); ES-MS m/z 424 [M+H]$^+$; Anal. Calcd for C$_{20}$H$_{20}$F$_3$N$_3$O$_2$S: C, 56.73; H, 4.76; N, 9.92. found: C, 56.70; H, 4.72; N, 9.89.

2,4-Dinitro-N-[3-(7-trifluoromethyl-quinolin-4-
ylamino)-propyl]-benzenesulfonamide (25) VR-59

Yellow solid; 66% yield; mp 198-200° C.; IR (KBr, cm$^{-1}$): 3275.3 (NH); 1170.9 (SO$_2$); $^1$H NMR (500 MHz, CDCl$_3$): δ 2.04-2.08 (m, 2H, CH$_2$), 3.59-3.63 (m, 2H, CH$_2$), 3.69-3.72 (m, 2H, CH$_2$), 6.56 (d, J=5.0 Hz, 1H, Ar—H), 7.22 (d, J=10.0 Hz, 1H, Ar—H), 7.55 (br s, 1H, NH D$_2$O exchangeable), 7.60 (d, J=10.0 Hz, 1H, Ar—H), 8.05 (br s, 1H, NH D$_2$O exchangeable), 8.19 (d, J=10.0 Hz, 1H, Ar—H), 8.40 (d, J=10.0 Hz, 1H, Ar—H), 8.47 (d, J=5.0 Hz, 1H, Ar—H), 8.86 (d, J=5.0 Hz, 1H, Ar—H), 8.93 (s, 1H, Ar—H); $^{13}$C NMR (CDCl$_3$): δ 27.05, 41.16, 67.50, 100.06, 115.45, 119.20, 121.32, 123.43, 124.02, 124.15, 125.60, 126.80, 130.19, 130.26, 135.26, 147.92, 148.46, 150.18, 152.54; ES-MS m/z 500 [M+H]$^+$; Anal. Calcd for $C_{19}H_{16}F_3N_5O_6S$: C, 45.69; H, 3.23; N, 14.02. found: 45.71; H, 3.26; N, 14.06.

3-Nitro-N-[3-(7-trifluoromethyl-quinolin-4-ylamino)-propyl]-benzenesulfonamide (26) VR-58

Pale yellowish white solid; 69% yield; mp 98-100° C.; IR (KBr, cm$^{-1}$): 3295.0 (NH); 1180.8 (SO$_2$); $^1$H NMR (500 MHz, CDCl$_3$): δ 1.62-1.68 (m, 2H, CH$_2$), 2.62-2.68 (m, 2H, CH$_2$), 3.03-3.13 (m, 2H, CH$_2$), 6.11 (d, J=5.0 Hz, 1H, Ar—H), 6.43 (br s, 1H, NH D$_2$O exchangeable), 7.23 (d, J=10.0 Hz, 1H, Ar—H), 7.29 (s, 1H, Ar—H), 7.35 (d, J=10.0 Hz, 1H, Ar—H), 7.64 (br s, 1H, NH D$_2$O exchangeable), 7.76 (s, 1H, Ar—H), 7.87 (d, J=10.0 Hz, 1H, Ar—H), 8.08 (d, J=10.0 Hz, 1H, Ar—H), 8.20 (d, J=5.0 Hz, 1H, Ar—H), 8.42 (s, 1H, Ar—H); ES-MS m/z 455 [M+H]$^+$; Anal. Calcd for $C_{19}H_{17}F_3N_4O_4S$: C, 50.22; H, 3.77; N, 12.33. found: C, 50.18; H, 3.81; N, 12.29.

4-Chloro-N-[3-(7-trifluoromethyl-quinolin-4-ylamino)-propyl]-benzenesulfonamide (27) VR-60

Pale yellowish white solid; 66% yield; mp 70-72° C.; IR (KBr, cm$^{-1}$): 3275.5 (NH); 1170.3 (SO$_2$); $^1$H NMR (500 MHz, CDCl$_3$): δ 1.95-1.98 (m, 2H, CH$_2$), 3.11-3.15 (m, 2H, CH$_2$), 3.53-3.56 (m, 2H, CH$_2$), 6.47 (d, J=5.0 Hz, 1H, Ar—H), 6.68 (br s, 1H, NH D$_2$O exchangeable), 7.74 (d, J=10.0 Hz, 2H, Ar—H), 7.50 (d, J=10.0 Hz, 1H, Ar—H), 7.66 (br s, 1H, NH D$_2$O exchangeable), 7.75 (d, J=10.0 Hz, 2H, Ar—H), 8.05 (d, J=10.0 Hz, 1H, Ar—H), 8.09 (s, 1H, Ar—H), 8.44 (d, J=5.0 Hz, 1H, Ar—H); $^{13}$C NMR (CDCl$_3$): δ 27.79, 40.01, 40.56, 99.36, 120.11, 120.66, 122.14, 124.45, 127.45, 128.37, 128.55, 128.59, 128.77, 129.51, 129.58, 138.36, 139.30, 145.31, 150.04, 150.65; ES-MS m/z 445 [M+H]$^+$; Anal. Calcd for $C_{19}H_{17}ClF_3N_3O_2S$: C, 51.41; H, 3.86; N, 9.47. found: C, 51.44; H, 3.89; N, 9.50.

5-Dimethylamino-naphthalene-1-sulfonic acid [3-(7-trifluoromethyl-quinolin-4-ylamino)-propyl]-amide (28) VR-63

Pale yellowish white solid; 65% yield; mp 199-201° C.; IR (KBr, cm$^{-1}$): 3275.6 (NH); 1180.9 (SO$_2$); $^1$H NMR (500 MHz, CDCl$_3$): δ 1.49-1.55 (m, 2H, CH$_2$), 2.28 (br s, 1H, NH D$_2$O exchangeable), 2.54 (s, 6H, N(CH$_3$)$_2$), 2.72-2.76 (m, 2H, CH$_2$), 3.02-3.06 (m, 2H, CH$_2$), 5.98 (d, J=5.0 Hz, 1H, Ar—H), 6.40 (br s, 1H, NH D$_2$O exchangeable), 6.85 (d, J=10.0 Hz, 1H, Ar—H), 7.15-7.28 (m, 4H, Ar—H), 7.84-7.87 (m, 2H, Ar—H), 8.07 (d, J=10.0 Hz, 1H, Ar—H), 8.14 (s, 1H, Ar—H), 8.15 (d, J=5.0 Hz, 1H, Ar—H); $^{13}$C NMR (CDCl$_3$): δ 27.35, 39.39, 40.39, 45.11, 99.31, 114.84, 118.90, 119.31, 119.38, 120.67, 122.50, 122.91, 126.44, 127.74, 128.53, 129.35, 129.55, 129.81, 130.26, 135.46, 147.19, 149.82, 151.58, 151.63; ES-MS m/z 503 [M+H]$^+$; Anal. Calcd for $C_{25}H_{25}F_3N_4O_2S$: C, 59.75; H, 5.01; N, 11.15. found: C, 59.77; H, 5.04; N, 11.11.

Biphenyl-4-sulfonic acid [3-(7-trifluoromethyl-quinolin-4-ylamino)-propyl]-amide (29) VR-61

White solid; 72% yield; mp 110-112° C.; IR (KBr, cm$^{-1}$): 3310.5 (NH); 1185.6 (SO$_2$); $^1$H NMR (500 MHz, CDCl$_3$): δ 1.96-1.98 (m, 2H, CH$_2$), 3.21-3.23 (m, 2H, CH$_2$), 3.58-3.62 (m, 2H, CH$_2$), 5.70 (br s, 1H, NH D$_2$O exchangeable), 6.40 (d, J=5.0 Hz, 1H, Ar—H), 7.43-7.51 (m, 6H, Ar—H), 7.60 (br s, 1H, NH D$_2$O exchangeable), 7.64-7.66 (m, 2H, Ar—H), 7.86-7.90 (m, 3H, Ar—H), 8.27 (s, 1H, Ar—H), 8.55 (d, J=5.0 Hz, 1H, Ar—H); $^{13}$C NMR (CDCl$_3$): δ 27.90, 39.52, 40.53, 99.69, 120.25, 120.57, 121.17, 127.27, 127.44, 127.90, 127.95, 128.64, 129.11, 129.25, 138.19, 138.25, 139.04, 145.92, 147.63, 149.27, 152.08; ES-MS m/z 487 [M+H]$^+$; Anal. Calcd for $C_{25}H_{22}F_3N_3O_2S$: C, 61.84; H, 4.57; N, 8.65. found: C, 61.87; H, 4.55; N, 8.68.

2,4-Dichloro-N-[3-(7-trifluoromethyl-quinolin-4-ylamino)-propyl]-benzenesulfonamide (30) VR-62

White solid; 68% yield; mp 117-119° C.; IR (KBr, cm$^{-1}$): 3260.5 (NH); 1185.6 (SO$_2$); $^1$H NMR (500 MHz, CDCl$_3$): δ 1.94-1.97 (m, 2H, CH$_2$), 3.12-3.16 (m, 2H, CH$_2$), 3.54-3.58 (m, 2H, CH$_2$), 5.69 (br s, 1H, NH D$_2$O exchangeable), 6.10 (br s, 1H, NH D$_2$O exchangeable), 6.48 (d, J=5.0 Hz, 1H, Ar—H), 7.38 (d, J=10.0 Hz, 1H, Ar—H), 7.47 (d, J=10.0 Hz, 1H, Ar—H), 7.56 (d, J=10.0 Hz, 1H, Ar—H), 7.80 (d, J=10.0 Hz, 1H, Ar—H), 7.88 (d, J=10.0 Hz, 1H, Ar—H), 8.25 (s, 1H, Ar—H), 8.60 (d, J=5.0 Hz, 1H, Ar—H); $^{13}$C NMR (CDCl$_3$): δ 27.89, 39.43, 40.43, 99.75, 120.23, 120.49, 121.07, 127.30, 127.69, 127.72, 131.57, 132.16, 132.25, 132.33, 135.50, 139.88, 147.55, 149.22, 152.11; ES-MS m/z 479 [M+H]$^+$; Anal. Calcd for $C_{19}H_{16}Cl_2F_3N_3O_2S$: C, 47.71; H, 3.37; N, 8.79. found: C, 47.69; H, 3.39; N, 8.76.

N-(3-(7-Trifluoromethyl-quinolin-4-ylamino)propyl) thiophene-3-sulfonamide-2-carbomethoxy ester (31) VR-64

White solid; 70% yield; mp 137-139° C.; IR (KBr, cm$^{-1}$): 3305.6 (NH); 1189.8 (SO$_2$); $^1$H NMR (500 MHz, CDCl$_3$): δ 1.93-1.98 (m, 2H, CH$_2$), 3.12-3.16 (m, 2H, CH$_2$), 3.61-3.67 (m, 2H, CH$_2$), 3.98 (s, 3H, COOCH$_3$), 5.79 (br s, 1H, NH D$_2$O exchangeable), 6.50 (d, J=5.0 Hz, 1H, Ar—H), 6.55 (br s, 1H, NH D$_2$O exchangeable), 7.56 (d, J=5.0 Hz, 1H, Ar—H), 7.60 (d, J=5.0 Hz, 1H, Ar—H), 7.63 (d, J=10.0 Hz, 1H, Ar—H), 7.98 (d, J=5.0 Hz, 1H, Ar—H), 8.28 (s, 1H, Ar—H), 8.62 (d, J=5.0 Hz, 1H, Ar—H); $^{13}$C NMR (CDCl$_3$): δ 27.79, 39.94, 40.40, 53.31, 99.76, 120.19, 120.69, 121.11, 127.69, 130.74, 130.79, 131.12, 131.15, 144.51, 147.90, 149.26, 152.23, 161.26; ES-MS m/z 474 [M+H]$^+$; Anal. Calcd for $C_{19}H_{18}F_3N_3O_4S_2$: C, 48.20; H, 3.83; N, 8.87. found: C, 48.17; H, 3.81; N, 8.85.

SRB Assay

Antiproliferative effects were determined by a sulforhodamine B (SRB) based protocol. For a typical screening experiment, 5,000-10,000 cells were inoculated into 100 μl medium per well of a 96-well microtiter plate as described previously. Briefly, after the inoculation, the microtiter plate was incubated at 37° C., 5% CO$_2$, 95% air and 100% relative humidity for 24 h, prior to addition of experimental drugs. Some of the sample wells were fixed with 25 μl of 50% trichloroacetic acid (TCA) as a control of the cell population for each cell line at the time of drug addition (Tz). An aliquot of the frozen stock was thawed and diluted to the desired final maximum test-concentration with complete medium. Two to ten-fold serial dilutions were made to provide a total of seven drug concentrations (and a control [C]). Following addition of drugs, the culture plate was incubated for additional 48 h. Cells were fixed in situ by slowly adding 25 μl of ice-cold 50% (w/v) TCA (final concentration, 10% TCA), and were then incubated for 60 min at 4° C. The supernatant was discarded, and the plate was washed five times with tap water, followed by air-dry. 50 µl of SRB solution at 0.4% (w/v) in 1% acetic acid was added to each well, and the plate was incubated for >30 min at room temperature. Unbound SRB was removed by five washes with tap water, followed by air-drying. The cells "stained" with SRB were solubilized with 10 mM trizma base, and the absorbance was read on an automated plate reader at a wavelength of 515-564 nm. The relative growth rate (%) was calculated for each of the compound concentrations according to the following formula:

(Ti−Tz)/(C−Tz)×100

In the formula, time zero (Tz), control growth (C), and OD for different concentration of tested compounds (Ti). The $GI_{50}$ for each compound was obtained from a non-linear Sigmoidal dose-response (variable slope) curve which is fitted by GraphPad Prism™ v.4.03 software. Values were calculated for each of these parameters if the level of activity was reached. However, if the effect was not reached or was exceeded, the value for that parameter was expressed as greater or less than the maximum or minimum concentration tested.

Flow Cytometry

Cells ($2.0 \times 10^6$) were harvested by centrifugation at 1000 rpm on a bench-top centrifuge for 5 min, followed by fixation with ice-cold ethanol (70%) for 30 min to overnight at −20° C. The ethanol was then removed by centrifugation, and cells were resuspended in 1×PBS solution, followed by centrifuge. The cell pellet was then stained with PI master mix (100 µg/ml RNase A, 100 µg/ml PI, 0.3% Nonidet P-40 and 0.1% sodium citrate in distilled water) for 30 min at 37° C. DNA content was measured using a Beckmann Coulter Cytomics FC500™ (Beckman Coulter, Fullerton, Calif.), and the proportion of cells in G0/G1, S, and G2/M phases of cell cycle was calculated on the basis of DNA distribution histograms using CXP software.

Microscopy and Cell Staining

All immunocytochemistry experiments were visualized by confocal microscopy using a Zeiss 510 Meta laser scanning microscope (Carl Zeiss) equipped with a 63× objective lens, unless otherwise specified herein. Three lasers were utilized for excitation with the following band pass filter settings used for detection: Argon 488 nm (band pass 505-530), HeNe 543 nm (long pass 560) and 633 nm (long pass 650). All images were captured and analyzed using LSM 510 software included with the microscope (LSM Image Examiner™, Carl Zeiss).

The clonogenic assay was carried out as described in Santi and Lee (2011).[11]

Cell Synchronization

The synchronization at the G1/S border (more accurately at the beginning of S phase) was achieved by double thymidine block (DT). Briefly, exponentially growing cells are treated with 2.0 mM thymidine for 18 hours, followed by incubation for 11 hours in drug-free complete medium, by which time most cells are at mid-late G1 phase. The cells are then incubated for another 14 hours in 2.0 mM thymidine to arrest them at the G1/S border. To arrest cells at the G2/M phase, cells were maintained for 18 hours in complete medium containing nocodazole (50 ng/ml). Both these synchronization are reversible.

Proteasome Activity Assay

Exponentially growing HeLa S3 cells were plated on 96-well plates. After overnight incubation, the cells were treated with different concentrations of drugs for 6 hours or left untreated (control). At the end of 6 hours, proteasomes were extracted in 0.5% NP40 buffer, and equal amounts of samples were incubated with 25 µM of fluorogenic substrates purchased from Boston Biochem (Cambridge Mass.). (LRR-specific for trypsin-like activity, LLE-specific for caspase-like activity and SUVY-specific for chymotrypsin like activity) in black-bottom 96-well plates at 37° C. Fluorescence was monitored every 5 min at the wavelength of 360 nm (excitation) and 480 nm (emission). Chymotrypsin activity was also determined by a kit-based method (similar to described above) purchased from Caymen Biochem (Ann Arbor, Mich.), using a fluorogenic substrate specific for chymotrypsin activity.

Animal Studies

Mice and Cells.

Five-week-old female CD-1 and ATH490 (strain code 490) athymic nude mice were purchased from Charles River (Quebec, Canada). The MDA-MB231 human metastatic breast cancer cells were obtained from the American Tissue Culture Collection (ATCC, Manassas, Va., USA). Cells were maintained under humidified condition at 37° C. and 5% $CO_2$ in DMEM high glucose medium (ATCC) supplemented with 10% fetal bovine serum and antibiotics. All animal experiments, including animal handling, care, treatment and endpoint determination, were reviewed and approved by the Laurentian University Animal Care Committee (ACC) and carried out at Laurentian University Animal Care facility (Sudbury, Ontario, Canada)

Reagents.

For paclitaxel treatments, 40 mg/ml stock solution of paclitaxel (Sigma, Mo., USA) was prepared in DMSO. Just before administration to mice, the paclitaxel stock solution was diluted ten-fold in Dilution buffer containing 10% DMSO, 12.5% Cremophor™, 12.5% ethanol and 65% saline based diluent (0.9% sodium chloride, 5% polyethylene glycol, and 0.5% tween-80) (where said buffer is referred to herein as "vehicle"). Antibodies specific for Ki-67 and vascular endothelial growth factor ("VEGF") used in immunohistochemistry were purchased from Abcam (Toronto, Ontario, Canada). Alanine Transaminase ("ALT", SUP6001-c)/Aspartate Transaminase ("AST", SUP6002-c) color endpoint assay kits were purchased from ID Labs Biotechnology (London, Ontario, Canada). Elevation of ALT and AST levels in serum samples is used as an indicator of liver damage/injury.

Antitumor Activity.

To determine anti-tumor activity of VR-23 in an animal model, a xenograft model of human breast cancer cells in athymic nude mice was established. Exponentially growing MDA-MB231 cells were harvested and counted for inoculation into mice. Each mouse was subcutaneously injected at the flank with $10 \times 10^6$ cells in 0.2 ml ice cold 1×PBS. When tumor size reached 4-5 mm in diameter (n=4-5 per group), mice were randomly assigned into five (or more) groups. Typically, the groups include: an untreated group, a sham-treated group with diluent (as described in "Reagent") only, a VR-23-treated group, a paclitaxel-treated group, and a paclitaxel- and VR-23-treated group (simultaneously or paclitaxel first and followed by VR-23 treatment at 24 hour time-point).

Animals were monitored for food and water consumption every day, and their body weights and tumor volumes were measured twice per week. Tumor volumes were measured with a digital caliper and were determined by using the following formula: ½ length×width². Blood samples were collected via cardiac puncture and processed further for ALT and AST measurements. The animals were then immediately euthanized by carbon dioxide. Tumors and vital organs (spleen, kidney, liver and lung) were collected and fixed in 10% buffered formalin at 4° C. overnight before being processed for a paraffin embedding. The paraffin-embedded blocks were then cut to 4-5 μm thick sections. Each section of tumors and organs was stained with hematoxylin and eosin ("H&E"). Tumor sections were also subjected to immunohistochemistry staining with antibodies specific for proteins such as Ki-67 (proliferation marker) and VEGF (angiogenesis marker), and counter staining with hematoxylin.

Toxicity Study.

Changes in body weight and the amount and ratio of alanine transaminase (ALT)/aspartate transaminase (AST) were used to measure toxic effects. In addition, vital organs (liver, spleen, kidney and lung) were analyzed by (fluorescent) microscopy after they were harvested, fixed, processed, paraffin-embedded, sectioned, and stained as described herein.

Statistical Analysis.

All values are mean±S.E.M of at least three independent experiments. Analyses were performed using GraphPad Prism software (GraphPad Software, Inc, La Jolla, Calif., USA). Comparison between the groups was made by p value determination using one-way ANOVA. A p value of <0.05 was considered to be statistically significant.

Example 1

Results of antiproliferative activities of quinoline sulfonyl derivatives on breast cancer cell lines (MDA-MB231, MDA-MB468, and MCF7) and two non-cancer immortalized breast cell lines (184B5 and MCF10A) are shown in Tables III and IV.

Example 2

Antiproliferative activity of VR-23 was evaluated on a variety of different cell lines, alone or in combination with Bortezomib, by way of SRBSRB or clonogenic assays. As shown in (Table V, A), the inhibitory effects of VR-23 on breast cancer cell lines were from 2.6 (MDA-MB231 vs 184B5) to 17.6 times (MDA-MB468 vs MCF10A) greater than on the matching non-cancer breast epithelial cell lines. As shown in (Table V, B), the combination of VR-23 and Bortezomib is more effective than either one alone in MCF7 cells. The data in Table V, A and Table V, B are the average colony numbers from two independent experiments.

Example 3

Data from a clonogenic assay (Table VI, A) shows that the combination of VR-23 and paclitaxel is synergistic in MCF7 cells. The colony counts of MCF7 cells treated with 1 nM paclitaxel and 3.1 μM VR-23 were 35.8% and 46.8% of the non-treated control, respectively. However, the colony count was only 4.1% of the control when VR-23 and paclitaxel were used in combination. This result showed that a combinational treatment is synergistic, as an additive effect would result in 16.8% of the control (i.e., 35.8%× 46.8%=16.8%). As shown in Table VI, B, VR-23 killed U87MG brain cancer cells, alone or in combination with temozolomide.

Example 4

Figure 3:
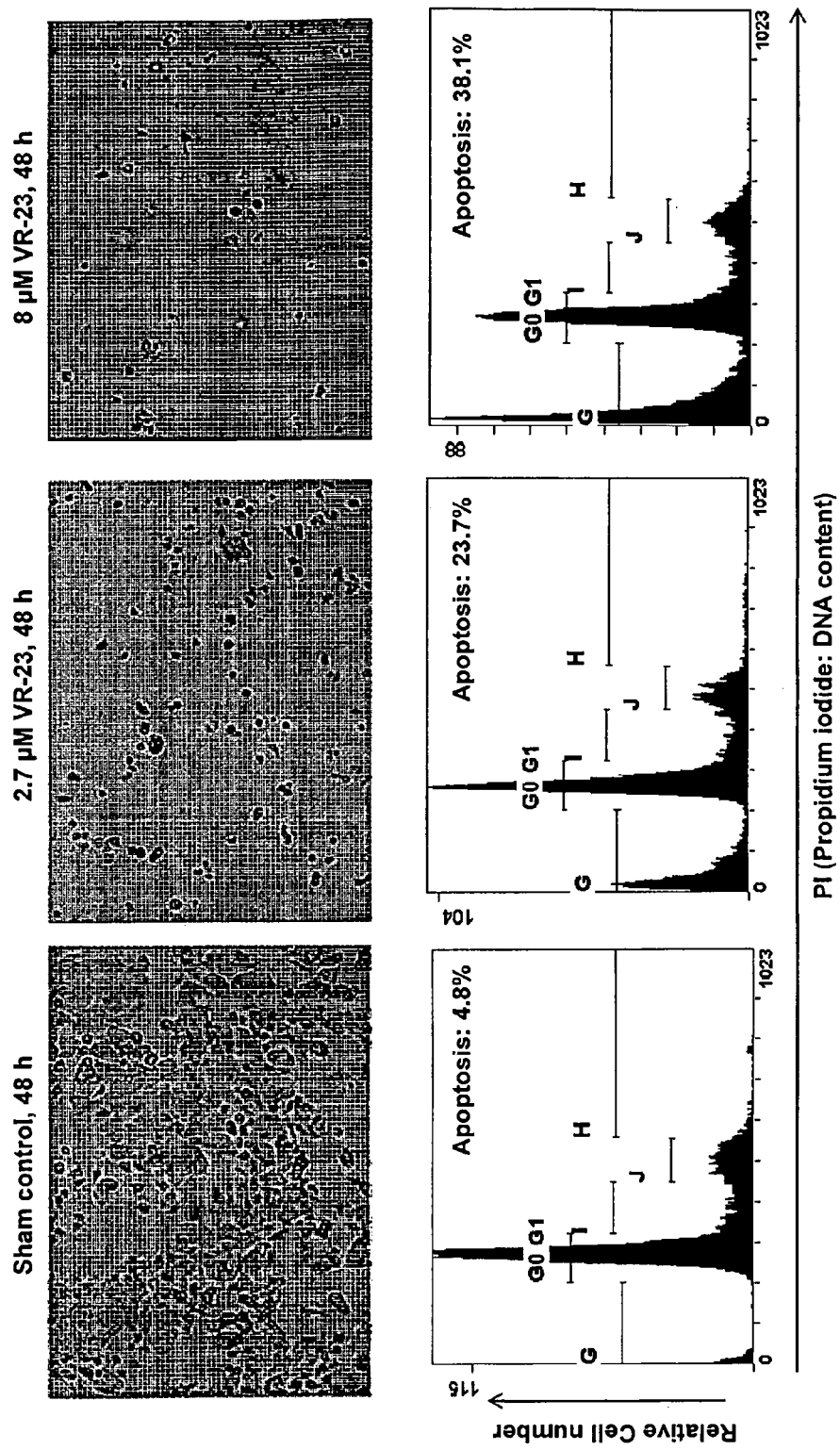
FIG. 3 shows the effect of VR-23 on apoptosis and cell cycle progression of MCF7 cells, as determined by microscopy and flow cytometry.

VR-23 caused apoptosis in cancer cells by 48 hour post treatment (FIG. 3). Asynchronous MCF7 cells were incubated for 48 hours in the absence (Sham treated control) or presence of VR-23 at 2.7 or 8.0 μM. The profile of flow cytometry shows that VR-23 caused apoptosis in MCF7 cells by 48 hour post drug treatment. (Note the sub-G1 DNA profile that is typical for apoptotic cell death.) The profiles of flow cytometry are consistent with the cell images in the corresponding upper panels (FIG. 3).

Example 5

Figure 4:
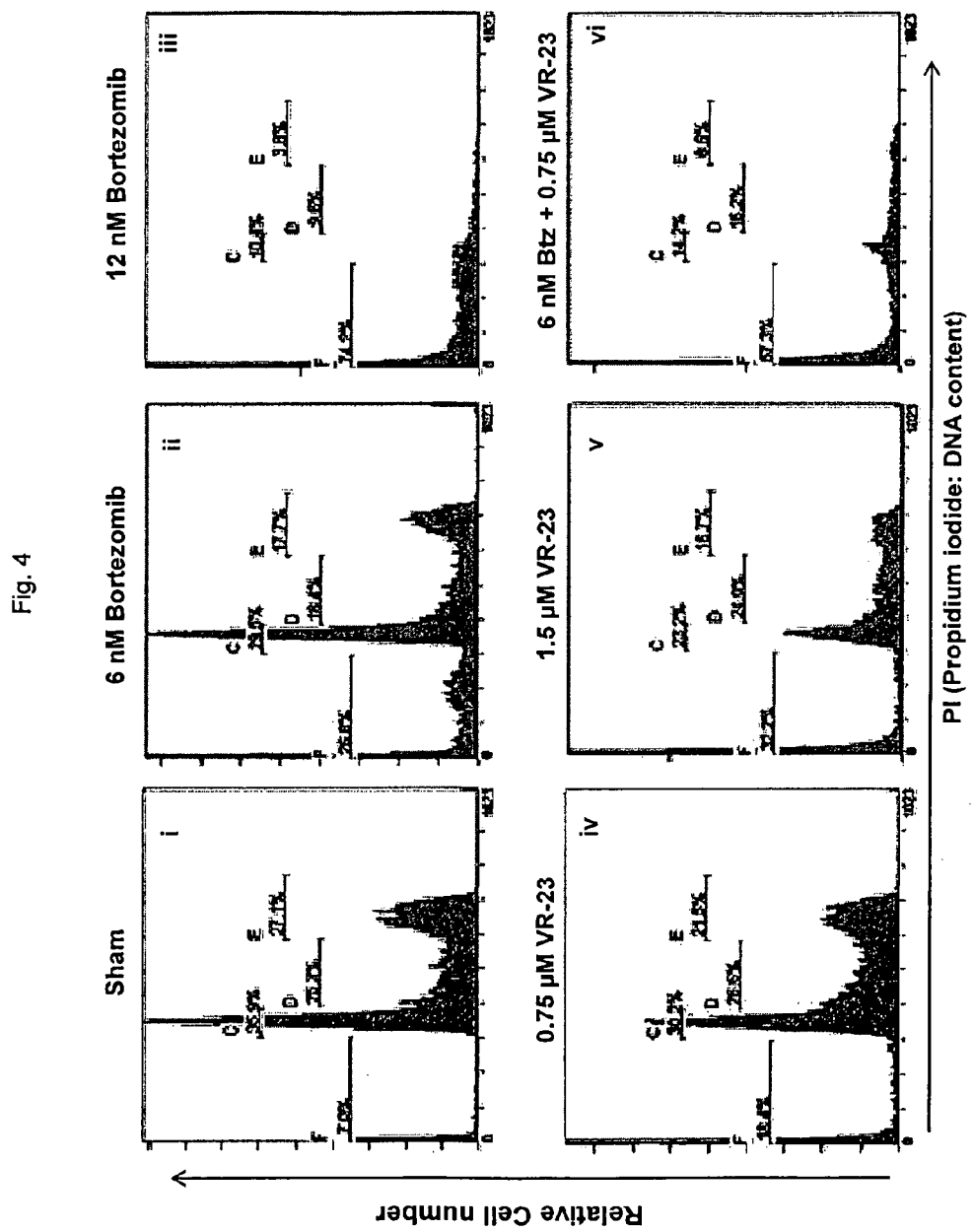
FIG. 4 shows the effect of VR-23, alone or in combination with Bortezomib™, on Jurkat lymphoma cells, as determined by flow cytometry. In this figure, "Btz" refers to Bortezomib.

The combination of VR-23 and Bortezomib showed synergistic effects in killing lymphoma cells (FIG. 4). Asynchronously growing Jurkat lymphoma cells were incubated for 48 hours in the absence (sham control) or presence of Bortezomib alone or in combination with VR-23. Combination of VR-23 and Bortezomib resulted in increased apoptotic cell death compared to cells treated with either drug alone at the same concentration. In this regard, neither 6 nM of Bortezomib (FIG. 4, ii) nor 0.75 μM of VR-23 (FIG. 4, iv) induced substantial cell killing by apoptosis (which is manifested by sub-G1 DNA content); however, the combination of the two almost completely wiped out the entire cell population by apoptosis (FIG. 4, vi).

Example 6

VR-23 was not notably toxic to the MCF10A non-cancer cells, up to 8 μM concentration (FIG. 5). A clonogenic assay of VR-23 was carried out using MCF10A cells (FIG. 5A). In the experiment, 50,000 cells were grown for 14 days in agarose-containing medium. Although only samples treated with 8.0 μM of VR-23 is shown, cells were also treated with 0.5, 1.0, 1.5, 2.0, and 4.0 μM (data not shown). It was found that colony counts were not substantially different among samples treated with 0.5-8.0 μM of VR-23. Flow cytometric profiles of MCF10A cells treated with 3.0 or 8.0 μM are shown in FIG. 5B. The flow cytometry profiles of the control and drug-treated samples with different doses of VR-23 are not substantially different. Thus, unlike MCF7 cells, the MCF10A non-cancer cells are more resistant to VR-23 (FIG. 5B, iii and iv), which is consistent with data generated with 184B5 non-cancer cells (see Table V). Furthermore, VR-23 showed milder effect than chloroquine (CQ) (compare FIG. 5B, iii and v). The $GI_{50}$ value of CQ on MCF7 is ~38 μM (Tables III and IV). Thus, 50 μM of CQ used in this experiment is approximately 1.3-fold of its $GI_{50}$, at which concentration some cells underwent apoptosis (FIG. 5B, v). This result is in contrast with those samples treated with 8 μM of VR-23 (3-fold $GI_{50}$ for MCF7), which did not induce any apoptosis in MCF10A (FIG. 5B, iii and iv). Thus, VR-23 is less toxic, but more active, than CQ.

Example 7

Figure 6:
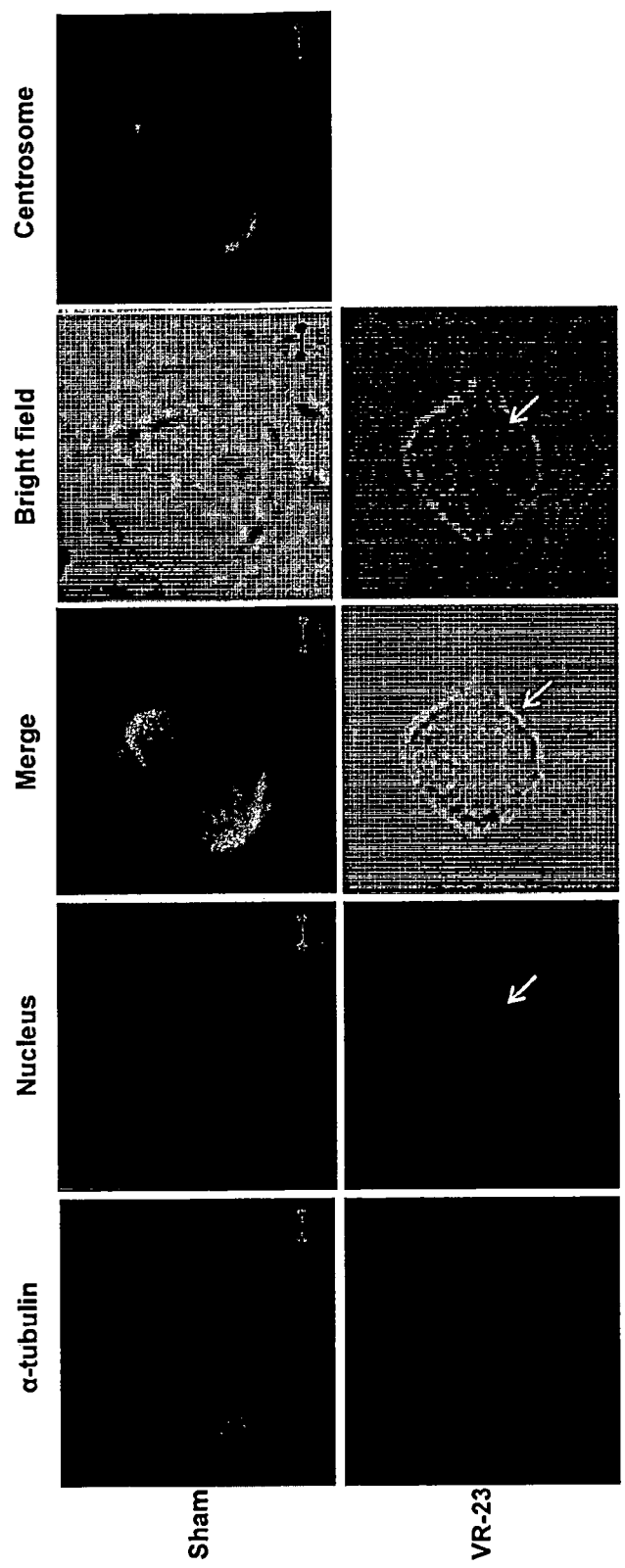
FIG. 6 shows representative images of the VR-23 effect on microtubule organization of MCF7 cells by microscopy. The arrows point to condensed chromosomes.

MCF7 cells treated with VR-23 contained multiple microtubule organization centers (FIG. 6). Asynchronous MCF7 cells were incubated in the absence (Sham control) or presence of VR-23 (10 μM). The cells treated with VR-23 showed: (i) multiple microtubule organization centers (~33%); and (ii) chromosomes were not aligned at the center of the cell, although they were condensed (arrows).

Example 8

Figure 7A:
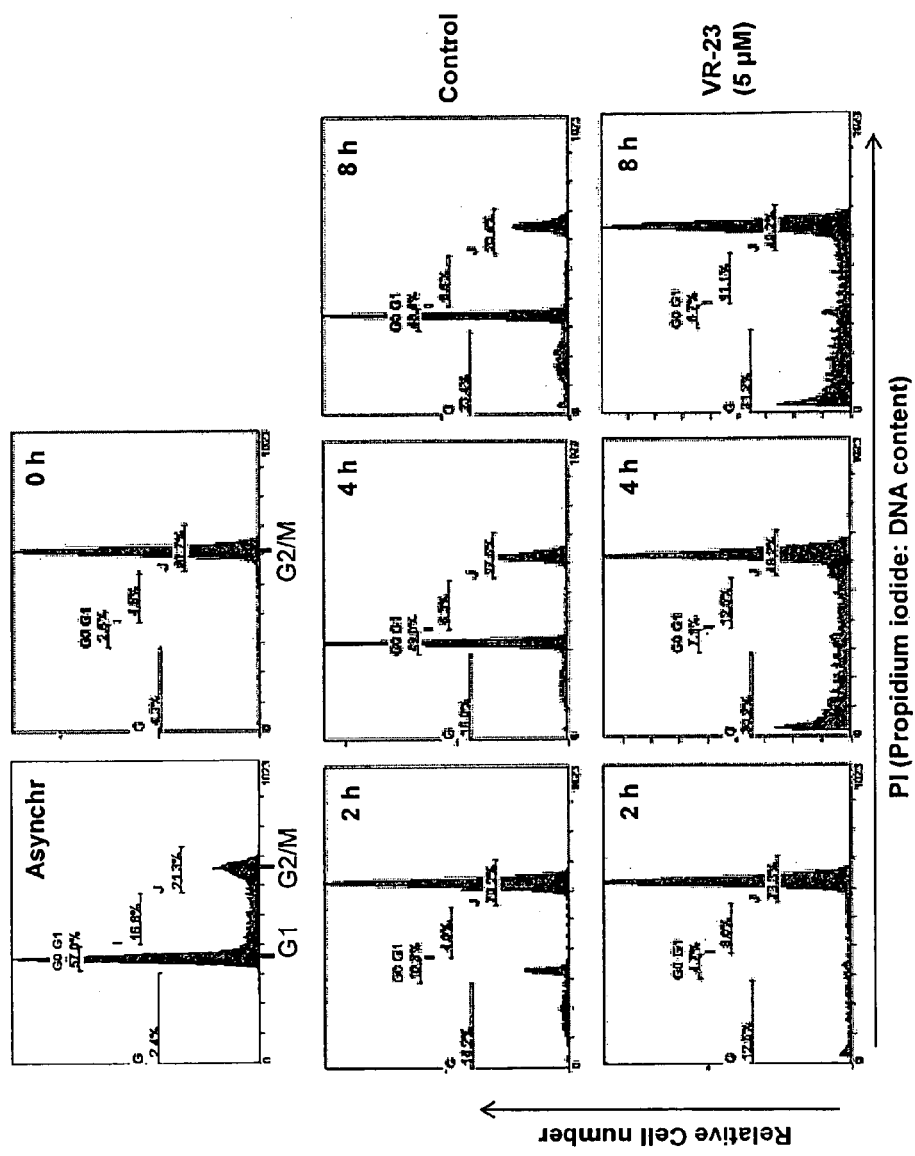
FIG. 7 shows VR-23 effect on cell-killing and cell cycle progression of HeLa S3 cells, as determined by flow cytometry (FIG. 7A) and Western blot analysis (FIG. 7B).
Figure 7B:
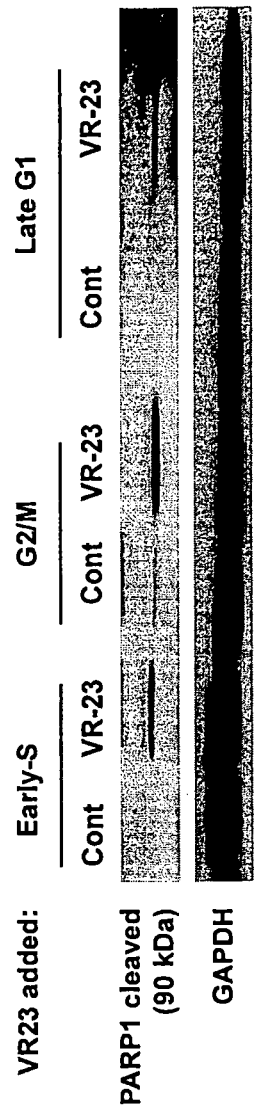

VR-23 at 5 μM caused massive cell death within 4 hours of treatment, when HeLa S3 cells arrested at G2-M transition by nocodazole were treated with the drug (VR-23, 4 h) (FIG. 7A). Under the experimental conditions, some of the cells were still stuck at G2/M until 8 hour post-drug treatment. "Asynchr" denotes asynchronous cells. 0 hour is the end of nocodazole treatment (i.e., 18 hours in 50 ng/ml nocodazole). At 0 hour, cells were released into complete medium in the absence (control) or presence of 5 μM VR-23 for 2, 4, or 8 hours as indicated. As shown in FIG. 7B, the mode of cell death by VR-23 is apoptosis. Extracts prepared from HeLa S3 cells treated with VR-23 in early-S phase (0 hour post double thymidine treatment), G2/M (arrested by nocodazole), or late G1 (6 hour post nocodazole) were subjected to Western blotting with anti-PARP1 antibody to detect proteins associated with apoptotic activities. Unlike the sham control (Cont), those cells treated with VR-23 showed PARP1 cleavage, indicating that cells underwent apoptosis.

Example 9

Figure 8A:
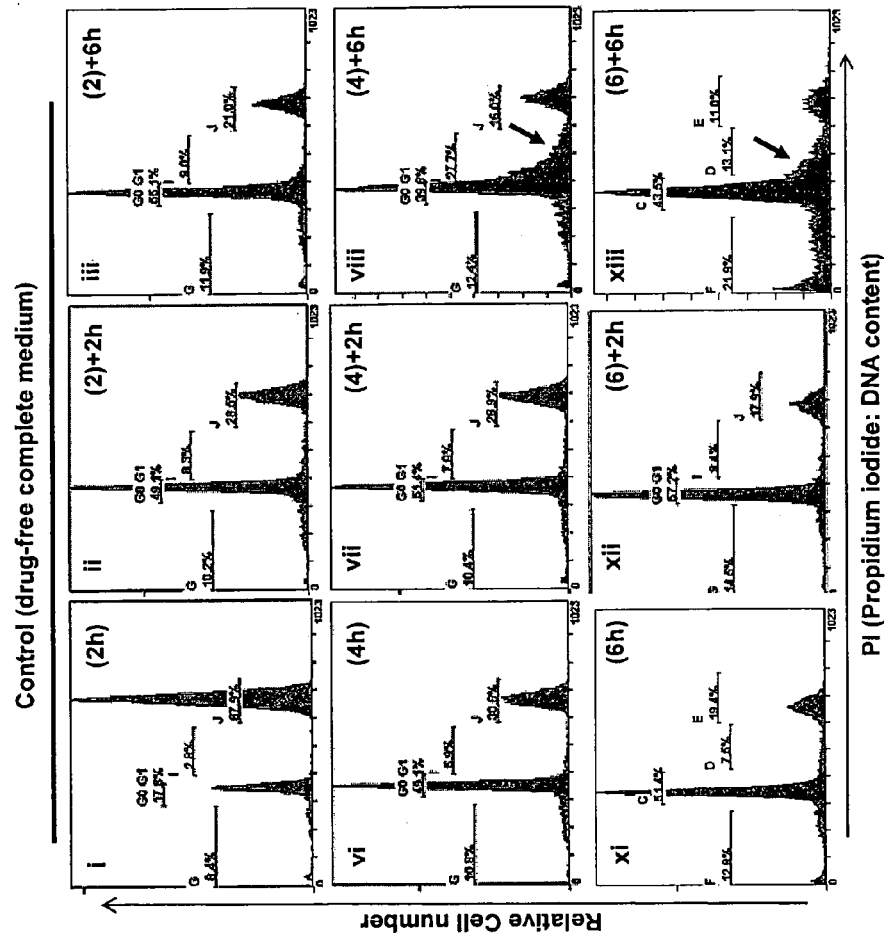
FIG. 8 shows the effect of VR-23 on HeLa S3 cells as determined by flow cytometry, where the HeLa S3 cells were arrested at the G2-M phase for 2, 4 or 6 hours (in brackets), followed by incubation for 2 or 6 hours (+h) in the absence (FIG. 8A) or presence of VR-23 (FIG. 8B).
FIG. 8C shows, by Western blot, the level of cyclins A and E in HeLa S3 cells arrested at the G2-M phase for 6 hours followed by incubation for 6 hours in the absence (Control) or presence of VR-23.

Evaluation of apoptosis in VR-23 treated and untreated control cells (FIG. 8). Treatment of cells in late G1 with VR-23 delayed their progression into S phase. HeLa S3 cells arrested in G2-M phase by nocodazole (50 ng/ml, 18 hours) were incubated in drug-free complete medium for 2, 4 or 6 hours (numbers in brackets), followed by incubation for 2 or 6 hours (+h) in the absence (control) (FIG. 8A) or presence (FIG. 8B) of 10 μM VR-23. Cells incubated in drug-free medium for 2-4 hours before treating with VR-23 still showed apoptosis (see FIG. 8B, iv, v, ix and x), although the rates of apoptosis were lower than those treated with VR-23 immediately after cells were released from nocodazole (FIG. 7). However, cells incubated in drug-free medium for 6 hours before treating with VR-23 did not induce apoptosis (see FIG. 8B, xiv and xv). By (6)+6 hours, most of the control cells already progressed into S phase, but VR-23-treated cells were still in G1 (long and short arrows, respectively). This data showed that VR-23 slowed down cell cycle progression from late G1 to S phase. The slowdown of cell cycle by VR-23 correlated with a high level of cyclin E and a lack of detectable cyclin A (FIG. 8C). The control sample showed a high level of cyclin A and a low level of cyclin E by the (6)+6 hour time-point examined. Under normal growth conditions, cyclin E expression peaks in late G1 and rapidly levels off as a cell enters S phase, at which time cyclin A expression rapidly increases. This Western blot data is consistent with the flow cytometric profile of the control cells shown in FIG. 8A. In contrast, cells treated with VR-23 still showed a high level of cyclin E and a lack of detectable cyclin A by (6)+6 hours, indicating that they were still in G1 phase. Thus cells treated with VR-23 were still in G1 phase because cyclin E was not degraded and cyclin A was not induced in a timely manner.

Example 10

Figure 9:
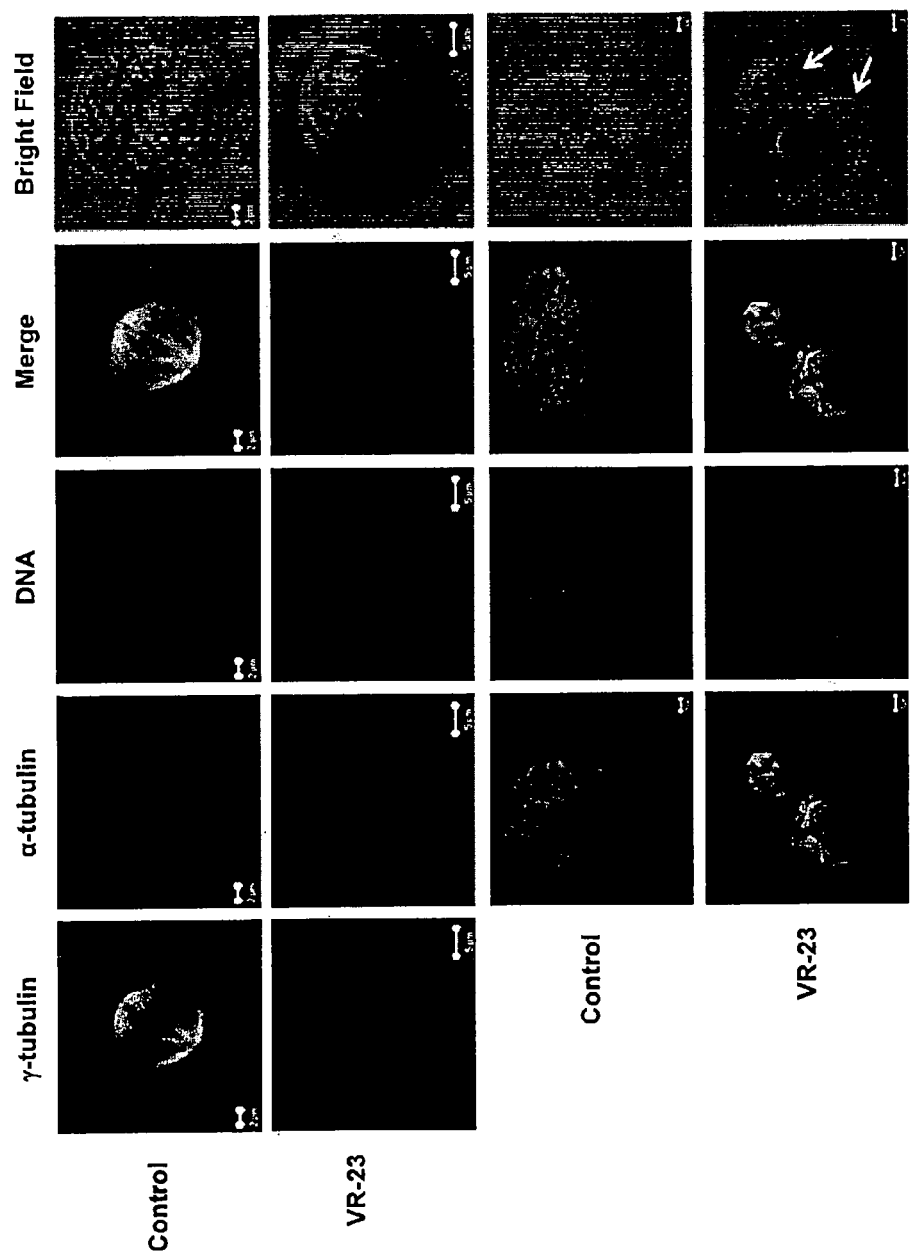
FIG. 9 shows representative images of the effect of VR-23 on the formation of spindle poles in HeLa S3 cells. The arrows point to the presence of uneven cell sizes.

VR-23 caused the formation of multiple spindle poles during late G1 phase in HeLa S3 cells (FIG. 9). HeLa S3 cells were synchronized at G2/M by nocodazole (50 ng/ml, 18 hours), followed by incubation for 6 hours in drug-free medium (at which time they were at G1) (see, e.g., FIG. 8). Cells were then incubated in the absence (control) or presence of 5 μM VR-23 for additional 6 hours (see flow cytometry profile in FIG. 8). Multiple spindle phenotype was seen in 44.4% of VR-23 treated cells analyzed. Note the presence of uneven cell sizes (arrows) which may have been generated as a result of nondisjunctional chromosome segregation during mitosis. In contrast, untreated control showed low mitotic index (i.e., the number of cells undergoing mitosis) and no notable multiple spindle phenotype.

Example 11

Figure 10:
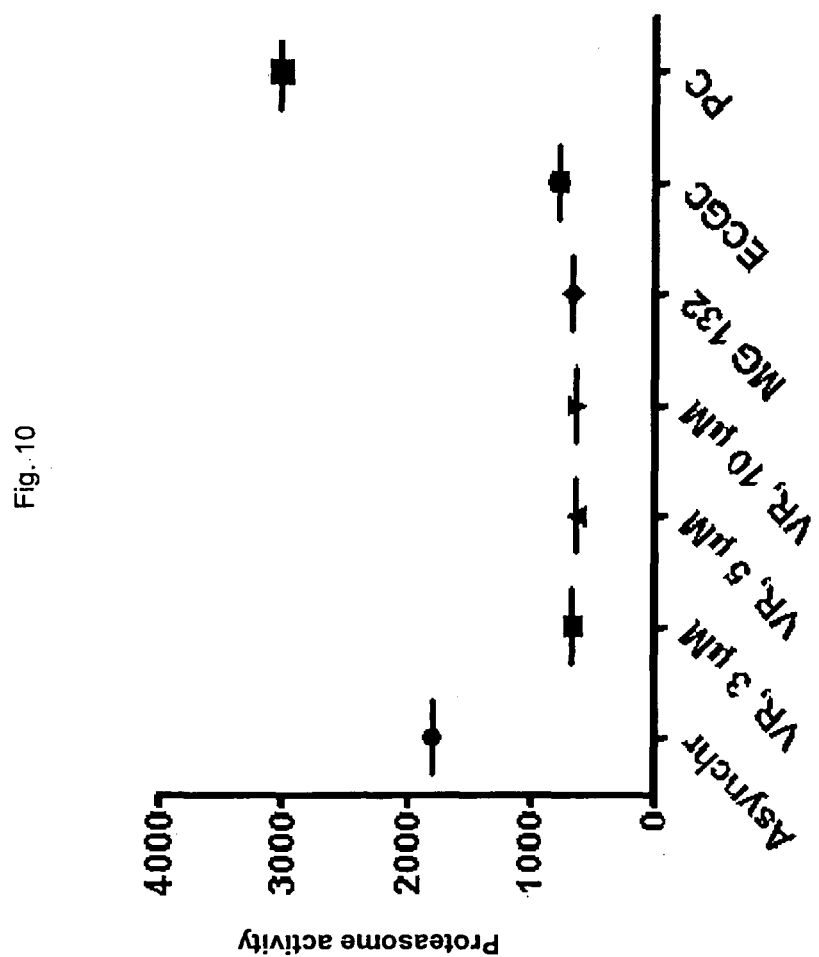
FIG. 10 shows the effect of VR-23, MG132 and ECGC on 20S proteasome activity in HeLa S3 cell lysates. In this figures, "Asynchr" refers to asynchronous HeLa S3 cells grown in the absence of VR-23; "VR" refers to "VR-23"; and "PC" refers to a positive control (jurkat cell extract).

Analysis of proteasome activity in HeLa S3 cell lysates treated with various compounds (FIG. 10). VR-23 inhibits proteasome activity. 20S proteasome activity was inhibited by 1 μM VR-23. MG132 and EGCG, known proteasome inhibitors, were used as positive controls. The PC positive control is cell lysates prepared from Jurkat cells with a high proteasome activity. "Asynchr" denote asynchronous HeLa S3 cells grown in the absence of VR-23. As shown in Table VII, VR-23 inhibited trypsin-like proteasome activity in HeLa S3 cell lysates—such proteasome activity was conducted in accordance with the assay described herein.

Example 12

Figure 11B:
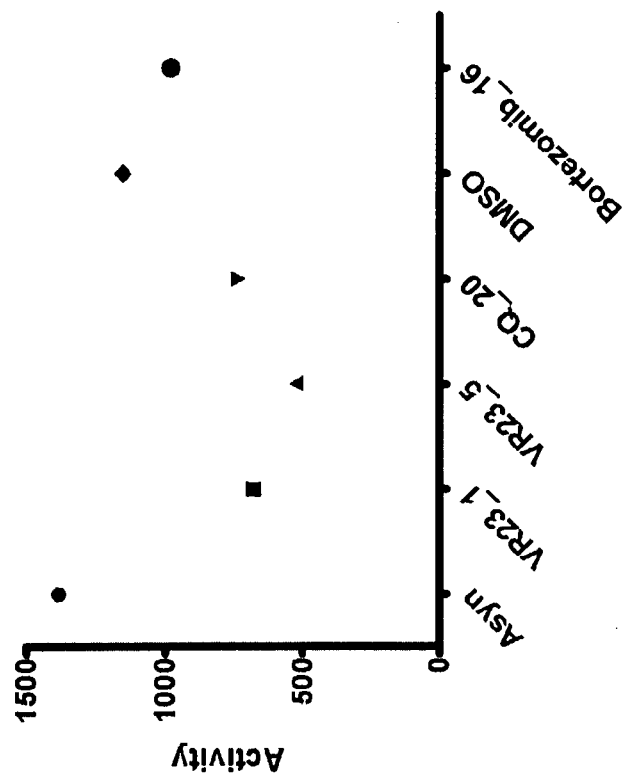
FIG. 11 shows the effect of VR-23, DMSO (negative control), chloroquine (CQ) or ECGC on proteasome activity in 184B5 non-cancer cells (FIG. 11A); and VR-23, DMSO (negative control), chloroquine (CQ) or Bortezomib on proteasome activity in MCF7 breast cancer cells (FIG. 11B). 'Asynchr' denotes asynchronous cells grown in the absence of VR-23.
Figure 11A:
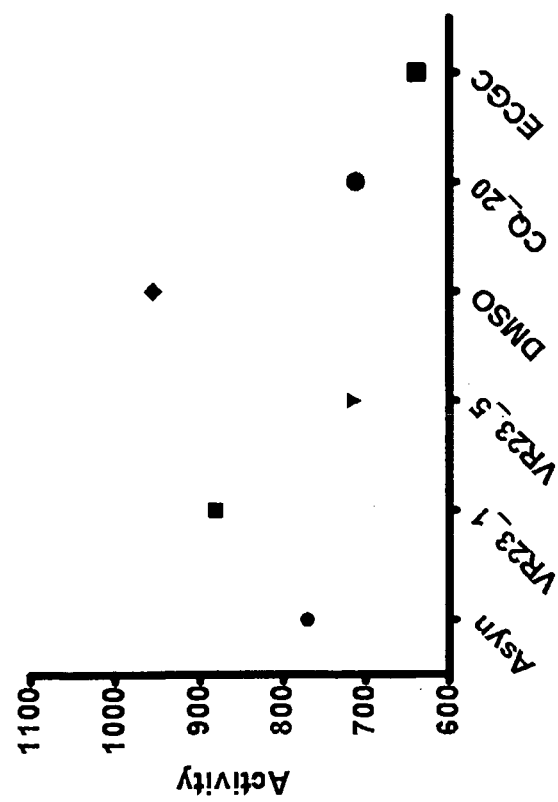

As shown in FIG. 11, the proteasome inhibition by 1 μM VR-23 was not pronounced in non-cancer 184B5 cells (FIG. 11A), compared to MCF7 cancer cells (FIG. 11B). This data is consistent with the observation that non-cancer cells are more resistant to VR-23 than cancer cells (Table V and FIG. 5), directly correlating the VR-23 mediated cell-killing with its property of proteasome inhibition.

Example 13

As shown in FIG. 12A, VR-23 caused abnormal cytoskeletal formation in HeLa S3 cells. Exponentially growing HeLa S3 cells were treated with 5 μM VR-23 for 6 hours, fixed, stained with an antibody specific for α-tubulin and then examined by confocal fluorescent microscopy for changes to their cytoskeletal structure. Sham denotes that the sample was treated exactly the same as VR-23 sample, except that they were not exposed to VR-23. As shown in FIG. 12B, VR-23 caused centrosome amplification in HeLa S3 cells. HeLa S3 cells were treated with 2 mM thymidine for 18 hours, followed by incubation for 11 hours in drug-free complete medium, by which time most cells were at mid-late G1 phase. The cells were then incubated for another 14 hours in 2.0 mM thymidine in the absence (control) or presence of 10 μM VR-23. Under these conditions, cells are trapped in the beginning of S phase by a second thymidine block. No centrosome was amplified in the control, while over 87% of VR-23 treated cells analyzed contained multiple centrosomes. This data along with the data shown in FIG. 9 (VR-23 causes centrosome amplification) and FIG. 10 (VR-23 is proteasome inhibitor) suggests that proteasome inhibition by VR-23 may cause centrosome amplification around the G1-S transitional period.

Example 14

Figure 13A:
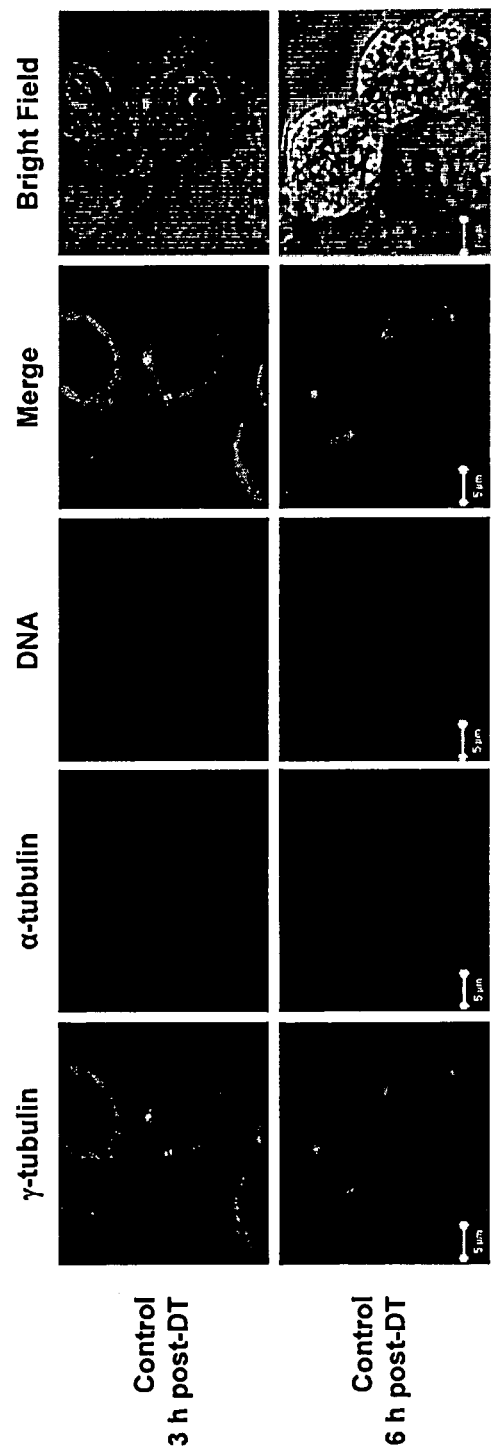
FIG. 13 shows representative images of an analysis of centrosome amplification in HeLa S3 cells synchronized at the G1/S border and then released into cell cycle for the indicated duration (hours) in the absence (FIG. 13A) or presence of VR-23 (FIG. 13B), as determined by microscopy.

As shown in FIG. 13, centrosome amplification manifested by 3 hour post-double thymidine (DT) treatment in HeLa S3 cells treated with VR-23. HeLa S3 cells synchronized at the G1/S border by DT treatment were released into cell cycle for 1-6 hours in the absence (control) (FIG. 13A) or presence (FIG. 13B) of VR-23, followed by confocal microscopy. Centrosome amplification was manifested by 3 hour post-DT, although supernumerary started to form by 2 hour post-DT (solid arrows). (Due to experimental variations, centrosome amplification is not visible by 2 hours in all instances). Following exposure of cells to VR-23 for 6 hours post-DT, some of the cells underwent activation of normal spindle checkpoint while others did not (dotted arrows). As shown in Table VIII, VR-23 caused multiple centrosome formation in the majority of cells in late G2-M phase. More than 70% of cells exposed to VR-23 for 12 hours during S-G2/M contained multiple centrosomes, compared to less than 4% in the control. At least 200 cells were counted for each sample, and each experiment was repeated at least three times.

Example 15

Figure 14:
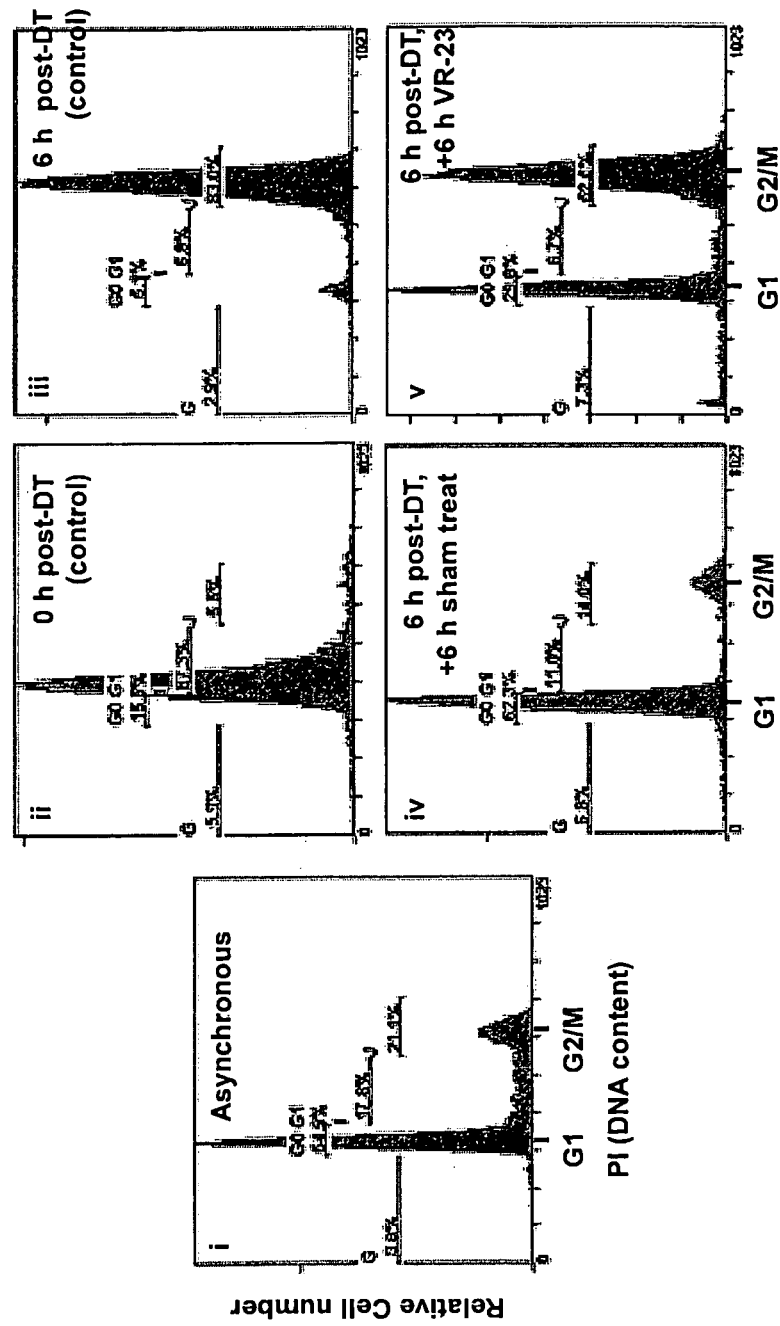
FIG. 14 shows cell cycle analysis of HeLa S3 cells treated with VR-23 at 0 to 6 hour post-double thymidine block, as determined by flow cytometry.

Cell cycle analysis of HeLa S3 cells treated with VR-23 (FIG. 14). VR-23 caused cell cycle delay even when cells were already in late-S to G2/M phase. Flow cytometry was carried out with asynchronously growing HeLa S3 cells (FIG. 14, i). HeLa S3 cells were synchronized at the beginning of S phase by double thymidine block (DT) (2.0 mM thymidine for 18 hours, 11 hours drug-free medium, 2.0 mM thymidine for 14 hours) (FIG. 14, ii). Cells synchronized by double thymidine block were released into drug-free complete medium for 6 hours, at which time most cells were at late-S to G2/M (FIG. 14, iii). Cells were continued to incubate in drug-free medium for additional 6 hours, at which time most cells were already in G1 (FIG. 14, iv). In FIG. 14, v, the cells were treated the same as the sample in FIG. 14, iv, except that the cells were incubated in the presence of 10 μM VR-23 for 6 hours. Note that only ~30% of cells were in G1, showing that VR-23 delayed the exit from G2/M under these experimental conditions (compare FIG. 14, iv and v).

Example 16

Figure 15:
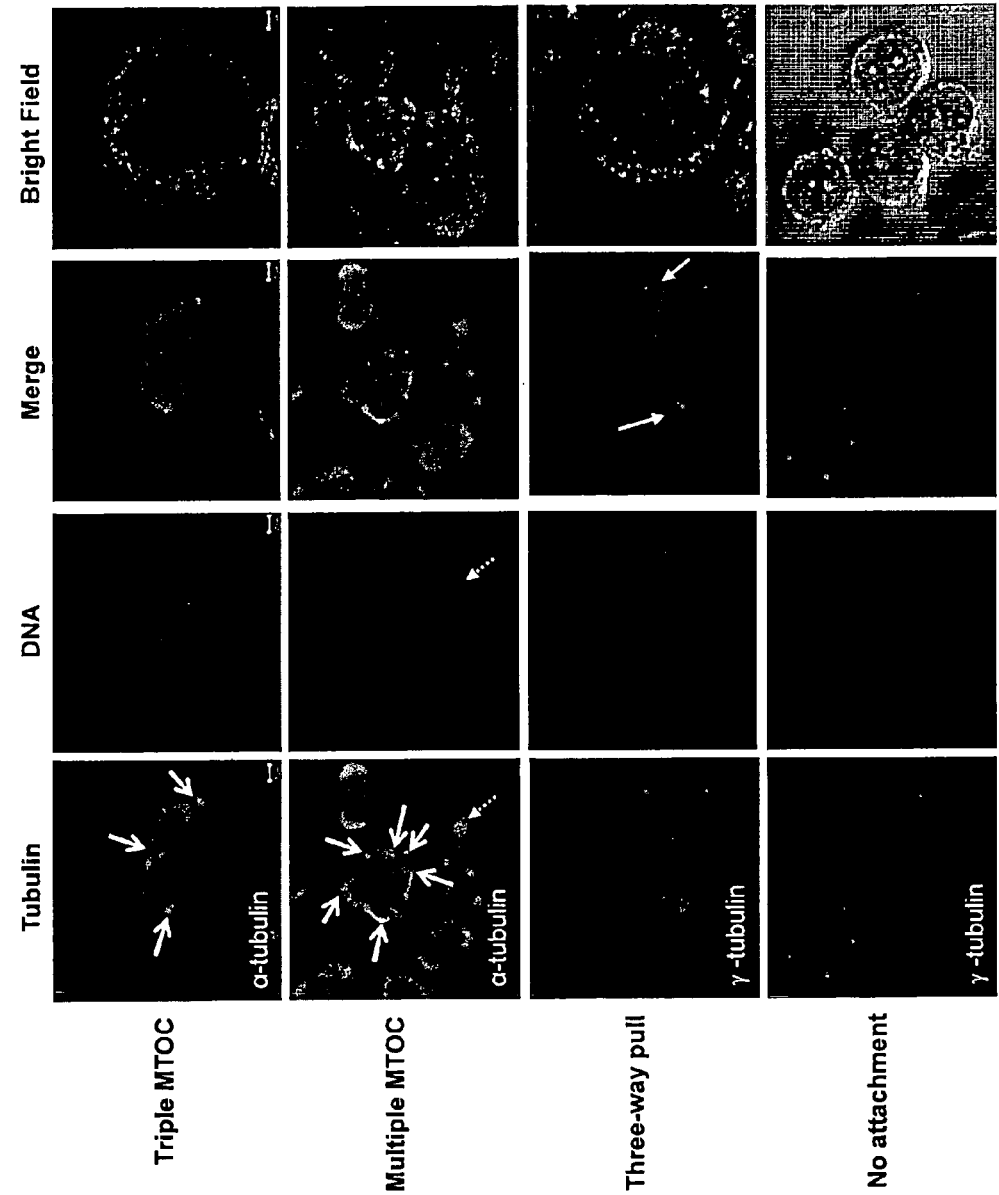
FIG. 15 shows representative images of the effect of VR-23 on cytoskeletal formation in HeLa S3 cells, as determined by microscopy.

As shown in FIG. 15, cells exposed to VR-23 showed a variety of different abnormal phenotypes. FIG. 15 is a representative microscopic analysis of cells shown in FIG. 14 (flow cytometry). HeLa S3 cells synchronized at G1/S by DT were released into normal medium for 6 hours (cells reached ~G2/M), at which time they were exposed to VR-23 for additional 6 hours. Solid arrows denote spindle assembly complexes. Dotted arrows show a part of a cell with microtubules that does not contain any DNA ('torn' phenotype). Triple MTOC/Three-way-pull phenotype comprises usually more than 50-60% of the total population. The "No attachment" phenotype is usually observed when DNA is not completely condensed. Among 352 cells counted, there were 120 mitotic cells (34.1%); and ninety four of these mitotic cells (78.3%) showed abnormal chromosome segregation.

Example 17

Figure 16B:
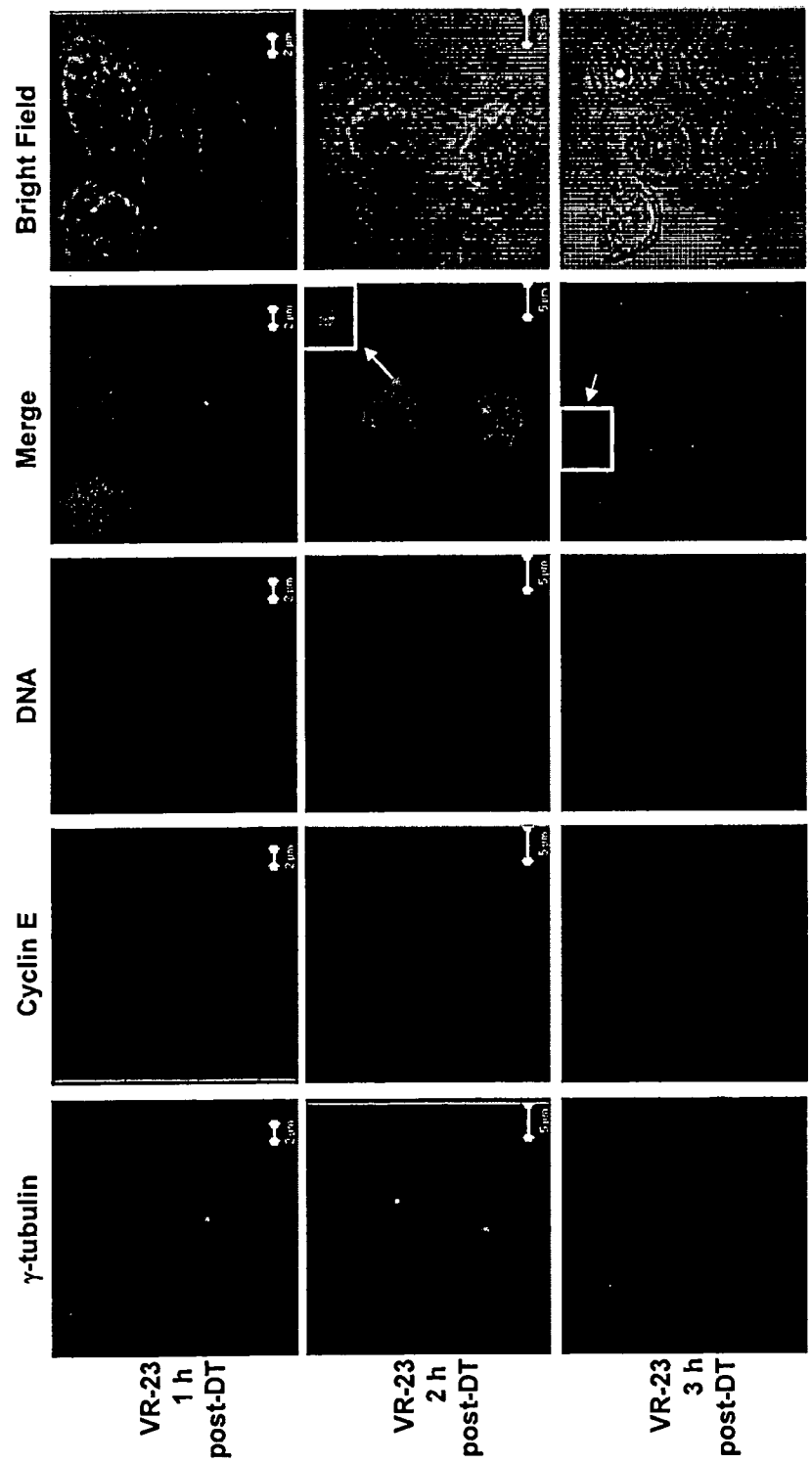
FIG. 16 shows representative images of an analysis of cyclin E localization in HeLa S3 cells in the absence (FIG. 16A) or presence of VR-23 (FIG. 16B) at various times post-double thymidine block, by microscopy.

As shown in FIG. 16, cyclin E was localized to the centrosome by 3 hour post-DT in cells exposed to VR-23. HeLa S3 cells arrested at G1/S by DT were released into cell cycle for 1-3 hours in the absence (control) (FIG. 16A) or presence (FIG. 16B) of VR-23. Cells were then fixed and immunostained with antibodies specific for γ-tubulin and cyclin E, or DNA stained. Under these experimental conditions, cyclin E was not notably localized to the centrosome in any time-point in the untreated control samples. In contrast, cyclin E was localized to the centrosomes by 3 hour post-DT in cells exposed to VR-23 (see inset boxes of FIG. 16B). Since cyclin E is a known positive regulator for centrosome duplication, the data herein presented suggests that VR-23 (a proteasome inhibitor as shown herein) stabilizes cyclin E in the centrosome, by which centrosomes are amplified. It is noted that proteasomes are localized to the centrosomes[12,13].

Example 18

Figure 17B:
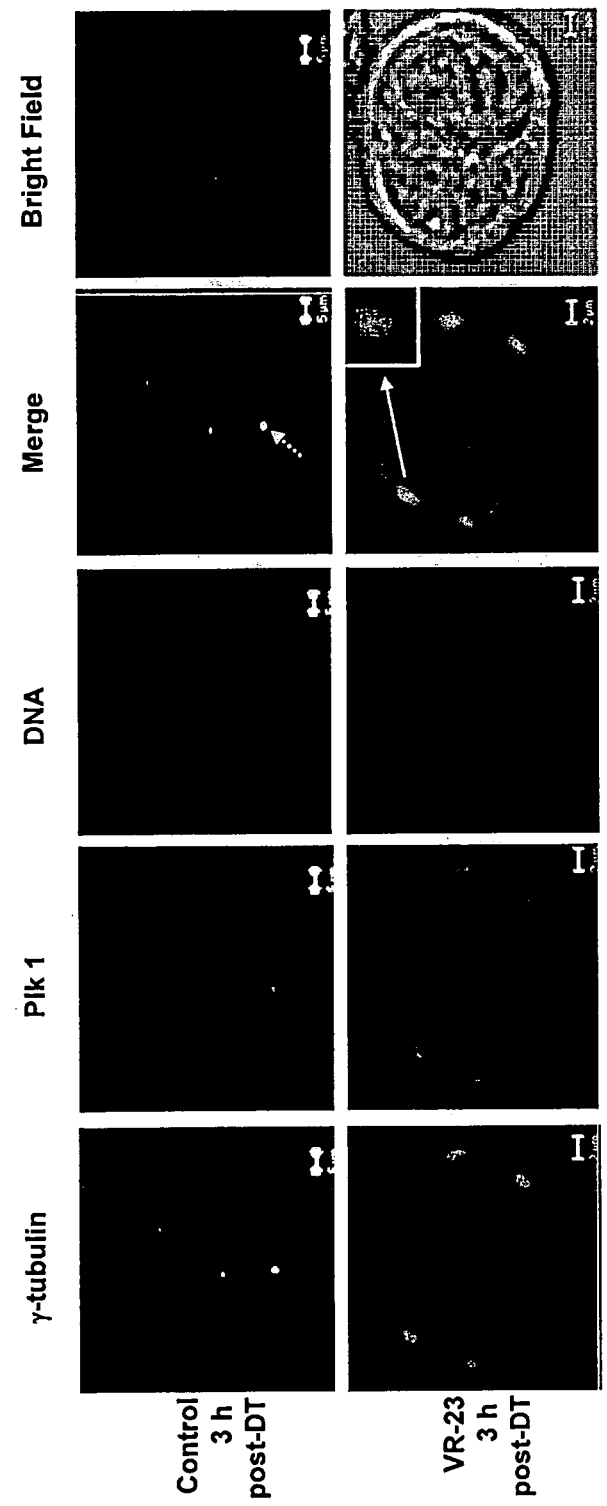
FIG. 17 shows representative images of plk1 localization in HeLa S3 cells in the absence or presence of VR-23 at 0 or 1 hour (FIG. 17A) or 3 hours (FIG. 17B) post-double thymidine block, by microscopy.

As shown in FIG. 17, Plk1 was localized to the centrosome by 3 hour post-DT in cells exposed to VR-23. HeLa S3 cells synchronized at the G1/S border by DT were released into cell cycle at time 0 hour. Cells were then allowed to progress through S phase for 1 hour (FIG. 17A) or 3 hours (FIG. 17B) in the absence (control) or presence of VR-23. Plk1 was not localized to the centrosome at 1 hour post-DT either in VR-23 treated or untreated control cells. However, unlike in the control, all of the (amplified) centrosomes in cells exposed to VR-23 contained Plk1 by 3 hour post-DT. It was occasionally observed that one of the two centrosomes in untreated cells also contained plk1 at 3 hour post-DT (dotted arrow).

Example 19

Figure 18A:
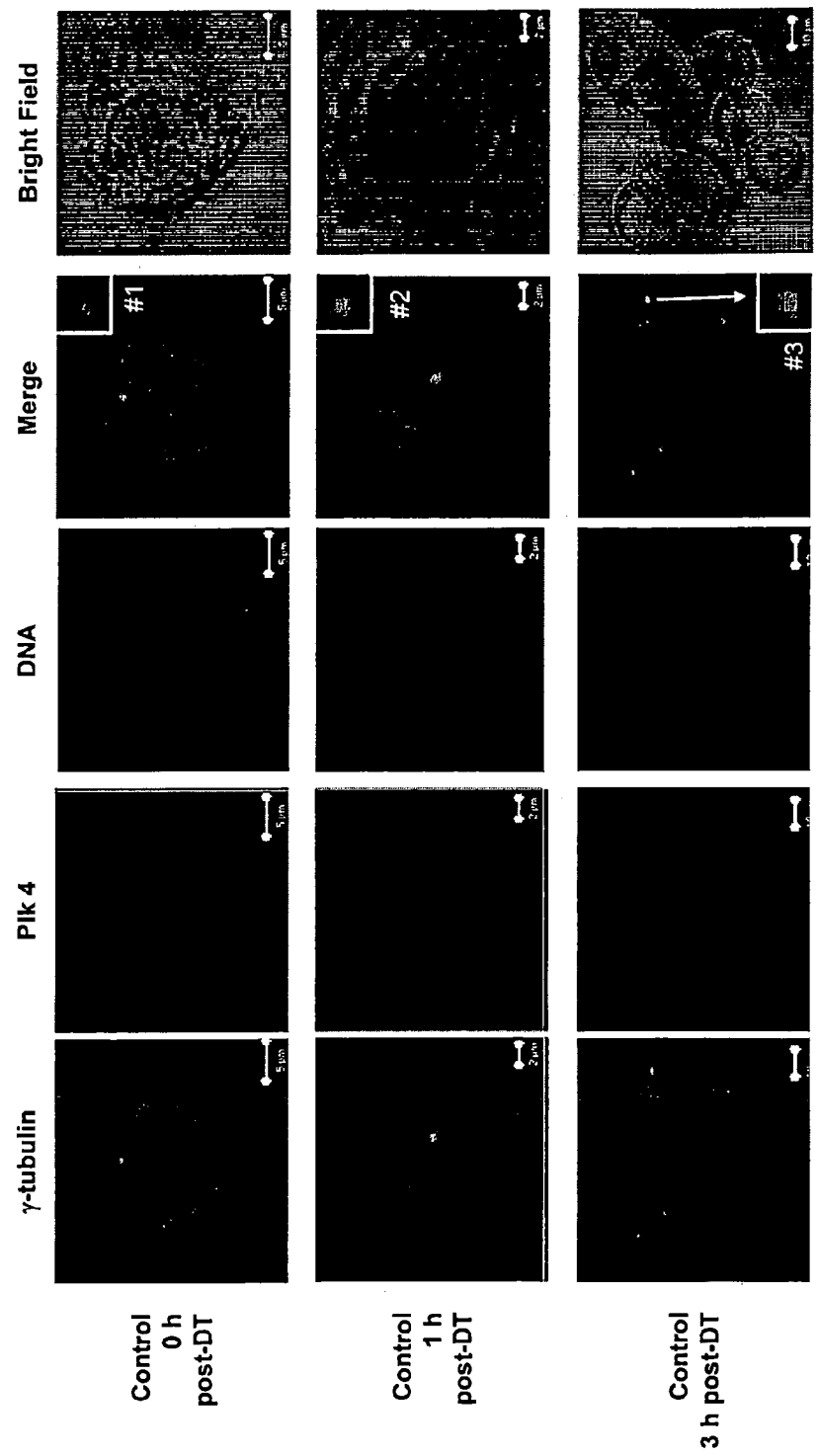
FIG. 18 shows representative images of plk4 localization in HeLa S3 cells in the absence (FIG. 18A) or presence of VR-23 (FIG. 18B) at various times post-double thymidine block, by microscopy.
Figure 18B:
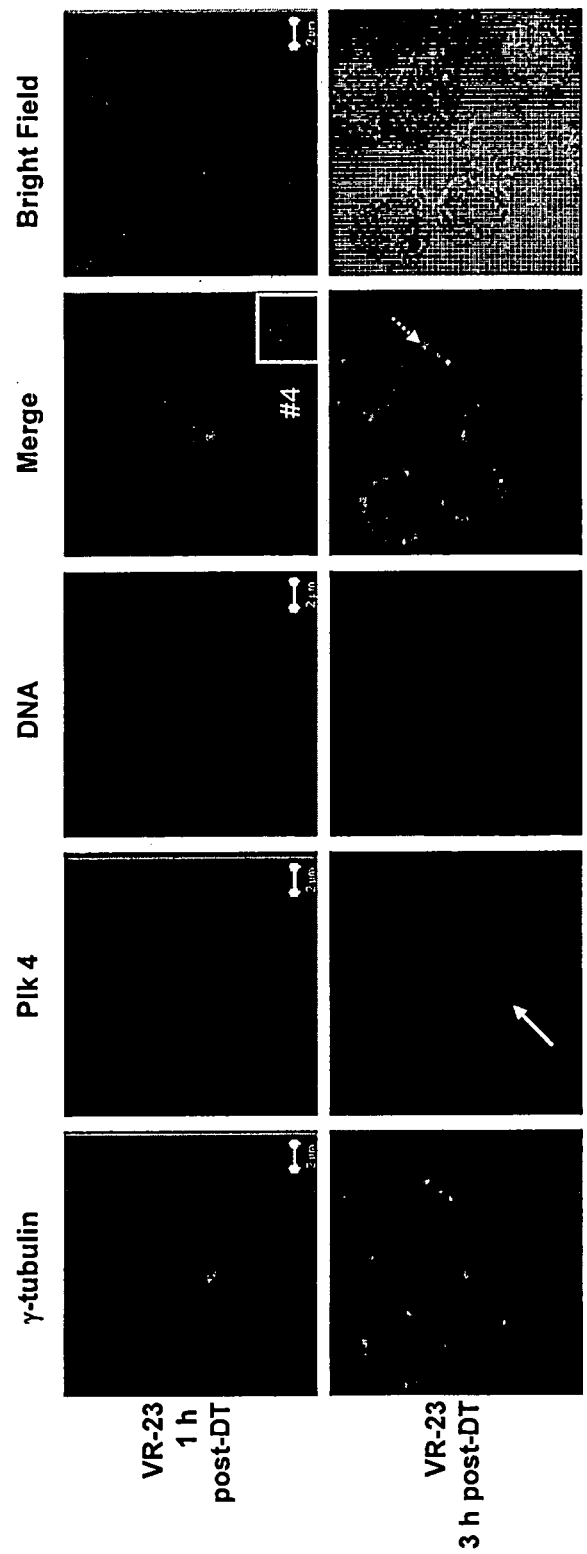

As shown in FIG. 18, the centrosomal localization of Plk4 was disrupted by VR-23 in HeLa cells. HeLa S3 cells synchronized at G1/S by DT were released into normal growth medium at 0 hour for 1-3 hours in absence (control) (FIG. 18A) or the presence (FIG. 18B) of VR-23. At the end of each time-point cells were fixed and immunostained with antibodies specific for γ-tubulin or Plk4. DNA was visualized by staining with DRAQ5. Inset boxes (#1-4) in FIG. 18A and FIG. 18B are the enlargement of centrosome dots. Contrary to cyclin E and Plk1, Plk4 was localized to the centrosome at least until 3 hour post-DT in the sham control (see inset boxes #1-3). This pattern was disrupted within 1 hour post-DT by VR-23 (inset box #4). Even by 3 hour post-DT, plk4 was not localized to "large" centrosomes (likely parental based on size), although it did localize to "small" centrosomes and the nucleoli in the presence of VR-23. By this time, plk4 presented a higher level in the nucleus of VR-23-treated cells than the sham control, as determined by fluorescent microscopy.

Example 20

Figure 19A:
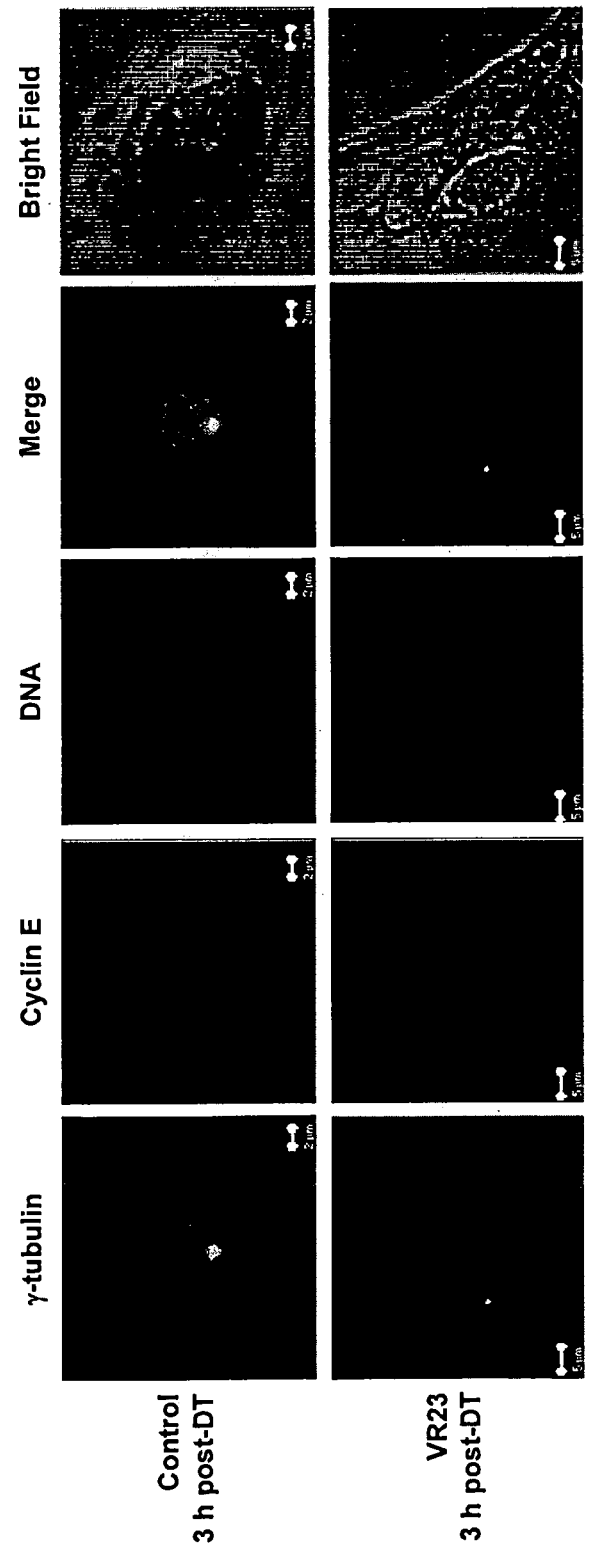
FIG. 19 shows representative images of cyclin E (FIG. 19A) or plk (FIG. 19B) localization in MCF10A non-cancer cells in the absence or presence of VR-23 at 3 hour post-double thymidine block, by microscopy.
Figure 19B:
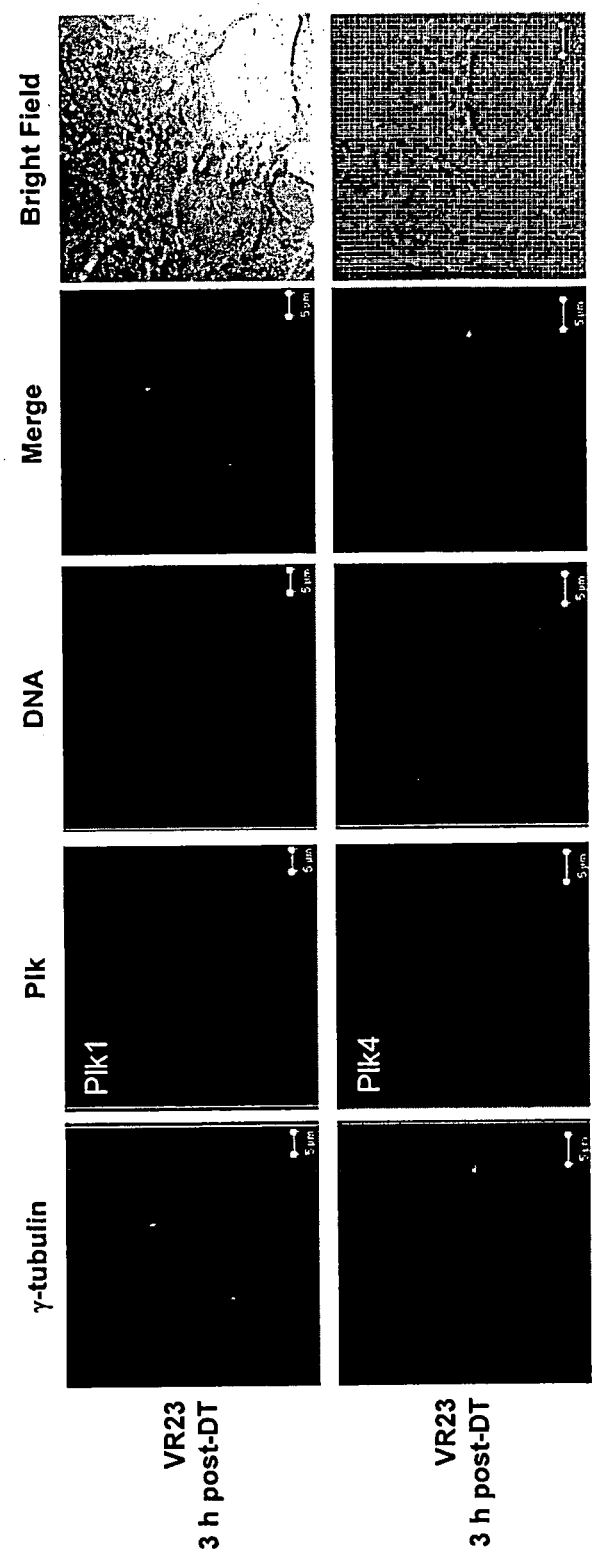

As shown in FIG. 19, VR-23 did not cause centrosome amplification in MCF10A non-cancer cells. MCF10A (non-cancer breast) cells synchronized at G1/S by DT were released into complete medium for 3 hours in the absence (control) or presence of VR-23 (20 μM), followed by immunostaining with an antibody specific for cyclin E (FIG. 19A) or Plk1 or Plk4 (FIG. 19B). Images were documented by confocal microscopy (Zeiss Axiovert). The levels of cyclin E and plk proteins were generally lower in non-cancer cells than in cancer cells. Unlike HeLa cells (FIG. 16), cyclin E was not localized to the centrosome in MCF10A cells exposed to VR-23 at the same 3 hour post-DT timepoint. Thus, the pattern of cyclin E and plk localization in MCF10A non-cancer breast cells in the presence of VR-23 was similar to that of HeLa S3 cells in the absence of VR-23.

Example 21

Figure 20:
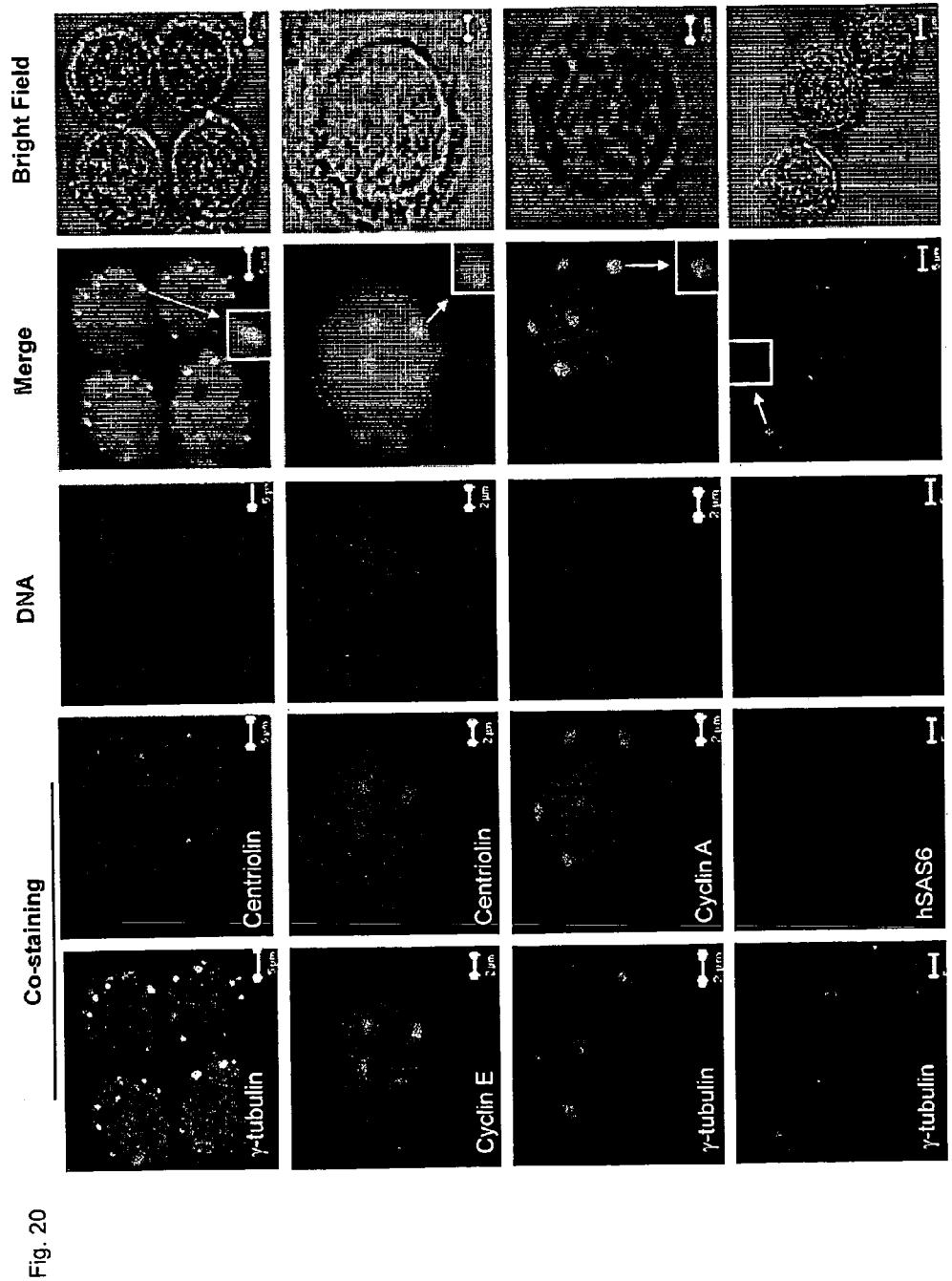
FIG. 20 shows representative images of cyclin A, cyclin E and hSAS6 association with γ-tubulin/centriolin in HeLa S3 cells exposed to VR-23 for 3 hour post-double thymidine block.

As shown in FIG. 20, cyclin E, cyclin A, and hSAS6 were associated with γ-tubulin/centriolin in HeLa cells by 3 hour post-DT in the presence of VR-23. HeLa S3 cells synchronized at G1/S by DT were released into cell cycle for 3 hours in the presence of VR-23. These cells were then fixed and immunostained with antibodies specific for γ-tubulin, centriolin, cyclin A, cyclin E, or hSAS6. DNA was stained with DRAQ5. Cyclin E, cyclin A and hSAS6 were associated with γ-tubulin/centriolin confirming their localization to the centrosome. Enlarged figures in inset boxes show the association status.

Example 22

Figure 21A:
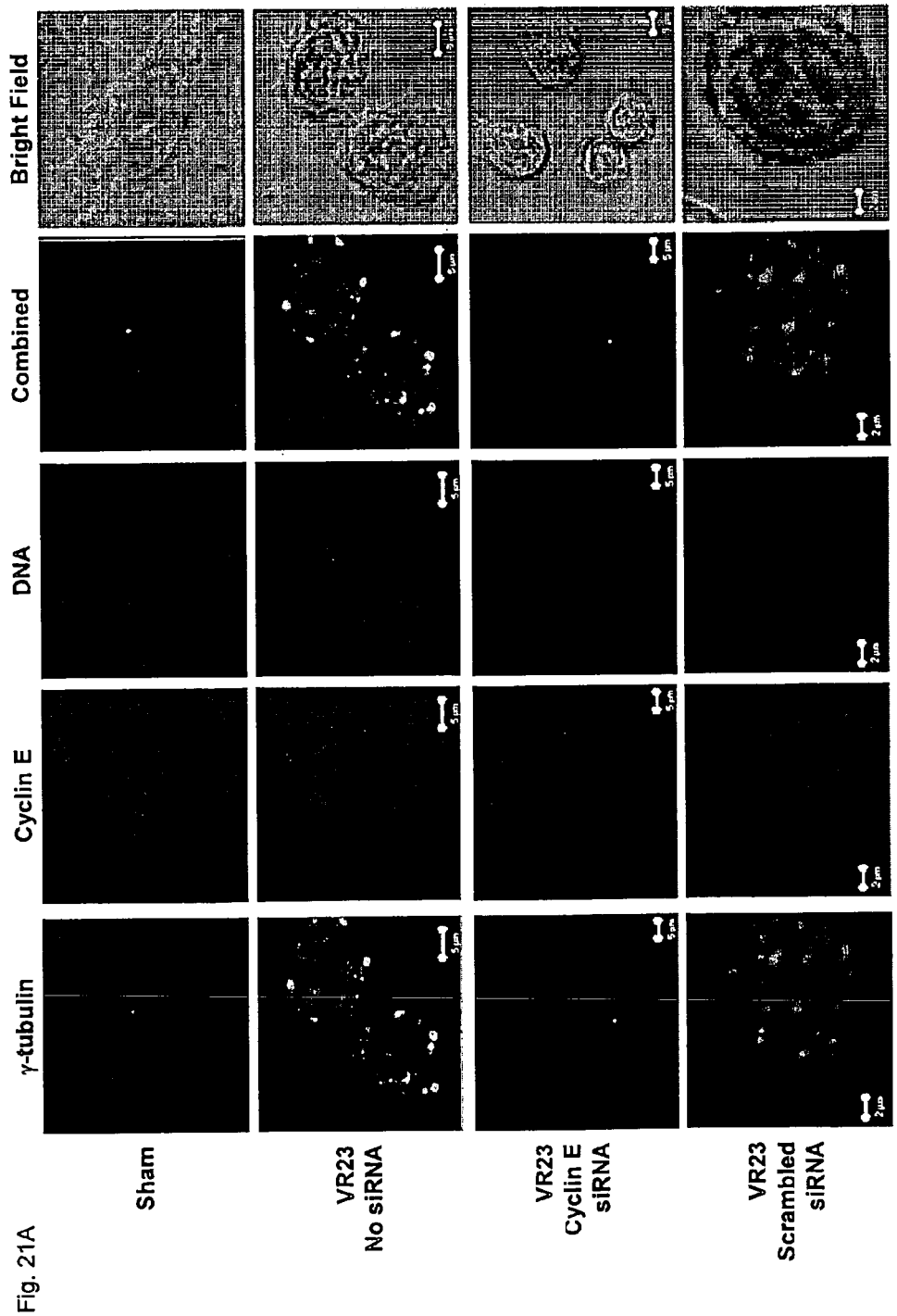
FIG. 21 shows the effect of cyclin E knockdown (confirmed by Western blot analysis as shown in FIG. 21B) on centrosome amplification in HeLa S3 cells in the absence or presence of VR-23, representative images shown in FIG. 21A, and effects summarized in FIG. 21C.
Figure 21B:
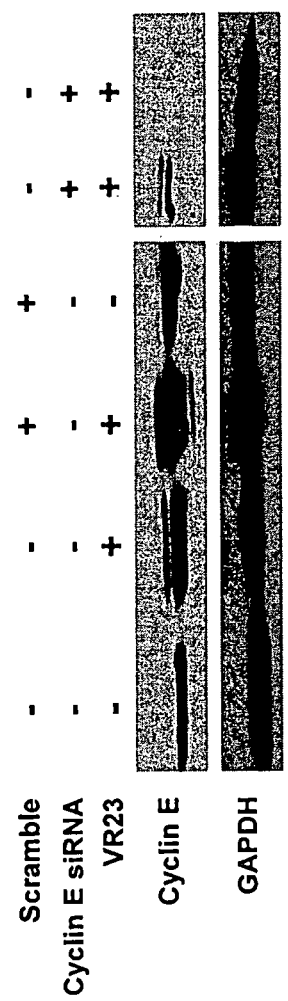

As shown in FIG. 21A, cyclin E knockdown suppressed centrosome amplification in HeLa S3 cells exposed to VR-23. HeLa S3 cells were transduced with scrambled RNA or cyclin E siRNA (100 nmol) for 12 hours, followed by synchronization at G1/S by DT. The cells were then released into normal complete medium for 3 hours in the absence (sham control) or presence of VR-23 (10 μM). The cells were then fixed and immunostained with antibodies specific for γ-tubulin or cyclin E. DNA was stained with DRAQ5. Data from Western blotting using extracts from HeLa S3 cells (as described above) with an anti-cyclin E antibody showed that cyclin E was successfully downregulated by cyclin E siRNA. (FIG. 21B). The effect of cyclin E ablation by siRNA on the population is summarized in FIG. 21C.

Example 23

Figure 22A:
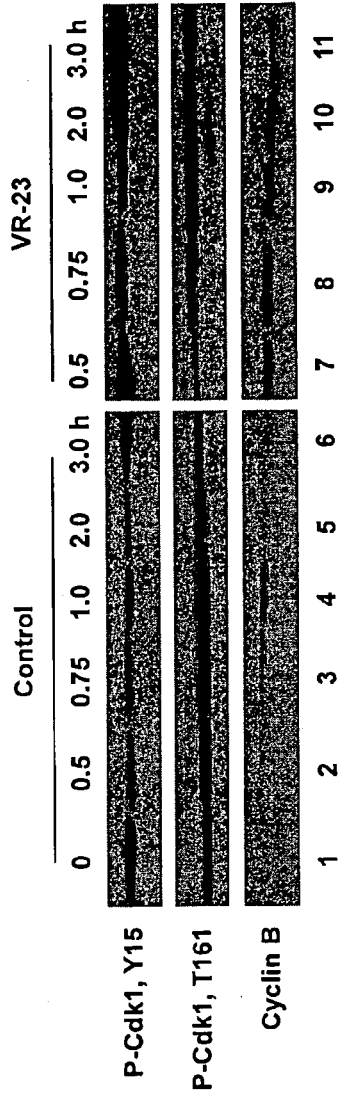
FIG. 22 shows the effect of VR-23 on the protein and phosphorylation levels of cyclin B and Cdk1 (FIG. 22A), and Wee1, Cdc25C, Securin, Cdc7 and Astrin (FIG. 22B) in HeLa S3 cells at various time-points post synchronization at G2/M with nocodazole. The "*" designates dephosphorylated Cdc7.
Figure 22B:
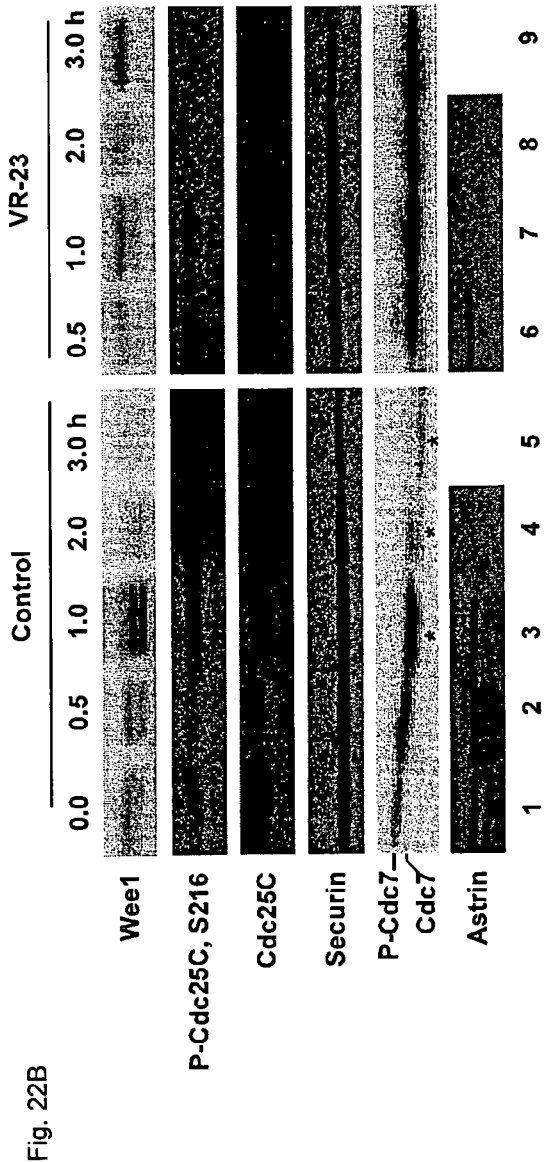

VR-23 treated cells are arrested at prometaphase through the inactivation of Cdk1 (FIG. 22). HeLa S3 cells were synchronized at G2/M phase by nocodazole (50 ng/ml, 18 hours), which is defined as 0 hour. The cells were then released into complete medium at time 0 hour without (control) or with 10 μM VR-23. Samples were taken at the indicated time-points post-nocodazole. (FIG. 22A) The phosphorylation of Cdk1 at Tyr15 was reduced at 1 hour time-point, but increased at 2-3 hours post-nocodazole arrest point, showing that Cdk1 was briefly activated followed by inactivation. The Cdk1 inactivation could be due to a feedback control mechanism as initial progress of cells to metaphase was abnormal (see FIGS. 7, 8, and 14). Since Thr161 was phosphorylated at these time-points, the exact cell cycle arrest point appears to be the space between Thr161 phosphorylation and Tyr15 dephosphorylation. Data shown in FIG. 22B indicates that Cdk1 inactivation correlates with the combination of a high level of Wee1 kinase and inactivation of Cdc25C. Wee1 was almost undetectable by 2 hour post-nocodazole in the control; however, it was detected until 3 hours in the VR-23 treated cells. Unlike in the control samples, Cdc7 was not dephosphorylated in VR-23 treated sample, which is consistent with the observation that cells do not progress into G1 in the presence of VR-23 (*, dephosphorylated Cdc7). Astrin was undetectable by 1 hour post-nocodazole. Since astrin prevents premature centrosome disengagement, this data showed that part of the centrosome amplification/dysregulation occurred at G2-M was due to premature centrosome disengagement.

Example 24

Figure 23:
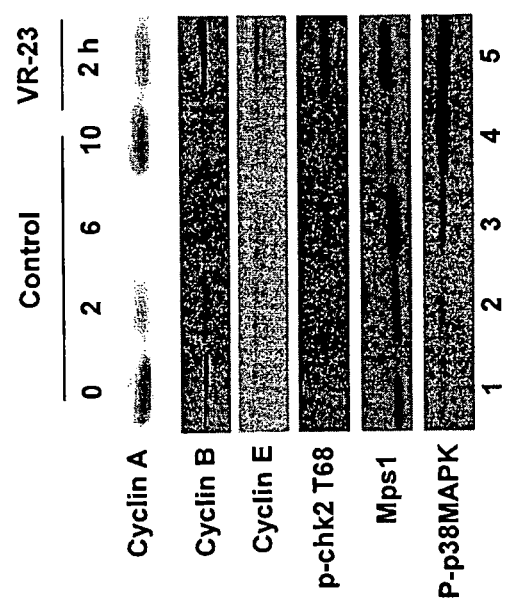
FIG. 23 shows the effect of VR-23 on the level of cyclins A, B and E, and on chk2, Mps1 and p38MAPK in HeLa S3 cells at various time-points post synchronization at G2/M with nocodazole.

Analysis of cyclins in HeLa S3 cells treated with VR-23 (FIG. 23). HeLa S3 cells were synchronized at G2/M with nocodazole (50 ng/ml, 18 hours), which is defined as time 0. The cells were then released into complete medium at time 0 hour without (control) or with 10 μM VR-23. Samples were taken at indicated time-points post-nocodazole. At 2 hour post-treatment, cyclins B and E were higher in the VR-23 treated cells than the control. This data is consistent with the notion that centrosome can still be amplified (due to the high level of cyclin E), even when cells do not exit from of M phase (manifested by the high level of cyclin B). The impediment of cyclins B and E degradation by VR-23 caused severe abnormality in the cell division process. The data is consistent with the notion that Chk2-mediated checkpoint is activated when DNA is fragmented by abnormal chromosome segregation caused by multiple centrosome formation by VR-23. Finally, cells activate apoptosis through phosphorylation of p38 MAPK in the presence of VR-23. (Note that the activation of p38 can occur in response to either cell stress or mitogenic stimulation[18]. The phosphorylation of p38 at 10 hour time-point in the control shown in FIG. 23 is not by cell stress by the cell cycle progression through G1/S to S as shown in FIG. 8A).

Example 25

Figure 24:
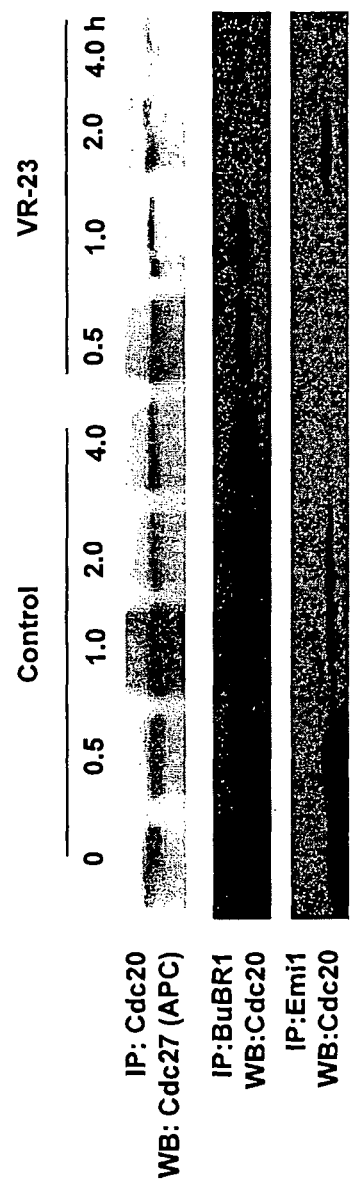
FIG. 24 shows immunoprecipitation data relating to the effect of VR-23 on the interaction of various proteins associated with cell cycle progression during mitosis in HeLa S3 cells.

Immunoprecipitation data shows that VR-23 caused cell cycle arrest prior to mitotic checkpoint in Hela S3 cells (FIG. 24). HeLa S3 cells were synchronized at G2/M by nocodazole treatment (50 ng/ml, 18 hours). At time 0 hour, cells were released into complete medium in the absence (control) or presence of VR-23 (10 μM). Samples were taken at indicated time-points post-nocodazole. The association of Cdc20 with Cdc27, which is required for the activation of the anaphase promoting complex (APC), peaked at 1 hour post-nocodazole in the control. In contrast, only low levels of the Cdc20-Cdc27 complex were detected in VR-23 treated samples. A spindle checkpoint protein BuBR1 is activated by kinetochores that are not fully attached with microtubules. Activated BuBR1 then inhibits the capability of APC to ubiquitinate securin and cyclin B and, thereby, prevents anaphase and mitotic exit until the cell is completely ready[14]. The high levels of BuBR1-Cdc20 association were observed in control samples at all of the time-points examined. In contrast, cells treated with VR-23 showed a low level of BuBR1-Cdc20 association until 1 hour time-point, after which the association was barely detectable. This data showed that some cells in VR-23 treated samples progressed through anaphase-mitosis up to 1 hour post-nocodazole; however, most of the cells did not activate the mitotic spindle checkpoint. Emi1 (early mitotic inhibitor 1; FBX5; FBXO5) regulates progression through early mitosis by inhibiting APC. By binding to APC or APC activators (CDC20 and FZR1/CDH1), Emi1 prevents APC activation[14]. In the control samples, Emi1 associated with APC for first 30 min after release from nocodazole, followed by only low levels of association up to 2 hours. This data showed that cells released into drug-free medium have largely passed prometaphase-metaphase transition by 1 hour post-nocodazole. In contrast, the Emi1-Cdc20 complex was not detected in cells treated with VR-23, except 2 hour post-nocodazole. Since associations of Cdc20 with BuBR1 and Emi1 usually occur in prometaphase and prophase, respectively[14], cells treated with VR-23 were largely arrested at prometaphase, eventually leading to the activation of apoptosis. The activation/phosphorylation of p38 MAPK may play a role in the activation of apoptosis at this transition.

Example 26

Table IX describes a typical administration protocol for vehicle, VR-23, paclitaxel (Tax), or combination of VR-23 and paclitaxel. "Tax+VR-23" denotes that paclitaxel and VR-23 were administrated simultaneously, and "Tax, VR-23" denotes that paclitaxel was given 24 hours prior to VR-23.

Example 27

Figure 25B:
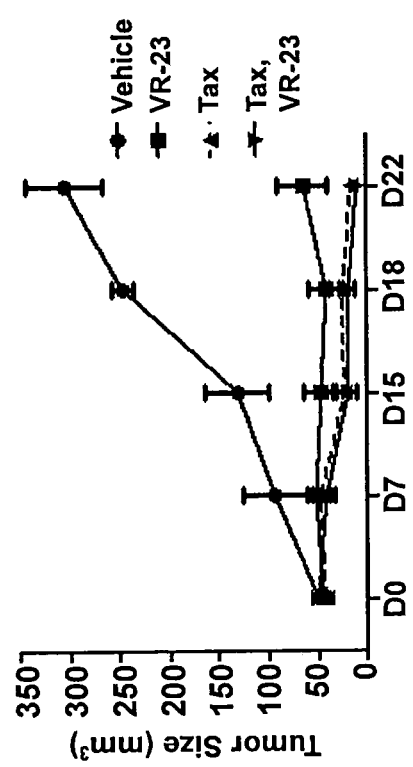

As shown in FIG. 25, VR-23 showed antitumor activity in a xenograft model. FIG. 25A shows representative ATH490 athymic mice engrafted with MDA-MB231 human metastatic breast cancer cells that were treated with VR-23 alone or in combination with paclitaxel as described in Table IX and in the Materials and Methods herein with respect to Animal Studies. The combination of VR-23 and paclitaxel (Tax, VR-23) was more effective in tumor treatment compared to treatment with VR-23 or paclitaxel alone. The changes in tumor sizes in response to drug treatment are shown in a FIG. 25B and in Table X. With respect to FIG. 25B, values in bar of the graph are mean±S.E.M. "D" denotes day(s) post-treatment.

Example 28

Figure 26B:
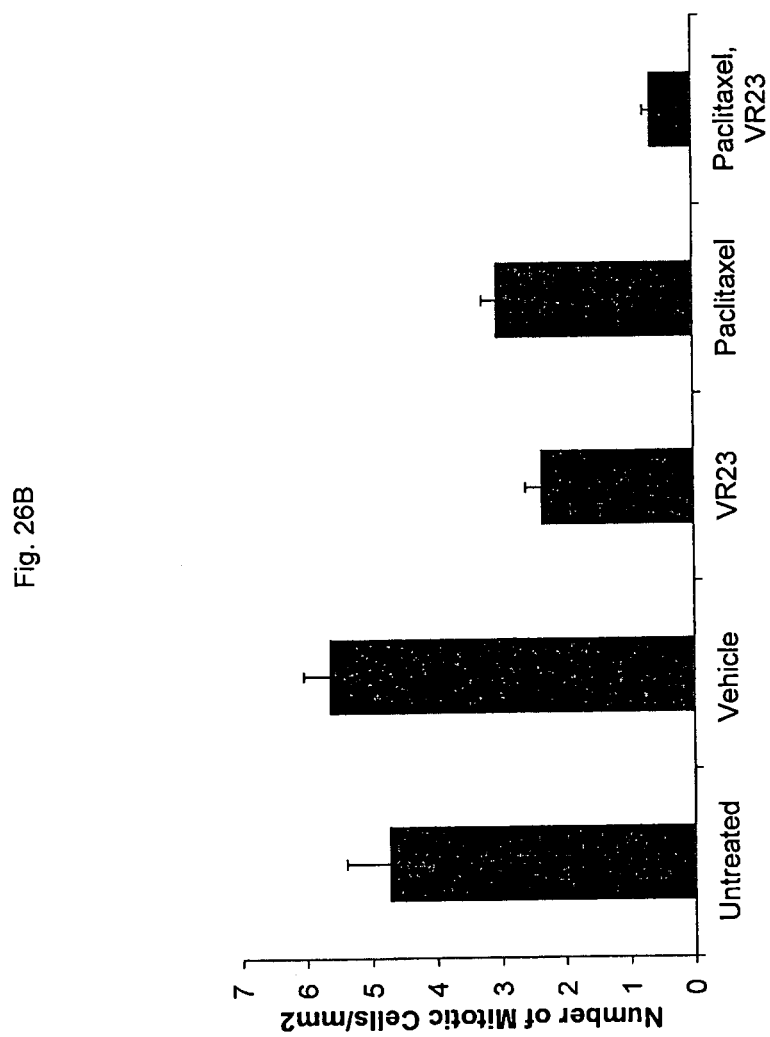
FIG. 26 shows the effect of VR-23 on the number of mitotic cells in tumor samples taken from ATH490 mice engrafted with MDA-MB231 cells and treated with VR-23, paclitaxel, or a combination of VR-23 and paclitaxel, as determined by microscopy (FIG. 26A), which data was then summarized in graphical form (FIG. 26B).

As shown in FIG. 26, VR-23 inhibited tumor cell proliferation in a xenograft model. With respect to FIG. 26A, ATH490 mice were engrafted with MDA-MB231 as described herein. Tumor samples taken at 15 days post-treatment were immunostained with an antibody specific for Ki-67, and then counter stained with hematoxylin. Bright field images were taken with a Zeiss EPI-fluorescent microscope using a 10× objective. With respect to FIG. 26B, mitotic index of tumor samples was determined at 29 days post-treatment by counting mitotic cells from at least ten different fields using a 20× objective.

Example 29

Figure 27A:
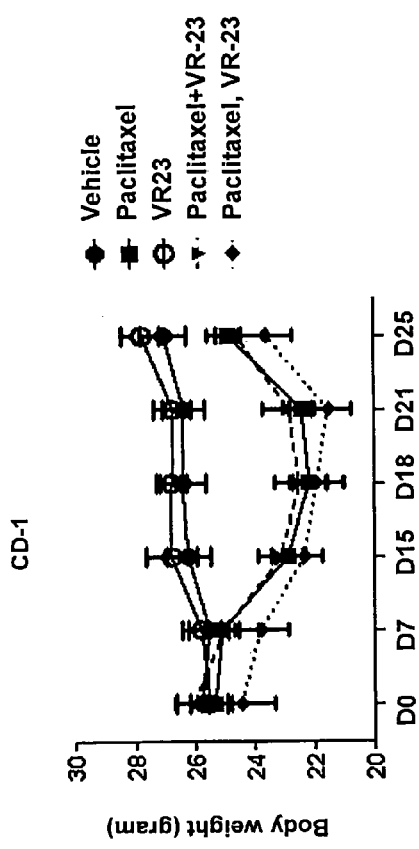
FIG. 27 shows the effect of VR-23 and/or paclitaxel on body weight in CD-1 mice (FIG. 27A) and in ATH490 mice (FIG. 27B).
Figure 27B:
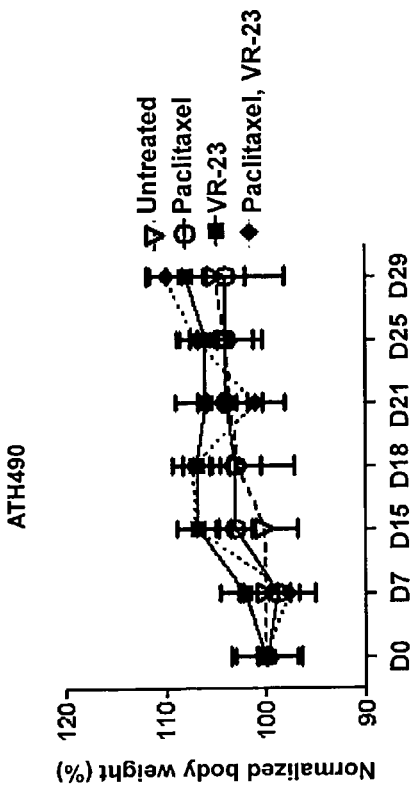

The effect of VR-23 on the body weight of mice is shown in FIG. 27. With respect to FIG. 27A, treatment (i.p.) of CD-1 athymic mice with 25 mg/kg/week of VR-23 alone or in combination with paclitaxel did not show any ill effects to the animals, as determined by changes in body weights. Six weeks old CD-1 mice were subjected to drug treatment as indicated: Vehicle refers to sham-treated control; "Tax+VR-23" denotes that paclitaxel (10 mg/kg, i.v.) and VR-23 (12.5 mg/kg; i.p.) were administrated simultaneously; and "Tax, VR-23" denotes that paclitaxel (20 mg/kg) was given 24 hours prior to VR-23 (25 mg/kg). D0-D25/D29 denotes day 0 to days 25/29 post-drug treatment. With respect to FIG. 27B, VR-23 (30 mg/kg) did not show any notable toxic effect in ATH490 athymic mice, compared to the untreated control. Paclitaxel (i.v.) was given 20 mg/kg body weight. The body weights of ATH490 mice are normalized on the basis that those of day 0 are 100%.

Example 30

Figure 28:
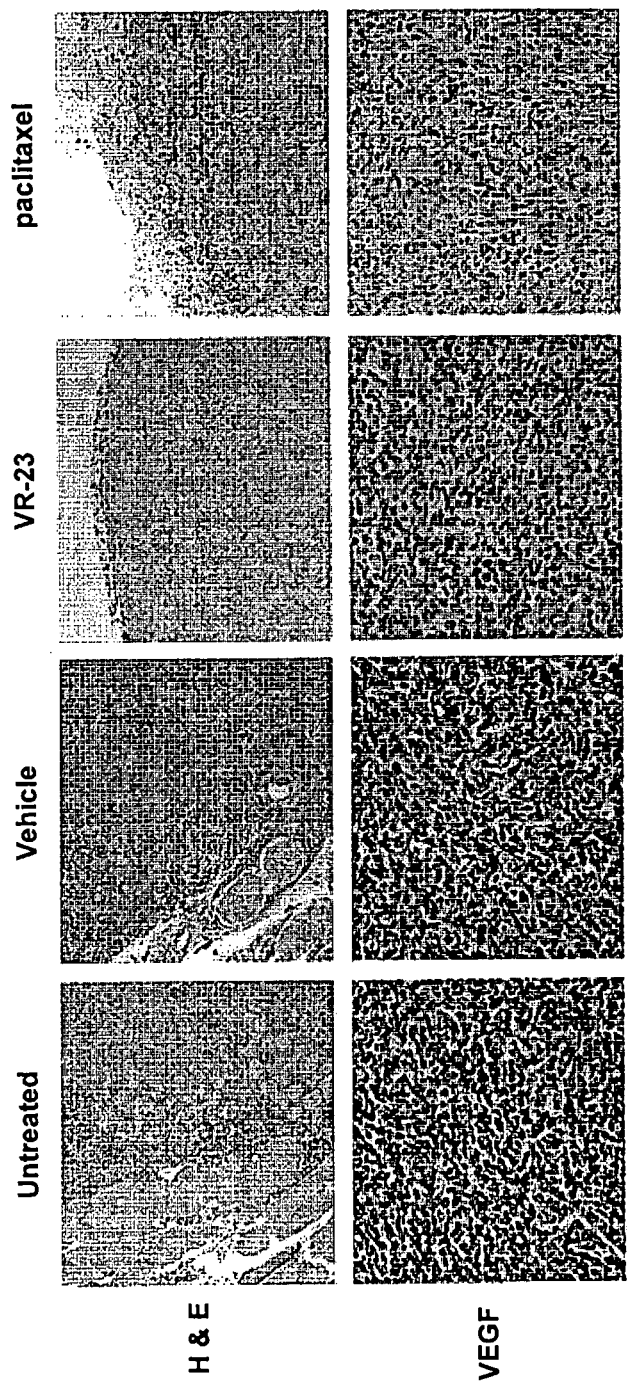
FIG. 28 shows the effect of VR-23 on angiogenesis in samples taken from ATH490 mice engrafted with MDA-MB231 cells and treated with VR-23 or paclitaxel, which samples were stained with hematoxylin and eosin ("H & E") or with an antibody specific for VEGF.

As shown in FIG. 28, VR-23 inhibited angiogenesis and the spread of tumor cells to surrounding tissue/organs in ATH490 mice engrafted with MDA-MB231 cells and which mice were either untreated, sham treated (vehicle), treated with VR-23 or paclitaxel for four weeks as described in Table IX and in the Materials and Methods section herein with respect to Animal Studies. Tumor samples were either stained with hematoxylin and eosin (H & E) or immunostained with an antibody specific for VEGF. Tumor cells infiltrated the muscular tissues or lymphatic vessels in the untreated and sham treated control samples. In contrast, tumors from the VR-23-treated mice showed intact margin without any trace of capillary vessels. Furthermore, VR-23-treated sample did not show any notable amount of VEGF. Images were taken with a 10× objective.

Example 31

Figure 29:
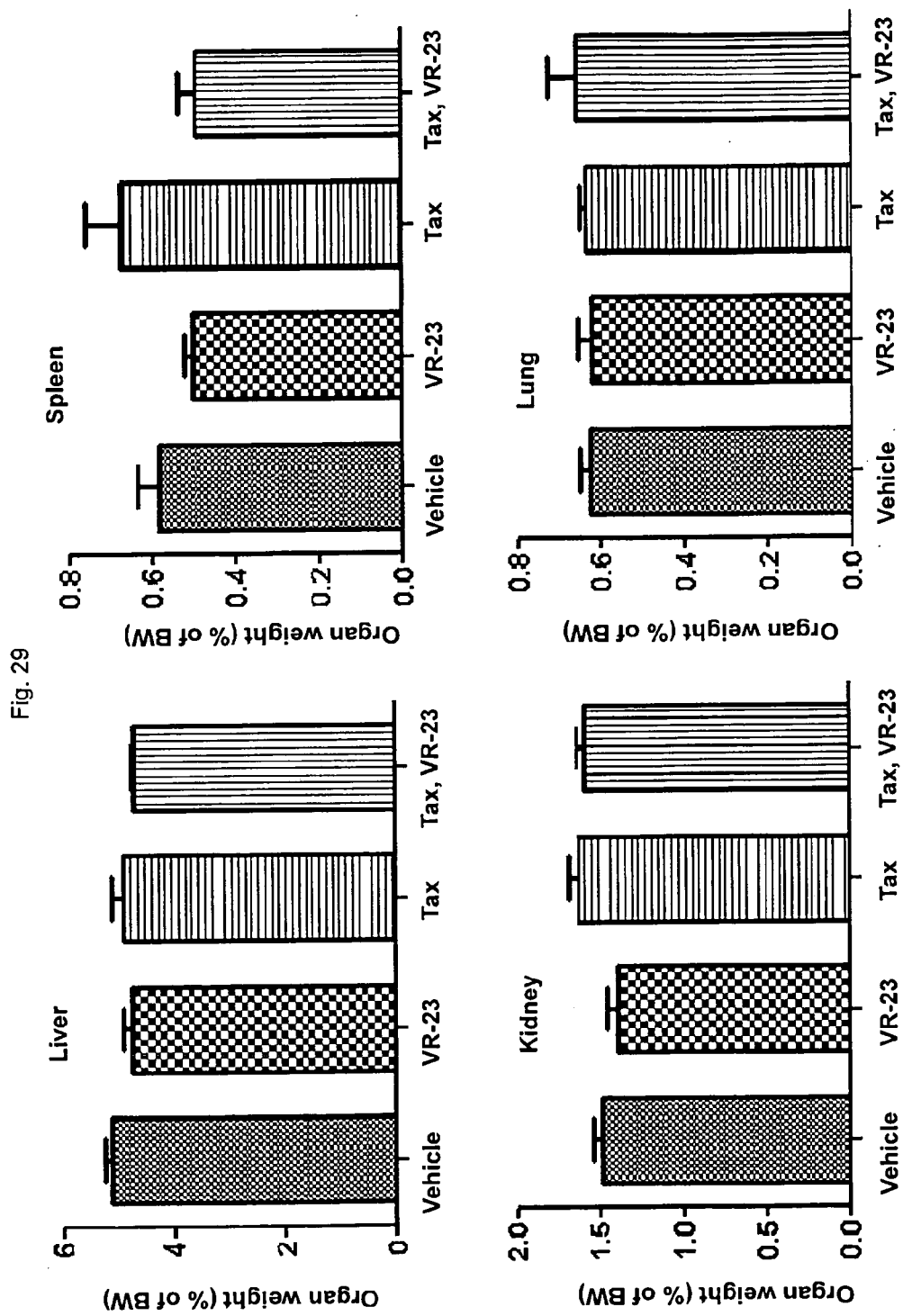
FIG. 29 shows the effect of VR-23, alone or in combination with paclitaxel (referred to "Tax" in the figure), on the organ weight of ATH490 mice so treated. "Vehicle" refers to sham treated control.

As shown in FIG. 29, VR-23 did not cause any notable ill effects on vital organs of ATH490 mice, as determined by their weights. Four different organs (liver, spleen, kidney and lung) of ATH490 mice were measured at 29 days post-treatment with vehicle, VR-23, paclitaxel (Tax) or VR-23 and paclitaxel, as described in Table IX. The organ weights of mice treated with VR-23 (30 mg/kg) maintained similar levels compared to those in sham-treated controls. All values are presented as mean±S.E.M. Analyses were performed using GraphPad Prism software (GraphPad Software). Comparison between the groups was made by p value determination using one-way ANOVA. A p value of <0.05 was considered to be statistically significant. The analyses show that there are no significant difference in organ mass among the treated groups (p values for liver, spleen, kidney and lung are 0.25, 0.085, 0.06, and 0.91, respectively). However, it was consistently observed that the weight of spleen was higher in the paclitaxel-treated animals (Tax) than animals with other treatments, including the combination of VR-23 and paclitaxel. Each organ weight (%) is normalized with total body weight (BW).

Example 32

Figure 30A:
FIG. 30 shows the effect of VR-23, alone or in combination with paclitaxel, on the formation of mitotic cells in the liver of ATH490 mice so treated, as determined by analysis of liver tissue (FIG. 30A) and by summarizing the number of mitotic cells found in the analysis in graphical form (FIG. 30B).
Figure 30B:
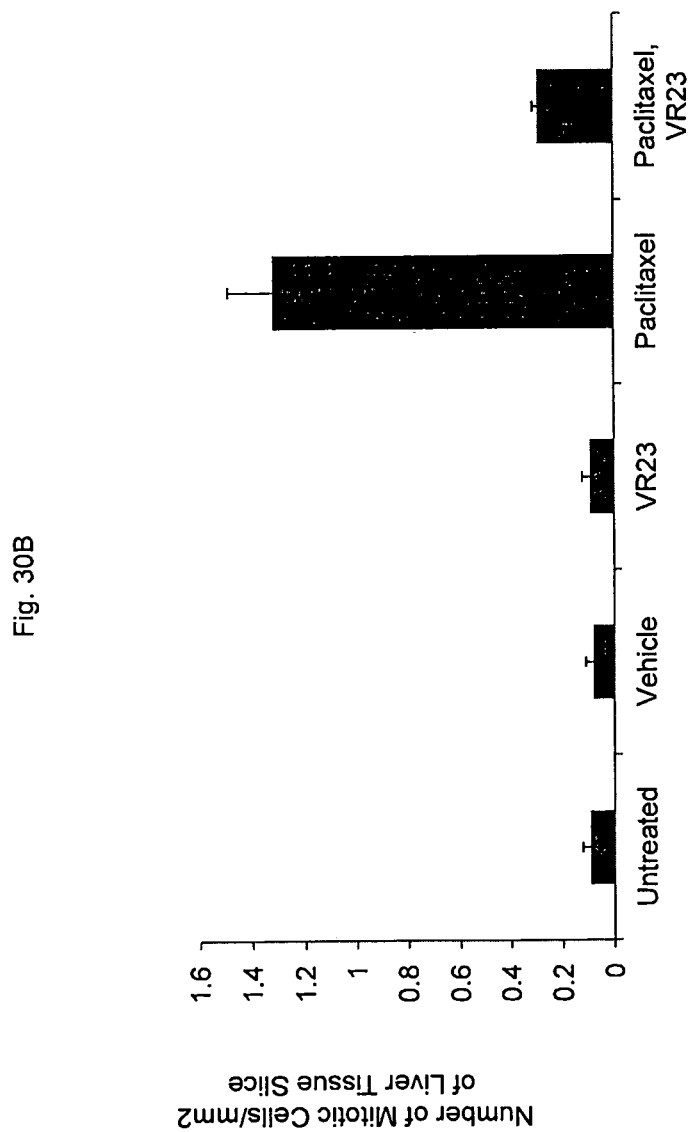

As shown in FIG. 30, VR-23 did not cause an increase in mitotic index in the liver of ATH490 mouse. With respect to FIG. 30A, liver tissues of untreated, sham control and VR-23 (30 mg/kg)-treated sample taken up to 29 days post-treatment showed normal morphology. In contrast, livers of paclitaxel-treated animal (20 mg/kg) showed cells with densely stained nucleic acids in approximately 15% of the cases analyzed. The H&E stained slides were taken with a 20× objective using a Zeiss EPI-fluorescent microscope (bright field). Arrows point to areas of mitotic cells. With respect to FIG. 30B, livers of paclitaxel-treated samples showed a high number of mitotic cells, which were reduced in the presence of 30 mg/kg VR-23. At least 10 fields for each slide (one slide per mouse, and 3 mice per group) were examined. P value is <0.0001. Table XI provides a summary of the observed effects of VR-23 on the liver of ATH490 mice.

Example 33

As shown in Table XII, VR-23 did not show any significant liver toxicity in CD-1 mice (A) or ATH490 mice (B) as determined by the level and ratio of ALT (alanine transaminase) and AST (aspartate aminotransferase). VR-23 (up to 20 mg/kg) did not cause any significant liver toxicity in CD-1 mice as determined by the level of serum ALT. VR-23 (30 mg/kg) did not cause any significant liver toxicity in ATH490 athymic mice as determined by the ratio of ALT and AST. Ratio of <2 is considered normal.

Example 34

Figure 31:
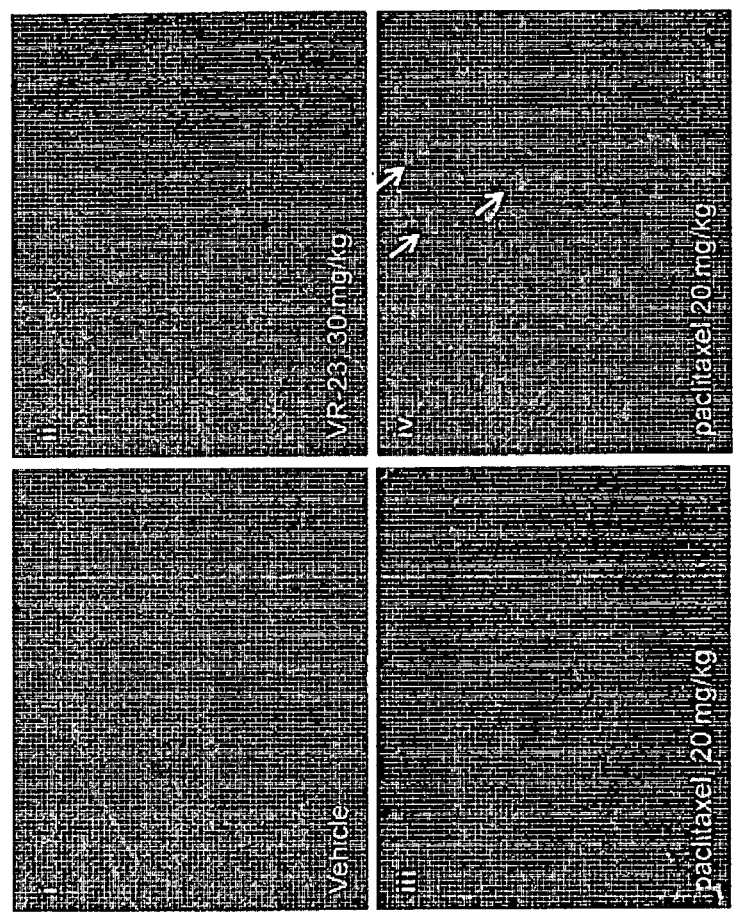
FIG. 31 shows representative images of the effect of VR-23 or paclitaxel on the spleen of ATH490 mice so treated.

As shown in FIG. 31, VR-23 did not cause any notable toxicity to the spleen of ATH490 mice. H&E stained spleen tissues showed normal spleen structure in VR-23-treated mice (30 mg/kg). In contrast, animals treated with paclitaxel (20 mg/kg) showed side effects including germinal center (GC) expansion (FIG. 31, iii), an increase in cellularity, hyperplasia of myeloid and lymphoid cells (FIG. 31, iv, arrows), and thickened/inflamed capsule. Images were taken with a 10× objective using a Zeiss EPI-fluorescent microscope. Arrows indicate the presence of macrophages in the red pulp (RP). Drug administration was carried out as described in Table IX and in the Materials and Methods section herein with respect to Animal Studies.

Example 35

Figure 32:
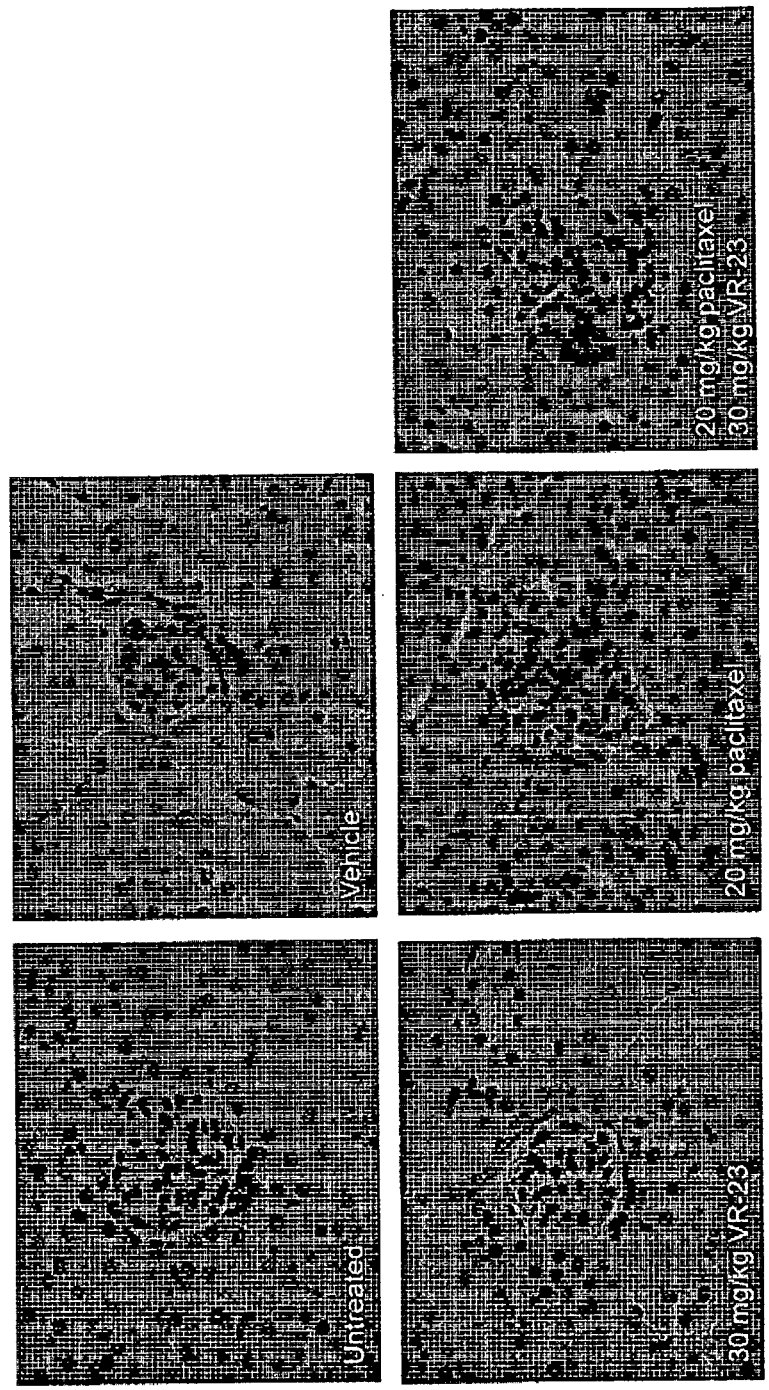
FIG. 32 shows representative images of the effect of VR-23, alone or in combination with paclitaxel, on the kidney of ATH490 mice so treated.

As shown in FIG. 32, VR-23 did not cause any notable toxicity to the kidney of ATH490 mice. Nephrotoxicity was analyzed after ATH490 mice were treated with VR-23 (30 mg/kg) or paclitaxel (20 mg/kg) for four weeks. The kidney sample from VR-23-treated mice showed normal morphology. In contrast, the sample from paclitaxel-treated mice showed high cellularity, endocapillary proliferative glomerulonephritis (enlarged glomeruli), and collapsed Bowman space. The level of paclitaxel-induced high cellularity in spleen cells was reduced when animals were sequentially treated with paclitaxel (20 mg/kg) and VR-23 (30 mg/kg) as described in Table IX. The images of the H&E stained renal tissues were taken with a Zeiss EPI-fluorescent (bright field) microscope using a 10× objective.

Discussion

Thirty-five quinoline derived sulfonyl analogs were designed and synthesized by a hybrid pharmacophore approach, and then examined for their antiproliferative and antitumor activities. The activities of these compounds were initially determined using three different human breast tumor cell lines (MDA-MB231, MDA-MB468 and MCF7) and two matching non-cancer breast epithelial cell lines (184B5 and MCF10A). The mode of function of the compound VR-23 was further characterized using MCF7, HeLa S3 (cervical cancer cell line), Jurkat (lymphoma cell line), U87MG (glioblastoma-astrocytoma cell line), and 184B5 and MCF10A cells; and the antitumor activity of VR-23 was determined using CD-1 and ATH490 athymic mice. From these studies, it was found that: (i) VR-23 functions in a cancer specific manner, as it killed cancer cells 2.6-17.6 fold more effectively than matching non-cancer cells, determined by an in vitro breast (cancer) model; (ii) an in vitro study shows that VR-23 is at least 20 times more effective than temozolomide on U87MG brain cancer cells (Tables V and VI); (iii) VR-23 has shown synergistic effects when combined with other anticancer/antiproliferative agents such as Bortezomib and Paclitaxel; (iv) VR-23 almost completely inhibits 20S proteasome activity at 1 µM; (v) cells treated with VR-23 showed high levels of cyclins B and E, showing that the timely degradation of these cyclins was deregulated by the VR-23 proteasome inhibition activity; (vi) VR-23 caused centrosome amplification throughout the cell cycle, mainly due to the high level of cyclin E and its localization to the centrosome; (vii) the knockdown of cyclin E completely suppressed VR-23-induced centrosome amplification; (viii) the presence of multiple centrosomes in single cells caused abnormal chromosome and cell segregation; (ix) deregulation of Cdk1 and failing of cyclin B degradation by VR-23 resulted in the cell cycle arrest at prometaphase; (x) the VR-23 mediated deregulation of the control mechanism eventually led to the induction of apoptosis in cancer cells, but not in non-cancer cells; (xi) VR-23 at 30 mg/kg twice per week (i.p) for three weeks resulted in the 4.6-fold decrease of tumor size, compared to sham-treated control; (xii) the combination of paclitaxel (20 mg/kg/week) and VR-23 (30 mg/kg/week) (sequential treatment) for three weeks reduced the average tumor size by 29 fold at day 22, compared to untreated control; (xiii) VR-23 did not show any notable side effects to animals, in contrast to Paclitaxel, which showed toxicity to animals; and (xiv) when used in combination, VR-23 reduced paclitaxel-induced toxic effects on spleen and kidney in ATH490 mice. Thus, VR-23 may be useful as an anticancer drug with low side effects, particularly when used in combination with another anticancer drug.

In Vitro Cell Culture-Based Study of VR-23

VR-23 is a proteasome inhibitor and it killed cells in a cancer-specific manner. The VR-23 mediated inactivation of proteasome inhibited the timely degradation of certain cellular proteins such as cyclins B and E, resulting in centrosome amplification. Centrosome is normally duplicated only once per cell cycle in early S phase. However, a cell treated with VR-23 continued to amplify its centrosome throughout the cell cycle. This, in turn, led to a complete disarray of the cell segregation process and, eventually cell death.

Cyclin E is a positive cell cycle regulator for the progression of a cell from late G1 to S phase. In addition, cyclin E is required for centrosome duplication and reduplication[15-17]. In the absence of Orc1, cyclin E can prematurely trigger the disengagement of a duplicated centriole, leading to its reduplication[17]. Overall, the present data suggests that the failing of timely degradation of cyclin E is a mechanism of how centrosome is amplified in cells treated with VR-23. This is supported by the observation that, unlike in control cells, cyclin E is localized to the amplified centrosomes in the cell treated with VR-23 (FIG. 16). It is noted that proteasome is also localized to the centrosomes[12,13]. Furthermore, knockdown of cyclin E with siRNA suppressed VR-23-induced centrosome amplification (FIG. 21A and FIG. 21B). This suggests that cyclin E in the centrosome is not degraded in a timely manner in cells treated with VR-23 due to its inhibition of proteasome activity.

As described below, de novo centrosome synthesis may also contribute to centrosome amplification in cancer cells treated with VR-23.

As herein described, the subcellular localization of proteins known to be involved in centrosome biogenesis was analyzed. Cells arrested at G1/S by DT were released into cell cycle at time 0 hour for 1, 2 or 3 hour(s) in the absence or presence of VR-23. As shown in FIG. 16, cyclin E was not localized to the centrosome up to 2 hour post-DT, regardless of VR-23 treatment. However, cyclin E was localized to the (amplified) centrosomes by the 3 hour time-point in the presence, but not absence, of VR-23. Similarly, Plk1, cyclin A and hSAS6 were localized to the supernumerary centrosomes induced by VR-23 at the 3 hour post-DT time-point (FIG. 17 & FIG. 20).

Unlike Plk1 and cyclin E, Plk4 was localized to the centrosome during the first 3 hour post-DT in the untreated control (FIG. 18, inset boxes #1-3). In the presence of VR-23, however, Plk4 was not localized to the centrosomes for up to 2 hour post-DT (FIG. 18, inset box #4 and data now shown). By 3 hour post-DT, most of the 'small' centrosomes contained Plk4, while 'large' centrosomes did not (FIG. 18). In addition, Plk4 was also found in the nucleoli of the VR-23 treated samples at 3 hour post-DT (FIG. 18, solid arrow).

The present data suggests that centrosome amplification by VR-23 leads to mitotic abnormality including lack of coordinated microtubule attachment to the kinetochore, nondisjuction, chromosome breakage, prolonged cell cycle arrest at prometaphase. These abnormalities eventually lead to cell death by apoptosis.

Progression from G2 to cytokinesis through mitosis requires a precise coordination between several kinases and phosphatases. Among them, the Cdk1/cyclin B kinase plays a key role in driving cell cycle from prometaphase to metaphase. To be activated, Cdk1 must be phosphorylated at the Thr161 residue and dephosphorylated at Tyr15. Even when Thr161 is phosphorylated by CAK, active Wee1 (and inactive Cdc25) can still hold off the cell cycle progression by phosphorylating Cdk1 at Tyr15. When a cell is ready to pass through M phase, Tyr15 is dephosphorylated by Cdc25. Thus, the cell cycle transition from G2 to M phase is essentially regulated by the fine balance between Wee1 kinase and Cdc25 phosphatase activities. VR-23 causes deregulation of this fine control mechanism.

As a cell passes through M phase, mitotic spindles bind to the kinetochore which, in turn, helps to align all the chromosomes at the center of the cell. A proper tension of microtubules by mitotic checkpoint triggers the activation of APC (i.e., bound by Cdc20), which ubiquitinates and degrades securin and cyclin B, to pass through the cell cycle beyond M phase. It was found that a cell treated with VR-23 was mostly arrested just prior to the dephosphorylation of Cdk1 at Tyr15, and the level of cyclin B was still high by the 2 hour post-nocodazole arrest point (FIG. 23). The high level of cyclin B could be the direct result of VR-23-mediated APC inhibition and/or indirect consequence of cell cycle arrest prior to the mitotic checkpoint. Data from confocal microscopy showed that some VR-23 treated cells form mitotic spindle, albeit abnormal (FIG. 15), which may be able to activate cyclin B degradation. When this happens, cyclin B degradation can be directly inhibited by VR-23 mediated proteasome inhibition. However, data from the co-immunoprecipitation experiment (FIG. 24) showed that most cells treated with VR-23 did not progress to metaphase. In this case, the degradation of cyclin B may never be triggered, since the mitotic checkpoint has not yet been activated.

A Study of VR-23 Using an In Vivo Xenograft Model

ATH490 athymic mice engrafted with MDA-MB231 breast cancer cells and treated with VR-23 (30 mg/kg twice per week) for three weeks showed a reduced tumor burden (a 4.6-fold decrease) and tumor cell proliferation (FIG. 25, FIG. 26 and Table X). This VR-23 efficacy is lower than that of paclitaxel at 20 mg/kg/week (a 18.4-fold reduction). However, the side effects of VR-23 are lower than those of paclitaxel. Furthermore, the combination of VR-23 (30 mg/kg) and paclitaxel (20 mg/kg) reduced the tumor burden by 29 fold of the control, showing that a combination of VR-23 with paclitaxel (or other anticancer agents) can be a useful anticancer therapy.

The in vitro studies herein described showed that VR-23 killed cells in a cancer-specific manner. Treatment of CD-1 athymic mice with 25 mg/kg/week of VR-23 did not show any ill effect as determined by the changes in body weights (FIG. 27A). In addition, treatment of ATH490 athymic mice with VR-23 at 30 mg/kg twice a week also did not cause any notable ill effect on body weight, when compared to the untreated control (FIG. 27B).

Examination of four vital organs (liver, spleen, kidney, and lung) of mice treated with VR-23 showed that VR-23 did not have any ill effects on any of these organs; however, paclitaxel at 20 mg/kg per week for four weeks caused an increase in weight of spleen (FIG. 29). Further, paclitaxel treatment resulted in an increase in liver mitotic index, while VR-23 treatment did not (FIG. 30B). The liver mitotic index of paclitaxel-treated animals was reduced in the presence of VR-23 (30 mg/kg) (FIG. 30B). Also, the ALT/AST ratio of VR-23-treated mice was not significantly distinguishable to that of untreated control, while that of paclitaxel-treated animal was elevated by 30-50% in ATH490 mice (Table XII).

Unlike VR-23 (30 mg/kg), paclitaxel (20 mg/kg) caused a number of ill effects on ATH490 mice, including the expansion of germinal center, an increase in cellularity, and the hyperplasia of myeloid and lymphoid cells in the spleen (FIG. 31). Similarly, VR-23 (30 mg/kg, four weeks) did not cause any notable abnormality in kidney (FIG. 32). In contrast, kidneys from paclitaxel-treated mice showed high cellularity, endocapillary proliferative glomerulonephritis, and often collapsed Bowman space. This paclitaxel-induced cellularity was reduced when animals were treated in combination with 30 mg/kg of VR-23 in a sequential fashion as described in Table IX. Thus, not only was VR-23 non-toxic to animals but it also reduced toxicity caused by paclitaxel (and may also be useful to reduce the toxicity of other anticancer drugs). Thus, VR-23 may also be useful in combinational therapies.

REFERENCES

1. Hu, C., Solomon, V. R., Ulibarri, G., and Lee, H. The efficacy and selectivity of tumor cell killing by Akt inhibitors are substantially increased by chloroquine. *Bioorg Med Chem* 16, 7888-7893 (2008).
2. Solomon, V. R. and Lee, H. Quinoline as a privileged scaffold in cancer drug discovery. *Curr Med Chem* 18, 1488-1508 (2011).
3. Solomon, V. R., Hu, C., and Lee, H. Design and synthesis of chloroquine analogs with anti-breast cancer property. *Eur J Med Chem* 45, 3916-3923 (2010).
4. Solomon, V. R. and Lee, H. Chloroquine and its analogs: a new promise of an old drug for effective and safe cancer therapies. *Eur J Pharmacol* 625, 220-233 (2009).
5. Zhang, H., et al. Synthesis and in vitro cytotoxicity evaluation of 4-aminoquinoline derivatives. *Biomed Pharmacother.* 62, 65-69 (2008).
6. Solomon, V. R., Hu, C., and Lee, H. Hybrid pharmacophore design and synthesis of isatin-benzothiazole analogs for their anti-breast cancer activity. *Bioorg Med Chem* 17, 7585-7592 (2009).
7. Solomon, V. R., Hu, C., and Lee, H. Design and synthesis of anti-breast cancer agents from 4-piperazinylquinoline: a hybrid pharmacophore approach. *Bioorg Med Chem* 18, 1563-1572 (2010).
8. Ozawa, Y., et al. E7070, a novel sulphonamide agent with potent antitumour activity in vitro and in vivo. *Eur J Cancer* 37, 2275-2282 (2001).
9. Tanaka, H., et al. HMN-176, an active metabolite of the synthetic antitumor agent HMN-214, restores chemosensitivity to multidrug-resistant cells by targeting the transcription factor NF-Y. *Cancer Res* 63, 6942-6947 (2003).
10. Abbate, F., et al. Carbonic anhydrase inhibitors: E7070, a sulfonamide anticancer agent, potently inhibits cytosolic isozymes I and II, and transmembrane, tumor-associated isozyme IX. *Bioorg Med Chem Lett* 14, 217-223 (2004).
11. Santi, S. A. and Lee, H. Ablation of Akt2 induces autophagy through cell cycle arrest, the downregulation of p70S6K, and the deregulation of mitochondria in MDA-MB231 cells. *PLoS One* 6, e14614 (2011).

12. Wigley, W. C., et al. Dynamic association of proteasomal machinery with the centrosome. *J Cell Biol* 145, 481-490 (1999).
13. Freed, E., et al. Components of an SCF ubiquitin ligase localize to the centrosome and regulate the centrosome duplication cycle. *Genes Dev* 13, 2242-2257 (1999).
14. Peters, J. M. The anaphase promoting complex/cyclosome: a machine designed to destroy. *Nat Rev Mol Cell Biol* 7, 644-656 (2006).
15. Lacey, K. R., Jackson, P. K., and Stearns, T. Cyclin-dependent kinase control of centrosome duplication. *Proc Natl Acad Sci U.S.A* 96, 2817-2822 (1999).
16. Hinchcliffe, E. H., et al. Requirement of Cdk2-cyclin E activity for repeated centrosome reproduction in *Xenopus* egg extracts. *Science* 283, 851-854 (1999).
17. Hemerly, A. S., Prasanth, S. G., Siddiqui, K., and Stillman, B. Orc1 controls centriole and centrosome copy number in human cells. *Science* 323, 789-793 (2009).
18. Faust et al. Differential p38-dependent signalling in response to cellular stress and mitogenic stimulation in fibroblasts. *Cell Communication and Signaling*, 10:6 (2012).

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present disclosure is not entitled to antedate such publication by virtue of prior invention.

Although the foregoing disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

TABLE I

Exemplary compounds of Formula (I).

| Structure No | Compound Structure | (a) Experiment Book Code (b) Chemical names |
|---|---|---|
| 1. | 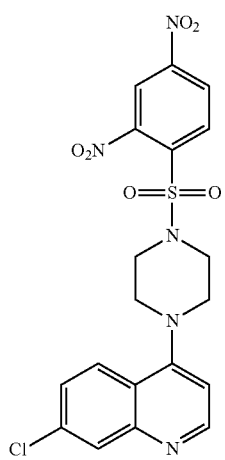 [SMILES: O=[N+]([O-])c1ccc(S(=O)(=O)N2CCN(c3ccnc4cc(Cl)ccc34)CC2)c([N+](=O)[O-])c1] | (a) VR-23<br>(b) 7-Chloro-4-(4-(2,4-dinitrophenylsulfonyl)piperazin-1-yl)quinoline |
| 2. | 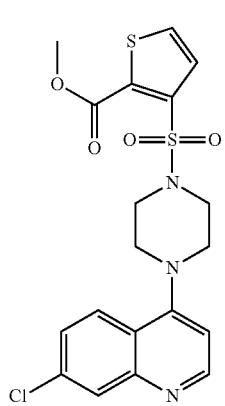 [SMILES: COC(=O)c1sccc1S(=O)(=O)N1CCN(c2ccnc3cc(Cl)ccc23)CC1] | (a) VR-36<br>(b) Methyl 3-(4-(7-chloroquinolin-4-yl)piperazin-1-ylsulfonyl)thiophene-2-carboxylate |

TABLE I-continued

Exemplary compounds of Formula (I).

| Structure No | Compound Structure | (a) Experiment Book Code<br>(b) Chemical names |
|---|---|---|
| 3. | 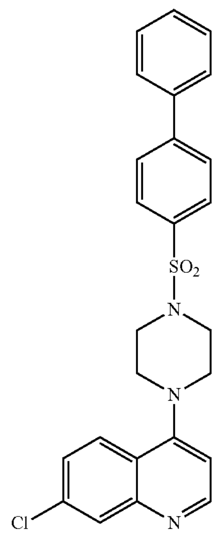 [SMILES: O=S(=O)(c1ccc(-c2ccccc2)cc1)N1CCN(c2ccnc3cc(Cl)ccc23)CC1] | (a) VR-34<br>(b) 7-Chloro-4-(4-(biphenylsulfonyl)piperazin-1-yl)quinoline |
| 4. | 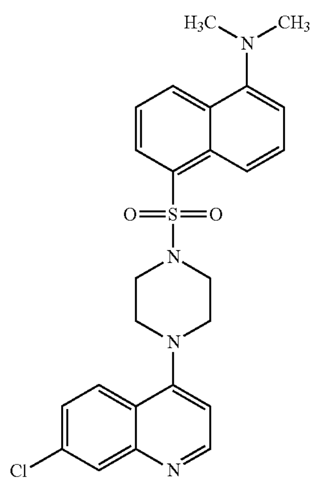 [SMILES: CN(C)c1cccc2c(S(=O)(=O)N3CCN(c4ccnc5cc(Cl)ccc45)CC3)cccc12] | (a) VR-37<br>(b) 5-(4-(7-Chloroquinolin-4-yl)piper-azin-1-ylsulfonyl)-N,N-dimethylnaphthalen-1-amine |
| 5. | 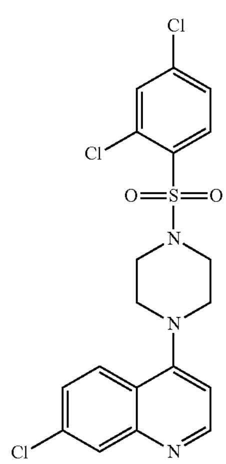 [SMILES: O=S(=O)(c1ccc(Cl)cc1Cl)N1CCN(c2ccnc3cc(Cl)ccc23)CC1] | (a) VR-35<br>(b) 7-Chloro-4-(4-(2,4-dichlorophenylsulfonyl)piperazin-1-yl)quinoline |

TABLE I-continued

Exemplary compounds of Formula (I).

| Structure No | Compound Structure | (a) Experiment Book Code (b) Chemical names |
|---|---|---|
| 6. | 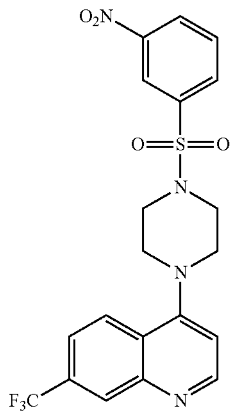 [SMILES: O=[N+]([O-])c1cccc(S(=O)(=O)N2CCN(c3ccnc4cc(C(F)(F)F)ccc34)CC2)c1] | (a) VR-41<br>(b) 4-[4-(3-Nitro-benzenesulfonyl)-piperazin-1-yl]-7-trifluoromethyl-quinoline |
| 7. | 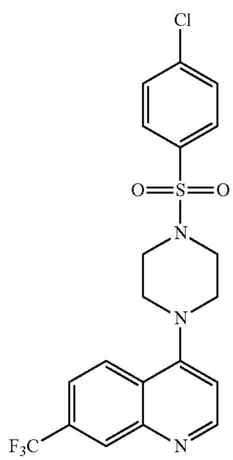 [SMILES: O=S(=O)(c1ccc(Cl)cc1)N1CCN(c2ccnc3cc(C(F)(F)F)ccc23)CC1] | (a) VR-40<br>(b) 4-[4-(4-Chloro-benzenesulfonyl)-piperazin-1-yl]-7-trifluoromethyl-quinoline |
| 8. | 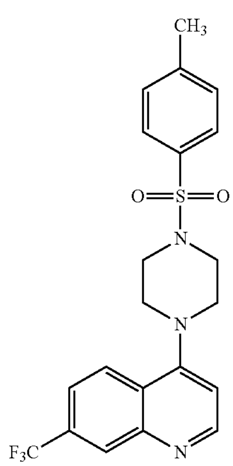 | (a) VR-39<br>(b) 4-[4-(Toluene-4-sulfonyl)-piperazin-1-yl]-7-trifluoromethyl-quinoline |

TABLE I-continued
Exemplary compounds of Formula (I).
| Structure No | Compound Structure | (a) Experiment Book Code<br>(b) Chemical names |
|---|---|---|
| 9. | 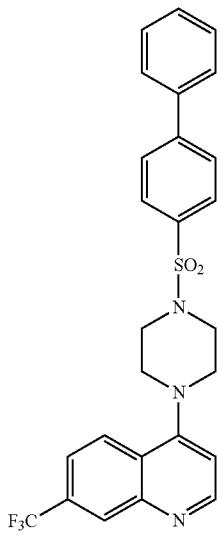 [SMILES: O=S(=O)(c1ccc(-c2ccccc2)cc1)N1CCN(c2ccnc3cc(C(F)(F)F)ccc23)CC1] | (a) VR-43<br>(b) 4-[4-(Biphenyl-4-sulfonyl)-piperazin-1-yl]-7-trifluoromethyl-quinoline |
| 10. | 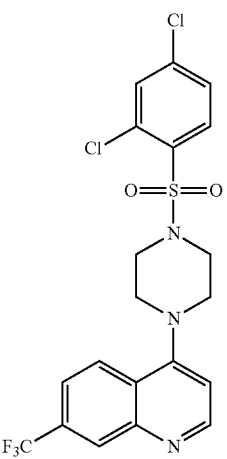 [SMILES: O=S(=O)(c1ccc(Cl)cc1Cl)N1CCN(c2ccnc3cc(C(F)(F)F)ccc23)CC1] | (a) VR-45<br>(b) 4-[4-(2,4-Dichloro-benzenesulfonyl)-piperazin-1-yl]-7-trifluoromethyl-quinoline |
| 11. | 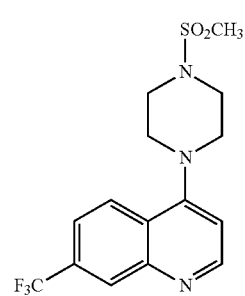 | (a) VR-38<br>(b) 4-(4-Methanesulfonyl-piperazin-1-yl)-7-trifluoromethyl-quinoline |

TABLE I-continued

Exemplary compounds of Formula (I).

| Structure No | Compound Structure | (a) Experiment Book Code / (b) Chemical names |
|---|---|---|
| 12. | (structure) | (a) VR-42<br>(b) 4-[4-(2,4-Dinitro-benzenesulfonyl)-piperazin-1-yl]-7-trifluoromethyl-quinoline |
| 13. | (structure) | (a) VR-44<br>(b) Dimethyl-{5-[4-(7-trifluoromethyl-quinolin-4-yl)-piperazine-1-sulfonyl]-naphthalen-1-yl}-amine |
| 14. | (structure) | (a) VR-46<br>(b) 3-[4-(7-Trifluoromethyl-quinolin-4-yl)-piperazine-1-sulfonyl]-thiophene-2-carboxylic acid methyl ester |
| 15. | (structure) | (a) VR-21<br>(b) N-[3-(7-Chloro-quinolin-4-ylamino)-propyl]-methanesulfonamide |

TABLE I-continued

Exemplary compounds of Formula (I).

| Structure No | Compound Structure | (a) Experiment Book Code (b) Chemical names |
|---|---|---|
| 16. | 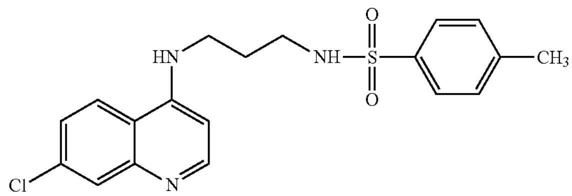 [SMILES: Cc1ccc(S(=O)(=O)NCCCNc2ccnc3cc(Cl)ccc23)cc1] | (a) VR-26<br>(b) N-[3-(7-Chloro-quinolin-4-ylamino)-propyl]-4-methyl-benzenesulfonamide |
| 17. | 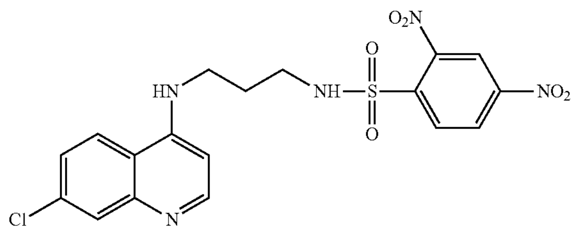 [SMILES: O=[N+]([O-])c1ccc(S(=O)(=O)NCCCNc2ccnc3cc(Cl)ccc23)c([N+](=O)[O-])c1] | (a) VR-27<br>(b) N-[3-(7-Chloro-quinolin-4-ylamino)-propyl]-2,4-dinitro-benzenesulfonamide |
| 18. | 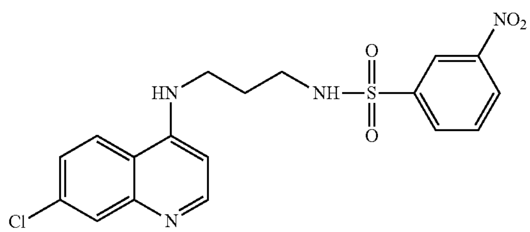 [SMILES: O=[N+]([O-])c1cccc(S(=O)(=O)NCCCNc2ccnc3cc(Cl)ccc23)c1] | (a) VR-32<br>(b) N-(3-(7-Chloroquinolin-4-ylamino)propyl)-3-nitrobenzenesulfonamide |
| 19. | 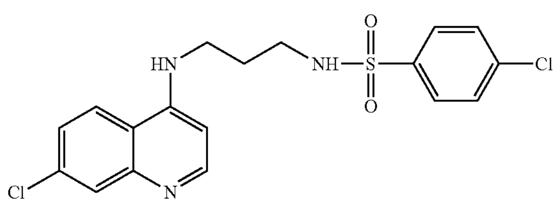 [SMILES: O=S(=O)(NCCCNc1ccnc2cc(Cl)ccc12)c1ccc(Cl)cc1] | (a) VR-33<br>(b) 4-Chloro-N-(3-(7-chloroquinolin-4-ylamino)propyl)benzenesulfonamide |
| 20. | 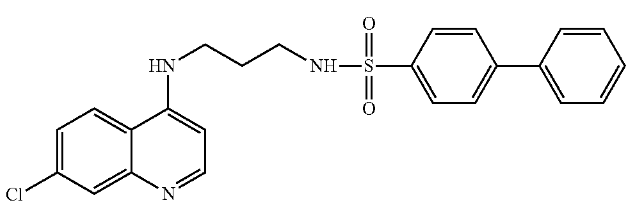 [SMILES: O=S(=O)(NCCCNc1ccnc2cc(Cl)ccc12)c1ccc(-c2ccccc2)cc1] | (a) VR-52<br>(b) Biphenyl-4-sulfonic acid [3-(7-chloro-quinolin-4-ylamino)-propyl]-amide |
| 21. | 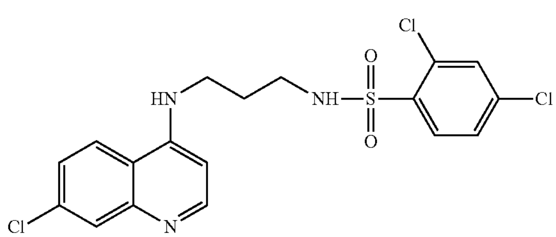 [SMILES: O=S(=O)(NCCCNc1ccnc2cc(Cl)ccc12)c1ccc(Cl)cc1Cl] | (a) VR-66<br>(b) 2,4-Dichloro-N-[3-(7-chloro-quinolin-4-ylamino)-propyl]-benzenesulfonamide |
| 22. | 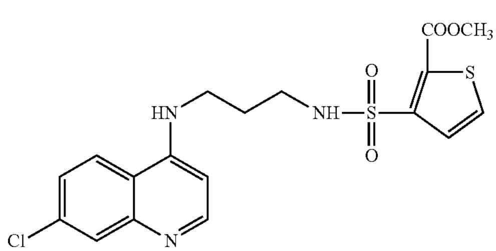 [SMILES: COC(=O)c1sccc1S(=O)(=O)NCCCNc1ccnc2cc(Cl)ccc12] | (a) VR-67<br>(b) N-(3-(7-Chloroquinolin-4-ylamino)propyl)thiophene-3-sulfonamide-2-carbomethoxy ester |

TABLE I-continued

Exemplary compounds of Formula (I).

| Structure No | Compound Structure | (a) Experiment Book Code (b) Chemical names |
|---|---|---|
| 23. | 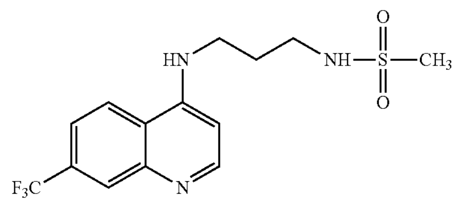 [SMILES: CS(=O)(=O)NCCCNc1ccnc2cc(C(F)(F)F)ccc12] | (a) VR-57<br>(b) N-[3-(7-Trifluoromethyl-quinolin-4-ylamino)-propyl]-methanesulfonamide |
| 24. | 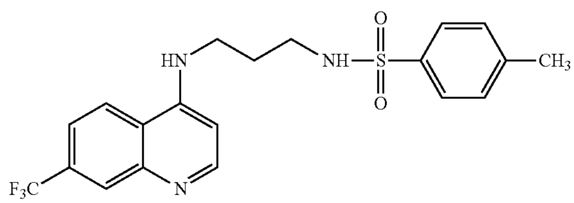 [SMILES: Cc1ccc(S(=O)(=O)NCCCNc2ccnc3cc(C(F)(F)F)ccc23)cc1] | (a) VR-56<br>(b) 4-Methyl-N-[3-(7-trifluoromethyl-quinolin-4-ylamino)-propyl]-benzenesulfonamide |
| 25. | 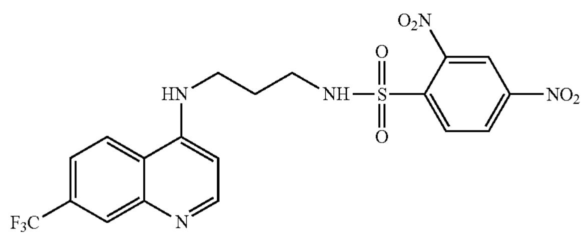 [SMILES: O=[N+]([O-])c1ccc(S(=O)(=O)NCCCNc2ccnc3cc(C(F)(F)F)ccc23)c([N+](=O)[O-])c1] | (a) VR-59<br>(b) 2,4-Dinitro-N-[3-(7-trifluoromethyl-quinolin-4-ylamino)-propyl]-benzenesulfonamide |
| 26. | 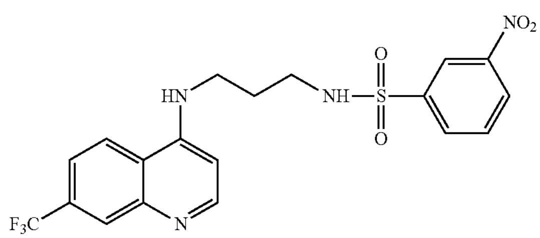 [SMILES: O=[N+]([O-])c1cccc(S(=O)(=O)NCCCNc2ccnc3cc(C(F)(F)F)ccc23)c1] | (a) VR-58<br>(b) 3-Nitro-N-[3-(7-trifluoromethyl-quinolin-4-ylamino)-propyl]-benzenesulfonamide |
| 27. | 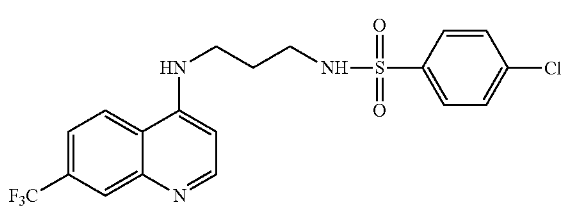 [SMILES: O=S(=O)(NCCCNc1ccnc2cc(C(F)(F)F)ccc12)c1ccc(Cl)cc1] | (a) VR-60<br>(b) 4-Chloro-N-[3-(7-trifluoromethyl-quinolin-4-ylamino)-propyl]-benzenesulfonamide |
| 28. | 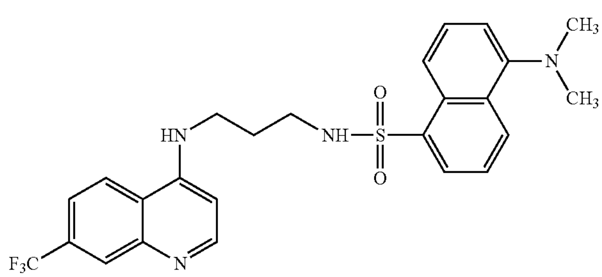 [SMILES: CN(C)c1cccc2c(S(=O)(=O)NCCCNc3ccnc4cc(C(F)(F)F)ccc34)cccc12] | (a) VR-63<br>(b) 5-Dimethylamino-naphthalene-1-sulfonic acid [3-(7-trifluoromethyl-quinolin-4-ylamino)-propyl]-amide |

TABLE I-continued

Exemplary compounds of Formula (I).

| Structure No | Compound Structure | (a) Experiment Book Code (b) Chemical names |
|---|---|---|
| 29. | 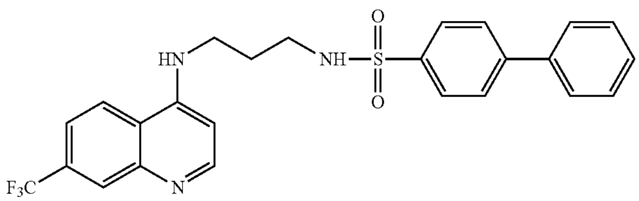 [SMILES: O=S(=O)(NCCCNc1ccnc2cc(C(F)(F)F)ccc12)c1ccc(-c2ccccc2)cc1] | (a) VR-61 (b) Biphenyl-4-sulfonic acid [3-(7-trifluoromethyl-quinolin-4-ylamino)-propyl]-amide |
| 30. | 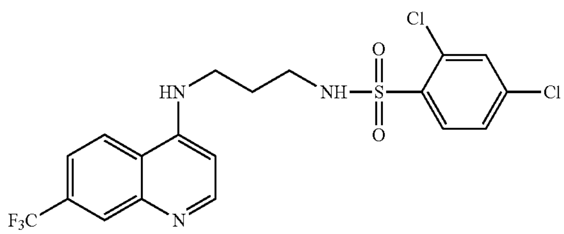 [SMILES: O=S(=O)(NCCCNc1ccnc2cc(C(F)(F)F)ccc12)c1ccc(Cl)cc1Cl] | (a) VR-62 (b) 2,4-Dichloro-N-[3-(7-trifluoromethyl-quinolin-4-ylamino)-propyl]-benzenesulfonamide |
| 31. | 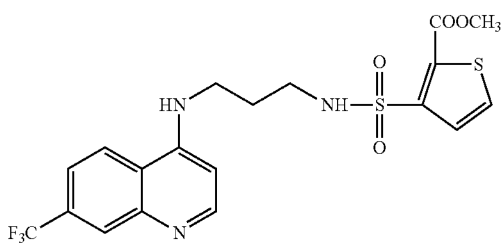 [SMILES: COC(=O)c1sccc1S(=O)(=O)NCCCNc1ccnc2cc(C(F)(F)F)ccc12] | (a) VR-64 (b) N-(3-(7-Trifluoromethyl-quinolin-4-ylamino)propyl)thiophene-3-sulfonamide-2-carbomethoxy ester |

TABLE II

| Structure No | Compound Structure | (a) Exp Book Code (b) Chemical names |
|---|---|---|
| 38. | 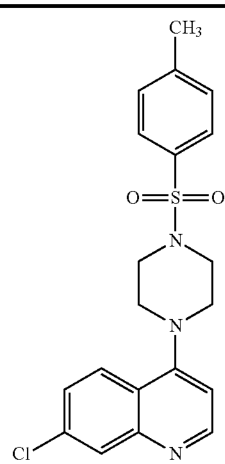 | (a) VR-22 (b) 7-Chloro-4-(4-tosylpiperazin-1-yl)quinoline |

TABLE II-continued

| Structure No | Compound Structure | (a) Exp Book Code (b) Chemical names |
|---|---|---|
| 39. | 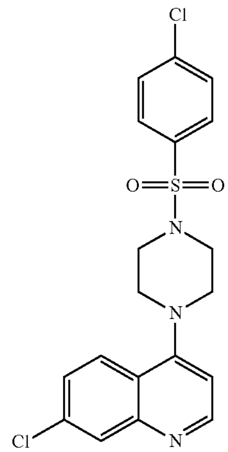 [SMILES: O=S(=O)(c1ccc(Cl)cc1)N1CCN(c2ccnc3cc(Cl)ccc23)CC1] | (a) VR-24 (b) 7-Chloro-4-(4-(4-chlorophenylsulfonyl)piperazin-1-yl)quinoline |
| 40. | 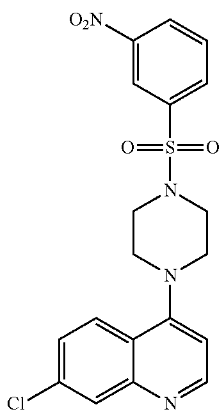 [SMILES: O=[N+]([O-])c1cccc(S(=O)(=O)N2CCN(c3ccnc4cc(Cl)ccc34)CC2)c1] | (a) VR-25 (b) 7-Chloro-4-(4-(3-nitrophenylsulfonyl)piperazin-1-yl)quinoline |
| 41. | 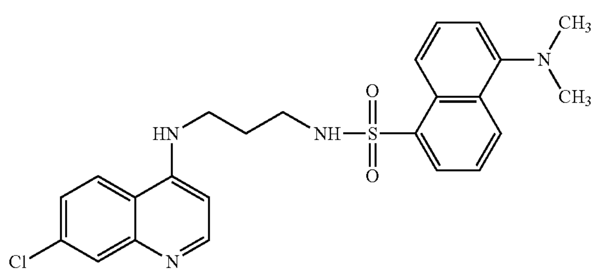 [SMILES: CN(C)c1cccc2c(S(=O)(=O)NCCCNc3ccnc4cc(Cl)ccc34)cccc12] | (a) VR-65 (b) 5-Dimethylamino-naphthalene-1-sulfonic acid [3-(7-chloro-quinolin-4-ylamino)-propyl]-amide |

TABLE III

Antiproliferative activity of quinoline sulfonyl derivatives (compounds 1-31 of Table I) on human breast cancer and non-cancer breast cell lines.

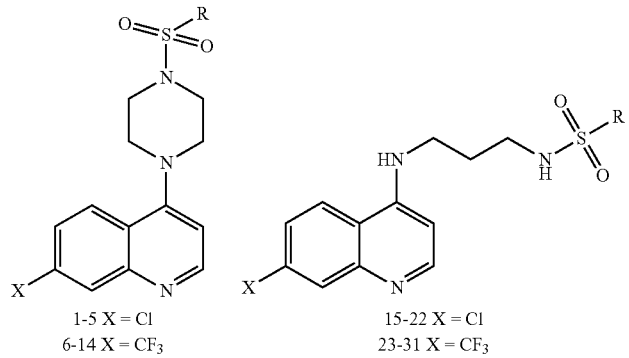

1-5 X = Cl
6-14 X = CF$_3$
15-22 X = Cl
23-31 X = CF$_3$

| Structure No. | X | R | GI$_{50}$ MDA-MB231 | MDA-MB468 | MCF7 | 184B5 |
|---|---|---|---|---|---|---|
| 1 | Cl | 2,4-Dinitrophenyl | 3.41 ± 0.10 | 0.7 ± 0.10 | 2.32 ± 0.80 | 8.99 ± 0.12 |
| 2 | Cl | Thiophenyl-2-carboxylic acid methyl ester | 40.36 ± 0.82 | 30.15 ± 0.71 | 22.37 ± 0.21 | 15.19 ± 0.18 |
| 3 | Cl | Biphenyl | 26.16 ± 0.62 | 18.25 ± 0.54 | 9.23 ± 0.21 | 16.36 ± 0.23 |
| 4 | Cl | N,N-Dimethylnaphthalenyl | 35.04 ± 0.76 | 27.47 ± 0.66 | 22.3 ± 0.18 | 28.25 ± 0.26 |
| 5 | Cl | 2,4-Dichlorophenyl | 40.59 ± 0.81 | 21.63 ± 0.61 | 13.45 ± 0.23 | 12.37 ± 0.15 |
| 6 | CF$_3$ | 3-Nitrophenyl | 32.19 ± 0.68 | 18.55 ± 0.57 | 9.44 ± 0.25 | 17.73 ± 0.21 |
| 7 | CF$_3$ | 4-Chlorophenyl | 41.44 ± 0.83 | 34.91 ± 0.78 | 27.36 ± 0.27 | 21.8 ± 0.26 |
| 8 | CF$_3$ | Tolyl | 42.73 ± 0.83 | 36.54 ± 0.75 | 20.77 ± 0.23 | 12.95 ± 0.14 |
| 9 | CF$_3$ | Biphenyl | 27.21 ± 0.61 | 20.51 ± 0.54 | 14.75 ± 0.19 | 19.09 ± 0.24 |
| 10 | CF$_3$ | 2,4-Dichlorophenyl | 20.27 ± 0.53 | 18.56 ± 0.55 | 16.71 ± 0.19 | 20.44 ± 0.23 |
| 11 | CF$_3$ | Methyl | 44.41 ± 0.85 | 28.58 ± 0.69 | 25.64 ± 0.26 | 93.93 ± 0.89 |
| 12 | CF$_3$ | 2,4-Dinitrophenyl | 24.32 ± 0.63 | 19.15 ± 0.61 | 10.84 ± 0.12 | 37.78 ± 0.35 |
| 13 | CF$_3$ | N,N-dimethylnaphthalenyl | 21.96 ± 0.59 | 18.98 ± 0.55 | 12.85 ± 0.21 | 11.98 ± 0.15 |
| 14 | CF$_3$ | Thiophenyl-2-carboxylic acid methyl ester | 34.74 ± 0.71 | 23.91 ± 0.64 | 15.97 ± 0.24 | 15.88 ± 0.14 |
| 15 | Cl | Methyl | 40.89 ± 1.52 | 28.64 ± 1.03 | 23.14 ± 0.87 | 23.26 ± 0.92 |
| 16 | Cl | Tolyl | 6.16 ± 0.51 | 5.77 ± 0.41 | 5.25 ± 0.45 | 9.56 ± 0.53 |
| 17 | Cl | 2,4-Dinitrophenyl | 8.85 ± 0.71 | 7.35 ± 0.23 | 6.16 ± 0.32 | 9.09 ± 0.56 |
| 18 | Cl | 3-Nitrophenyl | 20.43 ± 1.15 | 9.21 ± 0.65 | 8.62 ± 0.38 | 15.77 ± 0.88 |
| 19 | Cl | 4-Chlorophenyl | 11.78 ± 0.91 | 8.34 ± 0.73 | 4.31 ± 0.32 | 6.36 ± 0.34 |
| 20 | Cl | Biphenyl | 4.63 ± 0.42 | 4.46 ± 0.37 | 2.47 ± 0.23 | 2.41 ± 0.09 |
| 21 | Cl | 2,4-Dichlorophenyl | 6.76 ± 0.55 | 3.61 ± 0.12 | 4.04 ± 0.22 | 3.55 ± 0.21 |
| 22 | Cl | 2-Carbomethoxy-3-thiopheneyl | 5.97 ± 0.47 | 4.18 ± 0.29 | 4.22 ± 0.24 | 15.71 ± 0.41 |
| 23 | CF$_3$ | Methyl | 55.91 ± 1.56 | 30.35 ± 0.99 | 25.32 ± 1.23 | 59.54 ± 1.56 |
| 24 | CF$_3$ | Tolyl | 6.36 ± 0.48 | 6.21 ± 0.42 | 6.90 ± 0.45 | 12.21 ± 0.86 |
| 25 | CF$_3$ | 2,4-Dinitrophenyl | 8.91 ± 0.77 | 8.46 ± 0.41 | 5.56 ± 0.34 | 15.91 ± 0.89 |
| 26 | CF$_3$ | 3-Nitrophenyl | 15.77 ± 0.95 | 9.09 ± 0.57 | 8.25 ± 0.52 | 8.01 ± 0.76 |
| 27 | CF$_3$ | 4-Chlorophenyl | 12.75 ± 0.88 | 10.34 ± 0.56 | 5.44 ± 0.34 | 7.63 ± 0.43 |
| 28 | CF$_3$ | N,N-Dimethylnaphthalenyl | 14.23 ± 0.98 | 9.71 ± 0.33 | 7.73 ± 0.61 | 3.73 ± 0.21 |
| 29 | CF$_3$ | Biphenyl | 6.03 ± 0.38 | 4.19 ± 0.23 | 3.60 ± 0.27 | 2.82 ± 0.05 |
| 30 | CF$_3$ | 2,4-Dichlorophenyl | 6.97 ± 0.54 | 3.94 ± 0.12 | 5.18 ± 0.29 | 3.22 ± 0.08 |
| 31 | CF$_3$ | 2-Carbomethoxy-3-thiopheneyl | 7.48 ± 0.63 | 4.55 ± 0.25 | 4.33 ± 0.23 | 12.05 ± 0.45 |
| | | Chloroquine | 22.52 ± 1.44 | 28.58 ± 1.25 | 38.44 ± 1.20 | 76.13 ± 1.13 |
| | | Cisplatin | 23.65 ± 0.23 | 31.02 ± 0.45 | 25.77 ± 0.38 | 25.54 ± 0.35 |

TABLE IV

GI$_{50}$ values of the four compounds described in Table II.

| Compounds (Structure No.) | X | R | GI$_{50}$ MB231 | MB468 | MCF7 | 184B5 | MCF10A |
|---|---|---|---|---|---|---|---|
| VR-22 (38) | Cl | Tolyl | 6.16 ± 0.51 | 5.77 ± 0.41 | 5.25 ± 0.45 | 9.56 ± 0.53 | 12.61 ± 0.66 |
| VR-24 (39) | Cl | 4-Chlorophenyl | 11.78 ± 0.91 | 8.34 ± 0.73 | 4.31 ± 0.32 | 6.36 ± 0.34 | 9.70 ± 0.81 |
| VR-25 (40) | Cl | 3-Nitrophenyl | 20.43 ± 1.15 | 9.21 ± 0.65 | 8.62 ± 0.38 | 15.77 ± 0.88 | 31.08 ± 1.01 |
| VR-65 (41) | Cl | N,N-Dimethylnaphthalenyl | 12.67 ± 1.01 | 4.63 ± 0.35 | 2.45 ± 0.12 | 1.67 ± 0.08 | 2.56 ± 0.03 |
| Chloroquine | | | 22.52 ± 1.44 | 28.58 ± 1.25 | 38.44 ± 1.20 | 76.13 ± 1.13 | 81.26 ± 1.45 |
| Cisplatin | | | 23.65 ± 0.23 | 31.02 ± 0.45 | 25.77 ± 0.38 | 25.54 ± 0.35 | 51.51 ± 0.65 |

Triplicates of at least two independent experiments.

TABLE V

A. IC50 Values of VR-23.

| | | MDA-231 | MDA-468 | MCF7 | HeLa | Jurkat | U87MG | 184B5 | MCF10A |
|---|---|---|---|---|---|---|---|---|---|
| VR-23 | SRB | 3.4 ± 0.1 | 0.7 ± 0.1 | 2.3 ± 0.8 | 4.4 ± 3.0 | 0.8 ± 0.1 | 0.8 ± 0.1 | 9.0 ± 0.1 | 12.3 ± 1.0 |
| | Clonogenic | | | 1.2 ± 0.5 | | | 0.7 ± 0.5 | | |

B. Clonogenic assay using MCF7 cells.

| Drugs | Average colony number |
|---|---|
| Non-treated control | 36 |
| Bortezomib at 4 nM | 11 |
| Bortezomib at 6 nM | 6 |
| VR-23 at 1.5 μM | 2 |
| VR-23 at 1.5 μM | 0 |
| Bortezomib 4 nM plus VR-23 1.5 μM | 0 |
| Non-treated control | 34 |
| Bortezomib at 4 nM | 12 |
| Bortezomib at 2 nM | 15 |
| VR-23 at 0.37 μM | 25 |
| VR-23 at 0.75 μM | 27 |
| Bortezomib 4 nM plus VR-23 0.37 μM | 7 |

TABLE VI

A.

| Treatments (MCF7 breast cancer cells) | Survival (% of the control) |
|---|---|
| Percentage of survival in 1 nM of Paclitaxel alone | 35.8% |
| Percentage of survival in 1.5 μM of VR-23 alone | 50.3% |
| Percentage of survival in 1 nM of paclitaxel in combination with 1.5 μM of VR-23 | 21.9% |
| Percentage of survival in 2 nM of Paclitaxel alone | 9.5% |
| Percentage of survival in 1.5 μM of VR-23 alone | 50.3% |
| Percentage of survival in 2 nM of paclitaxel in combination with 1.5 μM of VR-23 | 3.0% |
| Percentage of survival in 1 nM of Paclitaxel alone | 35.8% |
| Percentage of survival in 3.1 μM of VR-23 alone | 46.8% |
| Percentage of survival in 1 nM of paclitaxel in combination with 3.1 μM of VR-23 | 4.1% |
| Percentage of survival in 2 nM of Paclitaxel alone | 9.5% |
| Percentage of survival in 3.1 μM of VR-23 alone | 46.8% |
| Percentage of survival in 2 nM of paclitaxel in combination with 3.1 μM of VR-23 | 3.8% |

B.

| Treatments (U87MG brain cancer cells) | # Colonies (Experiment #1) | # Colonies (Experiment #2) |
|---|---|---|
| Nontreated Control | 41 | 63 |
| DMSO Control | 45 | 81 |
| Temozolomide, 1 μM | 64 | 94 |
| Temozolomide, 5 μM | 39 | 50 |
| Temozolomide, 10 μM | 4 | 5 |
| Temozolomide, 20 μM | 2 | 1 |
| Temozolomide, 50 μM | 2 | 1 |
| VR-23, 2.5 μM | 0 | 0 |
| VR-23, 0.5 μM | 0 | Not done |
| Temozolomide, 1 μM + VR-23, 0.5 μM | 0 | Not done |

TABLE VII

| Proteasome | Inhibition (IC$_{50}$) |
|---|---|
| Trypsin-like | 1 nM |
| Chymotrypsin-like | 100 nM |
| Caspase-like | 3 μM |

TABLE VIII

Number of cells with multiple centrosomes

| | Time (hours - post DT) | | |
|---|---|---|---|
| | 3 | 6 | 12 |
| Nontreated Control | 1.3 ± 0.9 | 0 ± 0.0 | 3.8 ± 2.6 |
| VR-23 treated | 41 ± 11.8 | 55.2 ± 16.7 | 73.2 ± 1.0 | p = 0.0003 (or p < .05) using student's t-test

TABLE IX

|  | Dosage | Administration Frequency | Administration Method | Note |
|---|---|---|---|---|
| A. CD-1 mice | | | | |
| Vehicle control | Highest dose used for this experiment | Every 3 days | I.P.* | — |
| VR23 | 25 mg/kg | Every 3 days | I.P. | — |
| Paclitaxel | 20 mg/kg | Once per week | I.V.* | — |
| Tax* + VR-23 | 10 mg/kg Tax + 12.5 mg/kg VR-23 | Once per week | I.V. (Tax) & I.P. (VR-23) | Tax & VR-23 were given simultaneously |
| Tax, VR-23 | 20 mg/kg (Tax) 25 mg/kg (VR-23) | Once per week | I.V. (Tax) & I.P. (VR-23) | Tax was given 24 hours prior to VR-23 |
| B. ATH490 mice | | | | |
| Vehicle control | Highest dose used for this experiment | Every 3 days | I.P* | — |
| VR-23 | 30 mg/kg | Every 3 days | I.P. | — |
| Paclitaxel | 20 mg/kg | Once per week | I.V. | — |
| Tax, VR-23 | 20 mg/Kg (Tax) 30 mg/kg (VR23) | Once per week | I.V. (Tax) I.P. (VR23) | Tax was given 24 hours prior to VR23 |

*I.V. = intravenous injection; I.P. = intraperitoneal injection; Tax refers to paclitaxel

TABLE X

|  | D0 | D7 | D15 | D18 | D22 |
|---|---|---|---|---|---|
| Vehicle | 50.25 ± 4.84 | 94.5 ± 32.52 | 132.39 ± 32.56 | 246.72 ± 10.55 | 305.01 ± 37.95 |
| VR-23 | 46.51 ± 2.82 | 52.74 ± 5.64 | 48.29 ± 17.30 | 42.41 ± 17.95 | 65.88 ± 25.92 |
| Paclitaxel | 43.04 ± 4.05 | 47.63 ± 8.67 | 23.25 ± 11.63 | 25.20 ± 13.69 | 16.59 ± 2.66 |
| Paclitaxel, VR-23 | 50.69 ± 5.22 | 42.9 ± 9.91 | 20.16 ± 1.00 | 20.13 ± 7.80 | 10.51 ± 3.56 |

TABLE XI

| Treatments | Microscopic Changes |
|---|---|
| Untreated | Normal |
| Vehicle Control | Normal |
| VR-23, 30 mg/week | Largely (>95% of cases) normal |
| Paclitaxel, 20 mg/week | High rate of mitotic cells in liver (~130 mitotic cells/μm$^2$), with a small number of hepatocytes with hyperchromic nucleic acids |

TABLE XII

| A. CD-1 mice | |
|---|---|
| Treatments | ALT (IU/L blood) |
| DMSO (Vehicle) control | 6.46 ± 1.98 |
| Chloroquine (Reference) | 6.03 ± 4.40 |
| VR-23, 1 mg/kg | 6.40 ± 1.82 |
| VR-23, 5 mg/kg | 6.81 ± 0.32 |
| VR-23, 20 mg/kg | 16.19 ± 4.79 |

| B. ATH490 mice | | | |
|---|---|---|---|
|  | ALT (U/L) | AST (U/L) | Ratio (AST/ALT) |
| Untreated | 44.77 ± 1.31 | 82.35 ± 16.99 | 1.84 |
| Vehicle | 46.63 ± 3.90 | 74.73 ± 0.002 | 1.60 |
| VR-23 | 46.63 ± 6.16 | 62.52 ± 8.50 | 1.34 |
| Paclitaxel | 35.91 ± 4.26 | 84.4 ± 29.21 | 2.36 |

The invention claimed is:
1. A compound, wherein the compound is:
7-chloro-4-(4-(2,4-dinitrophenylsulfonyl)piperazin-1-yl) quinoline,
methyl 3-(4-(7-chloroquinolin-4-yl)piperazin-1-ylsulfonyl)thiophene-2-carboxylate,
7-chloro-4-(4-(biphenylsulfonyl)piperazin-1-yl)quinoline,
5-(4-(7-chloroquinolin-4-yl)piperazin-1-ylsulfonyl)-N,N-dimethylnaphthalen-1-amine,
7-chloro-4-(4-(2,4-dichlorophenylsulfonyl)piperazin-1-yl)quinoline,
4-[4-(3-nitro-benzenesulfonyl)-piperazin-1-yl]-7-trifluoromethylquinoline,
4-[4-(4-chloro-benzenesulfonyl)-piperazin-1-yl]-7-trifluoromethylquinoline,
4-[4-(toluene-4-sulfonyl)-piperazin-1-yl]-7-trifluoromethylquinoline,
4-[4-(biphenyl-4-sulfonyl)-piperazin-1-yl]-7-trifluoromethylquinoline,
4-[4-(2,4-dichloro-benzenesulfony)-piperazin-1-yl]-7-trifluoromethyl-quinoline,
4-(4-methanesufonyl-piperazin-1-yl)-7-trifluoromethyl-quinoline,
4-[4-(2,4-dinitro-benzenesulfonyl)-piperazin-1-yl]-7-trifluoromethyl-quinoline,
dimethyl-{5-[4-(7-trifluoromethyl-quinolin-4-yl)piperazine-1-sulfonyl]-naphthalen-1-yl}-amine, or
3-[4-(7-trifluoromethyl-quinolin-4-yl)-piperazine-1-sulfonyl]thiophene-2-carboxylic acid methyl ester,
or a pharmaceutically acceptable salt or solvate thereof.

2. A pharmaceutical composition comprising one or more compounds according to claim 1, or a pharmaceutically acceptable salt or solvate thereof, and a pharmaceutically acceptable carrier.

3. A method of treating a subject with cancer, the method comprising administering a compound, or a pharmaceutically acceptable salt or solvate thereof as defined in claim 1 or a pharmaceutical composition as defined in claim 2, to the subject, wherein the cancer is breast cancer, lymphoma, cervical cancer or brain cancer.

4. The method according to claim 3, wherein the compound or pharmaceutically acceptable salt thereof or the pharmaceutical composition is administered to the subject in combination with an anti-cancer agent.

5. The method according to claim 4, wherein the anti-cancer agent is selected from Bortezomib, paclitaxel, Monastrol, *Vinca*, VX-680, ZM447439, Hesperidin, temozolomide, Nocodazole, Bevacizumab, Cetuximab, Geftinib, Trastuzumab, Tipifarnib, CCI-779, Ly294002, Sunitinib maleate, API-1, and Akt1/2 inhibitor.

6. The method according to claim 3, wherein the subject is a human.

7. The compound according to claim 1, wherein the compound is 7-chloro-4-(4-(2,4-dinitrophenylsulfonyl)piperazin-1-yl)quinoline, or a pharmaceutically acceptable salt or solvate thereof.

8. The pharmaceutical composition according to claim 2, wherein the compound is 7-chloro-4-(4-(2,4-dinitrophenylsulfonyl)piperazin-1-yl)quinoline, or a pharmaceutically acceptable salt or solvate thereof.

9. The method according to claim 3, wherein the method comprises administering 7-chloro-4-(4-(2,4-dinitrophenylsulfonyl)piperazin-1-yl)quinoline, or a pharmaceutically acceptable salt or solvate thereof to the subject.

10. The method according to claim 4, wherein the anti-cancer agent is ionizing radiation.

11. The compound according to claim 1, wherein the compound is 7-chloro-4-(4-(2,4-dinitrophenylsulfonyl)piperazin-1-yl)quinoline.

12. The pharmaceutical composition according to claim 2, wherein the compound is 7-chloro-4-(4-(2,4-dinitrophenylsulfonyl)piperazin-1-yl)quinoline.

13. The method according to claim 9, wherein the method comprises administering 7-chloro-4-(4-(2,4-dinitrophenylsulfonyl)piperazin-1-yl)quinoline to the subject.

14. The method according to claim 13, wherein the compound is administered to the subject in combination with an anti-cancer agent.

15. The method according to claim 5, wherein the anti-cancer agent is paclitaxel or bortezomib.

16. The method according to claim 14, wherein the anti-cancer agent is paclitaxel or bortezomib.

17. The method according to claim 15, wherein the cancer is breast cancer.

* * * * *

UNITED STATES PATENT AND TRADEMARK OFFICE
CERTIFICATE OF CORRECTION

PATENT NO. : 9,975,852 B2  
APPLICATION NO. : 14/772701  
DATED : May 22, 2018  
INVENTOR(S) : Hoyun Lee et al.

Page 1 of 1

It is certified that error appears in the above-identified patent and that said Letters Patent is hereby corrected as shown below:

In the Claims

Claim 1, Column 88, Line 47, "4-(4-methanesufonyl-piperazin-1-yl)-7..." should read – "4-(4-methanesulfonyl-piperazin-1-yl)-7..."

Signed and Sealed this
Tenth Day of July, 2018

Andrei Iancu
*Director of the United States Patent and Trademark Office*